US012292085B2

(12) United States Patent
Dickinson et al.

(10) Patent No.: US 12,292,085 B2
(45) Date of Patent: May 6, 2025

(54) BREATHING ASSISTANCE APPARATUS

(71) Applicant: Fisher & Paykel Healthcare Limited, Auckland (NZ)

(72) Inventors: Philip John Dickinson, Auckland (NZ); Hayk Noobar Antranik Yaghobian, Auckland (NZ); Richard Daniel Panara, Auckland (NZ)

(73) Assignee: Fisher & Paykel Healthare Limited, Auckland (NZ)

( * ) Notice: Subject to any disclaimer, the term of this patent is extended or adjusted under 35 U.S.C. 154(b) by 109 days.

(21) Appl. No.: 17/806,152

(22) Filed: Jun. 9, 2022

(65) Prior Publication Data
US 2022/0307554 A1 Sep. 29, 2022

Related U.S. Application Data

(63) Continuation of application No. 16/607,352, filed as application No. PCT/NZ2018/050056 on Apr. 23, 2018, now Pat. No. 11,401,974.
(Continued)

(51) Int. Cl.
*F16C 35/067* (2006.01)
*A61M 16/00* (2006.01)
(Continued)

(52) U.S. Cl.
CPC ....... *F16C 35/067* (2013.01); *A61M 16/0066* (2013.01); *A61M 16/022* (2017.08);
(Continued)

(58) Field of Classification Search
CPC .......... A61M 16/0066; A61M 16/0069; A61M 2205/0216; A62B 18/045; F04D 17/16; F04D 29/4226; F04D 29/626
See application file for complete search history.

(56) References Cited

U.S. PATENT DOCUMENTS 2,189,252 A  2/1940 Reggio
2,874,722 A  2/1959 Hamblin
(Continued)

FOREIGN PATENT DOCUMENTS

AU  741687  7/2000
AU  2003204474  1/2004
(Continued)

OTHER PUBLICATIONS

US 8,334,630 B2, 12/2012, Saban et al. (withdrawn)
(Continued)

*Primary Examiner* — Joseph D. Boecker
(74) *Attorney, Agent, or Firm* — VIA LLP

(57) ABSTRACT

There is provided an apparatus for delivering a flow of gas having a controller, a housing defining a gasflow passage, a motor with an impeller to deliver gas through the gasflow passage, and a flexible printed circuit electrically connected to the motor for electrically connecting the motor to the controller. There is also provided an apparatus for delivering a flow of gas having a housing defining a gasflow passage. The gas flowing through the gasflow passage is a high concentration oxygen gas. The apparatus has a motor with windings and an impeller to deliver gas through the gasflow passage, and an elastomeric shield to pneumatically isolate the windings from the gasflow passage.

15 Claims, 59 Drawing Sheets

Related U.S. Application Data

(60) Provisional application No. 62/586,482, filed on Nov. 15, 2017, provisional application No. 62/488,845, filed on Apr. 23, 2017.

(51) Int. Cl.

| | |
|---|---|
| *F04D 29/42* | (2006.01) |
| *F04D 29/62* | (2006.01) |
| *F16C 27/06* | (2006.01) |
| *A61M 16/06* | (2006.01) |
| *A61M 16/10* | (2006.01) |
| *A61M 16/16* | (2006.01) |

(52) U.S. Cl.
CPC ....... *F04D 29/4226* (2013.01); *F04D 29/626* (2013.01); *F16C 27/063* (2013.01); *A61M 2016/0027* (2013.01); *A61M 2016/003* (2013.01); *A61M 16/0672* (2014.02); *A61M 16/109* (2014.02); *A61M 16/16* (2013.01); *A61M 2205/0216* (2013.01); *A61M 2205/3368* (2013.01); *A61M 2205/3592* (2013.01); *A61M 2205/7509* (2013.01); *A61M 2205/7518* (2013.01); *F16C 2316/10* (2013.01); *H05K 2201/10083* (2013.01)

(56) References Cited

U.S. PATENT DOCUMENTS

| | | |
|---|---|---|
| 2,929,944 A | 3/1960 | Shewmon |
| 2,969,262 A | 1/1961 | Staufert |
| 3,040,670 A | 6/1962 | Schenck et al. |
| 3,047,345 A | 7/1962 | Burton et al. |
| 3,395,649 A | 8/1968 | Marischen |
| 3,424,508 A | 1/1969 | Kizer et al. |
| 3,495,628 A | 2/1970 | Boender |
| 3,601,640 A | 8/1971 | Egawa |
| 3,926,223 A | 12/1975 | Petzetakis |
| 4,033,808 A | 7/1977 | Petzetakis |
| 4,161,667 A | 7/1979 | Buckman |
| 4,233,972 A | 11/1980 | Hauff et al. |
| 4,357,552 A | 11/1982 | MacMillan |
| 4,530,639 A | 7/1985 | Mowill |
| 4,531,551 A | 7/1985 | Eichelberger et al. |
| 4,587,450 A | 5/1986 | Ozaki |
| 4,590,951 A | 5/1986 | O'Connor |
| 4,623,812 A | 11/1986 | van de Griend |
| 4,713,530 A | 12/1987 | Schittenhelm et al. |
| 4,773,448 A | 9/1988 | Francis |
| 4,837,921 A | 6/1989 | Tassinario |
| 4,888,465 A | 12/1989 | Hoffmann |
| 4,889,116 A | 12/1989 | Taube |
| 4,903,736 A | 2/1990 | Baston et al. |
| 5,127,442 A | 7/1992 | Blomqvist |
| 5,211,171 A | 5/1993 | Choromokos |
| 5,237,737 A | 8/1993 | Zigler et al. |
| 5,432,322 A | 7/1995 | Ingram et al. |
| 5,484,270 A | 1/1996 | Adahan |
| 5,521,357 A | 5/1996 | Lock et al. |
| 5,521,576 A | 5/1996 | Collins |
| 5,567,127 A | 10/1996 | Wentz |
| 5,591,292 A | 1/1997 | Blomqvist |
| 5,601,400 A | 2/1997 | Kondo et al. |
| 5,605,444 A | 2/1997 | Paton et al. |
| 5,608,591 A | 3/1997 | Klaassen |
| 5,627,423 A | 5/1997 | Marioni |
| 5,640,951 A | 6/1997 | Huddart et al. |
| 5,662,611 A | 9/1997 | Beiser et al. |
| 5,672,927 A | 9/1997 | Viskochil |
| 5,694,268 A | 12/1997 | Dunfield et al. |
| 5,701,883 A | 12/1997 | Hete et al. |
| 5,797,727 A | 8/1998 | Peters et al. |
| 5,875,783 A | 3/1999 | Draegerwerk |
| 5,878,743 A | 3/1999 | Zdrojkowski et al. |
| 5,923,111 A | 7/1999 | Eno et al. |
| 5,967,764 A | 10/1999 | Booth et al. |
| 6,017,315 A | 1/2000 | Starr et al. |
| 6,050,262 A | 4/2000 | Jay |
| 6,073,630 A | 6/2000 | Adahan |
| 6,105,649 A | 8/2000 | Levingston et al. |
| 6,194,692 B1 | 2/2001 | Oberle |
| 6,210,116 B1 | 4/2001 | Kuczaj et al. |
| 6,216,691 B1 | 4/2001 | Kenyon et al. |
| 6,222,158 B1 | 4/2001 | Nakata et al. |
| 6,302,105 B1 | 10/2001 | Wickham et al. |
| 6,376,952 B1 | 4/2002 | Stenta |
| 6,401,713 B1 | 6/2002 | Hill et al. |
| 6,435,180 B1 | 8/2002 | Hewson et al. |
| 6,439,861 B1 | 8/2002 | Shieh |
| 6,483,087 B2 | 11/2002 | Gardner et al. |
| 6,487,047 B1 | 11/2002 | Balakrishnan |
| 6,516,801 B2 | 2/2003 | Boussignac |
| 6,537,405 B1 | 3/2003 | Henderson et al. |
| 6,543,449 B1 | 4/2003 | Woodring et al. |
| 6,601,621 B2 | 8/2003 | Wixey et al. |
| 6,622,724 B1 | 9/2003 | Truitt et al. |
| 6,629,528 B1 | 10/2003 | Wickham et al. |
| 6,644,310 B1 | 11/2003 | Delache et al. |
| 6,700,255 B1 | 3/2004 | Stenta |
| 6,717,299 B2 | 4/2004 | Bacile et al. |
| 6,722,359 B2 | 4/2004 | Chalvignac |
| 6,802,648 B2 | 10/2004 | Merot et al. |
| 6,817,088 B1 | 11/2004 | Lin |
| 6,848,444 B2 | 2/2005 | Smith et al. |
| 6,899,100 B2 | 5/2005 | Wickham et al. |
| 6,910,483 B2 | 6/2005 | Daly et al. |
| 7,012,346 B2 | 3/2006 | Hoffman et al. |
| 7,028,677 B2 | 4/2006 | Martin |
| 7,075,203 B2 | 7/2006 | Kuwert |
| 7,096,864 B1 | 8/2006 | Mayer et al. |
| 7,121,874 B1 | 10/2006 | Jeon |
| 7,128,069 B2 | 10/2006 | Farrugia et al. |
| 7,240,583 B2 | 7/2007 | Wingett et al. |
| 7,241,131 B1 | 7/2007 | Booth et al. |
| 7,244,099 B2 | 7/2007 | Yamasaki |
| 7,262,568 B2 | 8/2007 | Takada |
| 7,314,046 B2 | 1/2008 | Schroeder et al. |
| 7,340,966 B2 | 3/2008 | DiMatteo et al. |
| 7,365,458 B2 | 4/2008 | Yoshida |
| 7,384,237 B2 | 6/2008 | Baecke et al. |
| 7,413,173 B2 | 8/2008 | DiMatteo et al. |
| 7,448,383 B2 | 11/2008 | Kaerys |
| 7,508,102 B2 | 3/2009 | Sugiyama et al. |
| 7,516,743 B2 | 4/2009 | Hoffman |
| 7,571,725 B2 | 8/2009 | Virr et al. |
| 7,617,823 B2 | 11/2009 | DiMatteo et al. |
| 7,677,246 B2 | 3/2010 | Kepler et al. |
| 7,708,013 B2 | 5/2010 | Niland et al. |
| 7,827,981 B2 | 11/2010 | Bamford |
| 7,874,290 B2 | 1/2011 | Chalvignac |
| 7,913,692 B2 | 3/2011 | Kwok |
| 7,938,112 B2 | 5/2011 | Mayer et al. |
| 7,939,975 B2 | 5/2011 | Saga et al. |
| 7,942,380 B2 | 5/2011 | Bertinetti et al. |
| 7,975,688 B1 | 7/2011 | Truitt |
| 8,006,691 B2 | 8/2011 | Kenyon et al. |
| 8,011,362 B2 | 9/2011 | Adams |
| 8,020,551 B2 | 9/2011 | Virr et al. |
| 8,020,556 B2 | 9/2011 | Shahar |
| 8,020,557 B2 | 9/2011 | Bordewick et al. |
| 8,028,693 B2 | 10/2011 | Trevor-Wilson et al. |
| 8,042,535 B2 | 10/2011 | Kenyon et al. |
| 8,074,645 B2 | 12/2011 | Bordewick et al. |
| 8,074,647 B2 | 12/2011 | Truitt et al. |
| 8,080,907 B2 | 12/2011 | Jeung |
| 8,122,884 B2 | 2/2012 | Daly et al. |
| 8,186,345 B2 | 5/2012 | Payton et al. |
| 8,302,598 B2 | 11/2012 | Haase et al. |
| 8,353,292 B2 | 1/2013 | Chalvignac |
| 8,375,944 B2 | 2/2013 | Kwok |
| 8,375,945 B2 | 2/2013 | Kepler et al. |
| 8,393,320 B2 | 3/2013 | Kenyon |
| 8,436,608 B2 | 5/2013 | Sun et al. |

(56) References Cited

U.S. PATENT DOCUMENTS

| | | |
|---|---|---|
| 8,450,898 B2 | 5/2013 | Sears et al. |
| 8,453,640 B2 | 6/2013 | Martin et al. |
| 8,469,025 B2 | 6/2013 | Mayer et al. |
| 8,481,902 B2 | 7/2013 | Leboeuf et al. |
| 8,496,001 B2 | 7/2013 | Schermeier et al. |
| 8,499,760 B2 | 7/2013 | Schermeier et al. |
| D688,788 S | 8/2013 | Spruell et al. |
| 8,517,012 B2 | 8/2013 | Daly et al. |
| 8,544,465 B2 | 10/2013 | Smith et al. |
| 8,553,364 B1 | 10/2013 | Schreiber et al. |
| 8,602,025 B2 | 12/2013 | Bordewick et al. |
| 8,602,747 B2 | 12/2013 | Takada |
| 8,627,819 B2 | 1/2014 | DeVries et al. |
| 8,631,789 B2 | 1/2014 | Virr et al. |
| 8,631,791 B2 | 1/2014 | Bordewick et al. |
| 8,638,014 B2 | 1/2014 | Sears et al. |
| 8,701,662 B2 | 4/2014 | Pujol et al. |
| 8,733,349 B2 | 5/2014 | Bath et al. |
| 8,739,780 B2 | 6/2014 | Tang et al. |
| 8,816,558 B2 | 8/2014 | Sears et al. |
| 8,899,232 B2 | 12/2014 | Farrugia et al. |
| 8,915,247 B2 | 12/2014 | Chalvignac |
| 8,931,481 B2 | 1/2015 | Jones et al. |
| 8,973,576 B2 | 3/2015 | Kenyon |
| 9,004,067 B2 | 4/2015 | Kenyon et al. |
| 9,010,324 B2 | 4/2015 | Martin et al. |
| 9,038,629 B2 | 5/2015 | Smith et al. |
| 9,038,631 B2 | 5/2015 | Bath et al. |
| 9,038,632 B2 | 5/2015 | Crumblin et al. |
| 9,048,715 B2 | 6/2015 | Kodani et al. |
| 9,072,860 B2 | 7/2015 | Lithgow et al. |
| 9,089,660 B2 | 7/2015 | Chalvignac |
| 9,127,691 B2 | 9/2015 | Hagen et al. |
| 9,132,250 B2 | 9/2015 | Allum |
| 9,132,252 B2 | 9/2015 | Barlow |
| 9,227,035 B2 | 1/2016 | Crumblin et al. |
| 9,272,116 B2 | 3/2016 | Mayer et al. |
| 9,302,066 B2 | 4/2016 | Bertinetti et al. |
| 9,302,067 B2 | 4/2016 | Mayer et al. |
| 9,358,359 B2 | 6/2016 | Lithgow et al. |
| 9,375,543 B2 | 6/2016 | Lubrett et al. |
| 9,393,377 B2 | 7/2016 | Smith et al. |
| 9,402,970 B2 | 8/2016 | Virr et al. |
| 9,427,538 B2 | 8/2016 | Daly et al. |
| 9,479,022 B2 | 10/2016 | Hoemann et al. |
| 9,481,424 B2 | 11/2016 | Hagen et al. |
| 9,539,409 B2 | 1/2017 | Crumblin et al. |
| 9,545,493 B2 | 1/2017 | Mayer et al. |
| 9,545,494 B2 | 1/2017 | Mayer et al. |
| 9,555,211 B2 | 1/2017 | Mayer et al. |
| 9,610,416 B2 | 4/2017 | Jones et al. |
| 9,610,420 B2 | 4/2017 | Lithgow et al. |
| 9,656,034 B2 | 5/2017 | Kepler et al. |
| 9,737,682 B2 | 8/2017 | Maurer et al. |
| 9,750,907 B2 | 9/2017 | Librett et al. |
| 9,802,022 B2 | 10/2017 | Smith et al. |
| 10,052,450 B2 | 8/2018 | Mayer et al. |
| 10,137,264 B2 | 11/2018 | Darby et al. |
| 10,195,389 B2 | 2/2019 | Virr et al. |
| 10,238,822 B2 | 3/2019 | Barlow et al. |
| 10,286,167 B2 | 5/2019 | Bothma et al. |
| 10,471,225 B2 | 11/2019 | Bothma et al. |
| 11,401,974 B2 | 8/2022 | Dickinson et al. |
| 11,534,565 B2 | 12/2022 | Bothma et al. |
| 11,571,536 B2 | 2/2023 | Bothma et al. |
| 2003/0235012 A1 | 12/2003 | Nishizawa |
| 2005/0103339 A1 | 5/2005 | Daly et al. |
| 2005/0188989 A1 | 9/2005 | Delache et al. |
| 2005/0202697 A1 | 9/2005 | Caveney et al. |
| 2005/0210622 A1 | 9/2005 | Baecke et al. |
| 2006/0017815 A1 | 1/2006 | Stavely et al. |
| 2006/0043802 A1* | 3/2006 | Sugiyama ............... H02K 3/522 |
| | | 310/67 R |
| 2006/0096596 A1 | 5/2006 | Occhialini et al. |
| 2006/0158785 A1 | 7/2006 | Arya et al. |
| 2006/0237013 A1 | 10/2006 | Kwok |
| 2007/0017518 A1 | 1/2007 | Farrugia et al. |
| 2007/0132335 A1 | 6/2007 | Ionel et al. |
| 2007/0166659 A1 | 7/2007 | Hasse et al. |
| 2007/0251527 A1 | 11/2007 | Sleeper |
| 2007/0277827 A1 | 12/2007 | Bordewick et al. |
| 2007/0284952 A1 | 12/2007 | Ihle |
| 2008/0000474 A1 | 1/2008 | Jochle et al. |
| 2008/0014104 A1 | 1/2008 | Huang et al. |
| 2008/0142368 A1 | 6/2008 | Warren et al. |
| 2008/0149306 A1 | 6/2008 | Hwang et al. |
| 2008/0178879 A1 | 7/2008 | Roberts et al. |
| 2008/0216831 A1 | 9/2008 | McGinnis et al. |
| 2008/0216835 A1 | 9/2008 | McGinnis et al. |
| 2008/0235646 A1 | 9/2008 | Petunin |
| 2008/0240632 A1 | 10/2008 | McMurray |
| 2008/0304986 A1* | 12/2008 | Kenyon ................... H02K 9/14 |
| | | 417/423.12 |
| 2009/0020120 A1 | 1/2009 | Schatzl et al. |
| 2009/0071480 A1 | 3/2009 | Adams |
| 2009/0108686 A1 | 4/2009 | Jeung |
| 2009/0194101 A1 | 8/2009 | Kenyon |
| 2009/0223514 A1 | 9/2009 | Smith et al. |
| 2009/0256295 A1 | 10/2009 | Kodama |
| 2009/0301485 A1 | 12/2009 | Kenyon et al. |
| 2009/0315492 A1 | 12/2009 | Oomura |
| 2009/0320842 A1 | 12/2009 | Doherty |
| 2009/0324435 A1 | 12/2009 | Sears et al. |
| 2010/0000535 A1 | 1/2010 | Wickham et al. |
| 2010/0059055 A1 | 3/2010 | Brungart et al. |
| 2010/0059056 A1* | 3/2010 | Sears ....................... H02K 9/14 |
| | | 310/90 |
| 2010/0116272 A1 | 5/2010 | Row et al. |
| 2010/0132711 A1 | 6/2010 | Kenyon |
| 2010/0170513 A1 | 7/2010 | Bowditch et al. |
| 2010/0192094 A1 | 7/2010 | Jeha et al. |
| 2011/0023874 A1 | 2/2011 | Bath et al. |
| 2011/0052205 A1 | 3/2011 | Yu et al. |
| 2011/0073110 A1 | 3/2011 | Kenyon |
| 2011/0114815 A1 | 5/2011 | Valovick et al. |
| 2011/0132363 A1 | 6/2011 | Chalvignac |
| 2011/0197884 A1 | 8/2011 | Duff et al. |
| 2011/0203587 A1 | 8/2011 | Bertinetti et al. |
| 2012/0000463 A1 | 1/2012 | Bordewick et al. |
| 2012/0080032 A1 | 4/2012 | Bordewick et al. |
| 2012/0097156 A1 | 4/2012 | Bowman et al. |
| 2012/0107157 A1 | 5/2012 | Tsai |
| 2012/0138058 A1 | 6/2012 | Fu et al. |
| 2012/0152255 A1 | 6/2012 | Barlow et al. |
| 2012/0167879 A1 | 7/2012 | Bowman |
| 2012/0227738 A1 | 9/2012 | Virr et al. |
| 2012/0266873 A1 | 10/2012 | Lalonde |
| 2012/0269666 A1 | 10/2012 | Lin et al. |
| 2012/0285454 A1 | 11/2012 | Nibu et al. |
| 2012/0319543 A1 | 12/2012 | Adachi et al. |
| 2013/0098359 A1 | 4/2013 | Becker et al. |
| 2013/0152918 A1 | 6/2013 | Rummery |
| 2013/0164158 A1 | 6/2013 | Matsuba et al. |
| 2013/0280055 A1 | 10/2013 | Daly et al. |
| 2013/0298908 A1 | 11/2013 | Tang et al. |
| 2013/0306072 A1 | 11/2013 | Moir |
| 2013/0340757 A1 | 12/2013 | Smith et al. |
| 2014/0007871 A1 | 1/2014 | Bordewick et al. |
| 2014/0020684 A1 | 1/2014 | Klasek et al. |
| 2014/0034633 A1 | 2/2014 | Heintz et al. |
| 2014/0041663 A1 | 2/2014 | Daly et al. |
| 2014/0069432 A1 | 3/2014 | Mebasser et al. |
| 2014/0090645 A1 | 4/2014 | Sears et al. |
| 2014/0131904 A1 | 5/2014 | Tang et al. |
| 2014/0138804 A1 | 5/2014 | Takizawa et al. |
| 2014/0158131 A1 | 6/2014 | Kenyon et al. |
| 2014/0166007 A1 | 6/2014 | Bordewick et al. |
| 2014/0178079 A1 | 6/2014 | Yagisawa et al. |
| 2014/0202460 A1 | 7/2014 | Bath et al. |
| 2014/0205513 A1 | 7/2014 | Affaitati |
| 2014/0216460 A1 | 8/2014 | Bothma et al. |
| 2014/0227091 A1 | 8/2014 | Kenyon et al. |
| 2014/0242816 A1 | 8/2014 | Rathburn |
| 2014/0261422 A1 | 9/2014 | Lang et al. |

(56) References Cited

U.S. PATENT DOCUMENTS

| | | |
|---|---|---|
| 2014/0264975 A1 | 9/2014 | Bath et al. |
| 2014/0299132 A1 | 10/2014 | Librett et al. |
| 2014/0332001 A1 | 11/2014 | Bath et al. |
| 2015/0000653 A1 | 1/2015 | Miller |
| 2015/0000655 A1 | 1/2015 | Desilva et al. |
| 2015/0000662 A1 | 1/2015 | Williams et al. |
| 2015/0000663 A1 | 1/2015 | Williams et al. |
| 2015/0000664 A1 | 1/2015 | Desilva et al. |
| 2015/0000669 A1 | 1/2015 | Miller |
| 2015/0003966 A1 | 1/2015 | Duquette |
| 2015/0007815 A1 | 1/2015 | Duquette et al. |
| 2015/0030317 A1 | 1/2015 | Bayer et al. |
| 2015/0047639 A1 | 2/2015 | Farrugia et al. |
| 2015/0122685 A1 | 5/2015 | Wakeham et al. |
| 2015/0136140 A1 | 5/2015 | Kenyon et al. |
| 2015/0136467 A1 | 5/2015 | Rathburn |
| 2015/0157818 A1 | 6/2015 | Darby et al. |
| 2015/0158478 A1 | 6/2015 | Stahr et al. |
| 2015/0190605 A1 | 7/2015 | Martin et al. |
| 2015/0230289 A1 | 8/2015 | Corona |
| 2015/0230750 A1 | 8/2015 | McDarby et al. |
| 2015/0231358 A1 | 8/2015 | Smith et al. |
| 2015/0250963 A1 | 9/2015 | Ramanan et al. |
| 2015/0290415 A1 | 10/2015 | Dunn |
| 2015/0301567 A1 | 10/2015 | Chen et al. |
| 2015/0320960 A1 | 11/2015 | Barlow et al. |
| 2015/0328418 A1 | 11/2015 | Bothma et al. |
| 2015/0335846 A1 | 11/2015 | Romagnoli et al. |
| 2016/0010649 A1 | 1/2016 | Aiello |
| 2016/0015919 A1 | 1/2016 | Librett et al. |
| 2016/0022954 A1 | 1/2016 | Bath et al. |
| 2016/0045693 A1 | 2/2016 | Librett et al. |
| 2016/0087505 A1 | 3/2016 | Turner et al. |
| 2016/0114121 A1 | 4/2016 | Holley et al. |
| 2016/0192507 A1 | 6/2016 | Rathburn |
| 2016/0199612 A1 | 7/2016 | Foote et al. |
| 2016/0303343 A1 | 10/2016 | Virr et al. |
| 2016/0310691 A1 | 10/2016 | Bath et al. |
| 2016/0317775 A1 | 11/2016 | Smith et al. |
| 2016/0333885 A1 | 11/2016 | Daly et al. |
| 2016/0339193 A1 | 11/2016 | Daly et al. |
| 2016/0346499 A1 | 12/2016 | Williams et al. |
| 2017/0082116 A1 | 3/2017 | Nibu et al. |
| 2017/0087327 A1 | 3/2017 | Crumblin et al. |
| 2017/0087328 A1 | 3/2017 | Mayer et al. |
| 2017/0114801 A1 | 4/2017 | Duquette |
| 2017/0151401 A9 | 6/2017 | Darby et al. |
| 2017/0157347 A1 | 6/2017 | Jones et al. |
| 2017/0182270 A1 | 6/2017 | Kenyon et al. |
| 2017/0204868 A1 | 7/2017 | Oshita et al. |
| 2017/0232221 A1 | 8/2017 | Kepler et al. |
| 2017/0248145 A1 | 8/2017 | Chu et al. |
| 2017/0312473 A1 | 11/2017 | Desilva et al. |
| 2017/0326329 A1 | 11/2017 | Maurer et al. |
| 2017/0340847 A1 | 11/2017 | Taylor et al. |
| 2017/0350737 A1 | 12/2017 | Desilva et al. |
| 2018/0008795 A1 | 1/2018 | Smith et al. |
| 2018/0142690 A1 | 5/2018 | Row et al. |
| 2018/0156233 A1 | 6/2018 | Sawada et al. |
| 2019/0001091 A1 | 1/2019 | Bath et al. |
| 2019/0160239 A1 | 5/2019 | Darby et al. |
| 2019/0262561 A1 | 8/2019 | Bothma et al. |
| 2020/0101245 A1 | 4/2020 | Bothma et al. |
| 2020/0124104 A1 | 4/2020 | Dickinson et al. |
| 2023/0133462 A1 | 5/2023 | Bothma et al. |
| 2023/0211097 A1 | 7/2023 | Bothma et al. |

FOREIGN PATENT DOCUMENTS

| | | |
|---|---|---|
| AU | 2009288026 | 3/2010 |
| AU | 2014/250602 | 11/2014 |
| CA | 1289037 | 9/1991 |
| CA | 2636623 A1 | 7/2007 |
| CA | 2721674 | 10/2009 |
| CA | 2778080 | 4/2011 |
| CA | 2686843 | 6/2011 |
| CA | 2840594 | 1/2013 |
| CN | 1266150 A | 9/2000 |
| CN | 1712739 A | 12/2005 |
| CN | 1932329 | 3/2007 |
| CN | 101296722 A | 10/2008 |
| CN | 101321958 A | 12/2008 |
| CN | 101323235 | 12/2008 |
| CN | 101449064 A | 6/2009 |
| CN | 101466429 A | 6/2009 |
| CN | 101541367 A | 9/2009 |
| CN | 101553667 | 10/2009 |
| CN | 101686609 A | 3/2010 |
| CN | 101836348 | 9/2010 |
| CN | 201805562 | 4/2011 |
| CN | 102832734 A | 12/2012 |
| CN | 103167777 A | 6/2013 |
| CN | 104097294 A | 10/2014 |
| CN | 106849411 | 6/2017 |
| DE | 3310376 A1 | 9/1984 |
| DE | 4020522 | 1/1992 |
| DE | 102005000819 | 7/2006 |
| DE | 102007026565 | 12/2007 |
| EP | 0637361 | 12/1994 |
| EP | 0634588 | 1/1995 |
| EP | 1035330 B1 | 9/2000 |
| EP | 1064042 | 1/2001 |
| EP | 1123674 | 8/2001 |
| EP | 1 147 004 | 10/2001 |
| EP | 1205203 A2 | 5/2002 |
| EP | 1210139 | 6/2002 |
| EP | 1205203 A3 | 7/2002 |
| EP | 1205203 B1 | 9/2004 |
| EP | 1638503 | 3/2006 |
| EP | 1638631 | 3/2006 |
| EP | 1648544 | 4/2006 |
| EP | 1662148 | 5/2006 |
| EP | 1669098 | 6/2006 |
| EP | 17193255 | 8/2006 |
| EP | 1760319 A1 | 3/2007 |
| EP | 1824542 | 8/2007 |
| EP | 1924311 | 5/2008 |
| EP | 1933910 | 6/2008 |
| EP | 2000675 A2 | 12/2008 |
| EP | 2010260 | 1/2009 |
| EP | 2012858 | 1/2009 |
| EP | 2098260 | 9/2009 |
| EP | 2112938 | 11/2009 |
| EP | 2308539 | 4/2011 |
| EP | 2317150 A1 | 5/2011 |
| EP | 2337604 | 6/2011 |
| EP | 2345443 | 7/2011 |
| EP | 2345449 | 7/2011 |
| EP | 2355880 | 8/2011 |
| EP | 2392375 | 12/2011 |
| EP | 2440277 | 4/2012 |
| EP | 2464404 | 6/2012 |
| EP | 2470246 | 7/2012 |
| EP | 2471568 | 7/2012 |
| EP | 2494213 | 9/2012 |
| EP | 2496297 | 9/2012 |
| EP | 2501439 | 9/2012 |
| EP | 17198437 | 9/2012 |
| EP | 2572747 | 3/2013 |
| EP | 2694146 | 2/2014 |
| EP | 2731656 | 5/2014 |
| EP | 2809383 | 12/2014 |
| EP | 2910271 | 8/2015 |
| EP | 2968804 | 1/2016 |
| EP | 2968805 | 1/2016 |
| EP | 2968829 | 1/2016 |
| EP | 2992921 | 3/2016 |
| EP | 3013397 | 5/2016 |
| EP | 3013398 | 5/2016 |
| EP | 3013399 | 5/2016 |
| EP | 3013400 | 5/2016 |
| EP | 3013402 | 5/2016 |
| EP | 3014224 | 5/2016 |
| EP | 3014225 | 5/2016 |

(56) References Cited

FOREIGN PATENT DOCUMENTS

| | | |
|---|---|---|
| EP | 3082920 | 10/2016 |
| EP | 3148418 | 4/2017 |
| EP | 3148419 | 4/2017 |
| EP | 3149696 | 4/2017 |
| EP | 3160561 | 5/2017 |
| EP | 3160562 | 5/2017 |
| EP | 3160564 | 5/2017 |
| EP | 3213788 | 9/2017 |
| EP | 3219350 | 9/2017 |
| EP | 3311869 | 4/2018 |
| EP | 3311871 | 4/2018 |
| EP | 3470104 | 4/2019 |
| EP | 3865169 | 8/2021 |
| FR | 2617250 | 12/1988 |
| FR | 2826412 | 12/2002 |
| FR | 2901998 | 12/2007 |
| GB | 144627 | 7/1920 |
| GB | 146832 | 12/1920 |
| GB | 525 551 | 8/1940 |
| GB | 948382 A | 2/1964 |
| GB | 1041313 A | 9/1966 |
| GB | 2217924 | 11/1989 |
| JP | 58133153 | 8/1983 |
| JP | 60-192676 | 12/1985 |
| JP | 7-7898 | 1/1995 |
| JP | 9172748 | 6/1997 |
| JP | 3060967 | 9/1999 |
| JP | 2000-217302 | 8/2000 |
| JP | 2002-511786 A | 4/2002 |
| JP | 4046539 | 10/2003 |
| JP | 2004-353655 A | 12/2004 |
| JP | 2007-506482 A | 3/2007 |
| JP | 2007-518497 | 7/2007 |
| JP | 2009-178557 | 8/2009 |
| JP | 2009-533153 A | 9/2009 |
| JP | 2013-501541 A | 1/2013 |
| JP | 2018-008120 | 1/2018 |
| NZ | 544142 | 1/2009 |
| NZ | 544765 | 1/2009 |
| NZ | 573198 | 6/2010 |
| NZ | 573227 | 7/2010 |
| NZ | 575332 | 10/2010 |
| NZ | 564886 | 2/2011 |
| NZ | 579384 | 5/2011 |
| NZ | 585403 | 10/2011 |
| NZ | 585404 | 10/2011 |
| NZ | 585683 | 12/2011 |
| NZ | 587113 | 12/2011 |
| NZ | 586325 | 1/2012 |
| NZ | 589766 | 5/2012 |
| WO | WO 87/01599 | 3/1987 |
| WO | WO 1999/013931 | 3/1999 |
| WO | WO 1999/22794 | 5/1999 |
| WO | WO 00/76053 | 12/2000 |
| WO | WO 01/10002 | 2/2001 |
| WO | WO 2002/049188 | 6/2002 |
| WO | WO 2004/108198 | 12/2004 |
| WO | WO 2004/112873 | 12/2004 |
| WO | WO 2007/019628 | 2/2007 |
| WO | WO 2007/024955 | 3/2007 |
| WO | WO 2007/024956 | 3/2007 |
| WO | WO 2007/038152 | 4/2007 |
| WO | WO 2007/048206 A1 | 5/2007 |
| WO | WO 2007/117716 | 10/2007 |
| WO | WO 2007/134405 A1 | 11/2007 |
| WO | WO 2007/149446 | 12/2007 |
| WO | WO 2008/028247 | 3/2008 |
| WO | WO 2008/051534 | 5/2008 |
| WO | WO 2008/092235 A1 | 8/2008 |
| WO | WO 2008/102216 | 8/2008 |
| WO | WO 2010/028121 | 3/2010 |
| WO | WO 2010/084183 | 7/2010 |
| WO | WO 2010/096467 A1 | 8/2010 |
| WO | WO 2011/017763 A1 | 2/2011 |
| WO | WO 2011/022557 | 2/2011 |
| WO | WO 2011/022779 A1 | 3/2011 |
| WO | WO 2011/051462 | 5/2011 |
| WO | WO 2011/054038 | 5/2011 |
| WO | WO 2011/062633 | 5/2011 |
| WO | WO 2011/112807 | 9/2011 |
| WO | WO 2011/116428 | 9/2011 |
| WO | WO 2012/024740 | 3/2012 |
| WO | WO 2012/094230 | 7/2012 |
| WO | WO 2012/113027 | 8/2012 |
| WO | WO 2012/135912 | 10/2012 |
| WO | WO 2012/145358 A2 | 10/2012 |
| WO | WO 2012/174602 | 12/2012 |
| WO | WO 2013/009193 | 1/2013 |
| WO | WO 2013/010736 A1 | 1/2013 |
| WO | WO 2013/020167 | 2/2013 |
| WO | WO 2013/152403 | 10/2013 |
| WO | WO 2013/163685 | 11/2013 |
| WO | WO 2013/163687 | 11/2013 |
| WO | WO 2013/173219 | 11/2013 |
| WO | WO 2014/007655 | 1/2014 |
| WO | WO 2014/097030 | 6/2014 |
| WO | WO 2014/138804 | 9/2014 |
| WO | WO2015/120521 | 9/2014 |
| WO | WO 2014/184377 | 11/2014 |
| WO | WO 2014/201513 | 12/2014 |
| WO | WO2014/205513 | 12/2014 |
| WO | WO2015/000025 | 1/2015 |
| WO | WO2015/048857 | 4/2015 |
| WO | WO2015/058255 | 4/2015 |
| WO | WO2015/061848 | 5/2015 |
| WO | WO2015/089582 | 6/2015 |
| WO | WO2015/120522 | 8/2015 |
| WO | WO2015/131219 | 9/2015 |
| WO | WO2015/179915 | 12/2015 |
| WO | WO2015/179916 | 12/2015 |
| WO | WO2015/179917 | 12/2015 |
| WO | WO2015/188227 | 12/2015 |
| WO | WO2015/192186 | 12/2015 |
| WO | WO2015/196255 | 12/2015 |
| WO | WO2016/000040 | 1/2016 |
| WO | WO 2016/009771 A1 | 1/2016 |
| WO | WO2016/019292 | 2/2016 |
| WO | WO2016/029265 | 3/2016 |
| WO | WO 2016/194697 A1 | 12/2016 |
| WO | WO 2017/006189 A1 | 1/2017 |
| WO | WO 2017/027906 | 2/2017 |
| WO | WO 2017/068530 A3 | 4/2017 |

OTHER PUBLICATIONS

International Search Report and Written Opinion of the International Searching Authority for International Application No. PCT/NZ2018/050056, mailed on Sep. 11, 2018, in 49 pages.
http://www.broadleyjames.com/bionet-parts-list/rushton-60mm-5-71.html.
http://www.fao.org/docrep/010/ah810e/ah810e07.htm.

* cited by examiner

BREATHING ASSISTANCE APPARATUS

INCORPORATION BY REFERENCE

The present application is a continuation of U.S. patent application Ser. No. 16/607,352, filed Oct. 22, 2019, which is the national phase under 35 U.S.C § 371 of PCT International Application No. PCT/NZ2018/050056, filed Apr. 23, 2018, which claims priority benefit of U.S. Provisional Application No. 62/488,845, filed Apr. 23, 2017; and U.S. Provisional Application No. 62/586,482, filed Nov. 15, 2017, each of which is hereby incorporated by reference in its s entirety.

TECHNICAL FIELD

The present disclosure relates to a flow therapy apparatus for delivering gas to patients.

BACKGROUND ART

Breathing assistance apparatuses are used in various environments such as hospital, medical facility, residential care, or home environments to deliver a flow of gas to users or patients.

SUMMARY

The applicant has identified explosion safety risk if some gases, such as high concentration oxygen for example, come into contact with electrical and/or electronics components in breathing assistance apparatuses.

Accordingly, it would be desirable to provide an apparatus for delivering a flow of gas that isolates gas flow from electrical and/or electronic components, and/or at least provides the public with a useful choice.

Thus, in accordance with certain features, aspects and advantages of at least one of the embodiments disclosed herein, a bearing mount for supporting a bearing is disclosed, the bearing mount comprising:
an annular body,
a collar extending concentrically with the annular body and outwardly from the annular body, the collar having a narrower outer diameter than an outer diameter of the annular body forming a recess between the annular body and the collar,
a central bore extending through the annular body and the collar, the central bore having a wall and a ledge extending radially inwardly from the wall of the central bore,
the ledge being disposed near one end of the central bore and the collar being disposed near another end of the central bore,
wherein the bearing mount is arranged to receive the bearing in the central bore such that the bearing is radially supported by the inner surface of the bearing mount, and axially supported by the ledge, and
wherein at least part of the bearing mount is arranged to flex or resiliently deform when a force is applied to the bearing mount to reduce the amount of the force that is translated to the bearing.

In some configurations, at least part of the bearing mount is arranged to flex or resiliently deform such that the collar moves in a direction generally parallel to the bearing rotational axis when the force is applied to the bearing mount.

In some configurations, at least part of the bearing mount is arranged to flex or resiliently deform when a force is applied to the bearing mount such that the force translated to the bearing retained in the central bore remains generally constant as the force applied to the bearing mount increases beyond a threshold.

In some configurations, the recess provides an area into which the annular body may flex or resiliently deform when a force is applied to the bearing mount.

In some configurations, the annular body extends outwardly at a non-perpendicular angle relative to the bearing rotational axis.

In some configurations, the annular body comprises a rim at or near the outer periphery of the annular body.

In some configurations, the ledge is substantially perpendicular to the bearing rotational axis.

In some configurations, at least the annular body comprises a silicone material.

Additionally, in accordance with certain features, aspects and advantages of at least one of the embodiments disclosed herein, a blower for an apparatus for delivering a flow of gas is disclosed, the blower comprising:
a casing,
an impeller,
a motor for driving the impeller, the motor including:
a rotatable shaft,
a rotor connected to the rotatable shaft, and
a stator,
a bearing arranged to allow rotation of the rotatable shaft relative to the casing, and
a bearing mount as disclosed above, wherein the bearing mount is arranged to support the bearing.

Additionally, in accordance with certain features, aspects and advantages of at least one of the embodiments disclosed herein, a blower for an apparatus for delivering a flow of gas is disclosed, the blower comprising:
a casing including a casing ledge and a flexible or resilient member,
a stator including a first stator ledge and a second stator ledge,
wherein the casing ledge supports the first stator ledge, and the flexible or resilient member supports the second stator ledge.

In some configurations, the blower further comprises:
a casing cap operatively connected to the casing, and
a vibration isolating member located between the stator and the casing cap arranged to bias the stator in a direction towards the first stator ledge.

In some configurations, the vibration isolating member is compressible.

In some configurations, the vibration isolating member is or comprises an elastomeric material.

In some configurations, the elastomeric material is silicone.

In some configurations, the flexible member is configured to flex beyond a periphery of the stator to allow removal of the stator from the casing.

Additionally, in accordance with certain features, aspects and advantages of at least one of the embodiments disclosed herein, a blower for an apparatus for delivering a flow of gas is disclosed, the blower comprising:
a casing including:
a casing cap, wherein the casing cap includes a collar defining a bearing mount recess arranged to receive a bearing mount,
wherein the bearing mount is arranged to support a bearing,
a motor chamber, wherein a first side of the motor chamber is defined by the casing cap, and a second side of the motor chamber is defined by a partition, wherein the partition is arranged to be connected to the casing cap, and wherein connection of the casing cap and the partition causes a preload force to be exerted on the bearing via the bearing mount.

In some configurations, the at least part of the bearing mount is arranged to flex or resiliently deform such that another part of the bearing mount moves in a direction generally parallel to the bearing rotational axis when the force is applied to the bearing mount.

In some configurations, at least part of the bearing mount is arranged to flex or resiliently deform when a force is applied to the bearing mount such that the force translated to the bearing retained in the central bore remains generally constant as the force applied to the bearing mount increases beyond a threshold.

In some configurations, at least part of the bearing mount is arranged to flex or resiliently deform such that another part of the bearing mount moves in a direction generally parallel to the bearing rotational axis when the force is applied to the bearing mount.

In some configurations, at least part of the bearing mount is arranged to flex or resiliently deform when a force is applied to the bearing mount such that the force translated to the bearing retained in the central bore remains generally constant as the force applied to the bearing mount increases beyond a threshold.

Additionally, in accordance with certain features, aspects and advantages of at least one of the embodiments disclosed herein, an apparatus for delivering a flow of gas is disclosed, the apparatus comprising:

a controller, a housing defining a gasflow passage, a motor with an impeller to deliver gas through the gasflow passage, a flexible printed circuit board electrically connected to the motor for electrically connecting the motor to the controller, and a sensor system, wherein the flexible printed circuit board also electrically connects the sensor system to the controller.

In some configurations, the flexible printed circuit board has signal tracks electrically connecting the sensor system to the controller and motor tracks electrically connecting the motor to the controller, wherein the signal tracks are positioned over the top of the motor tracks with a substrate between the signal tracks and motor tracks.

In some configurations, the flexible printed circuit board has signal tracks electrically connecting the sensor system to the controller and motor tracks electrically connecting the motor to the controller, wherein the signal tracks are positioned towards one side of the flexible printed circuit board and the motor tracks are positioned towards another side of the flexible printed circuit board with a substrate between the signal tracks and motor tracks.

In some configurations, the apparatus further comprises a space or gap formed in the substrate between the signal traces and the motor traces.

In some configurations, the apparatus further comprises a seal that provides a seal around the flexible printed circuit board where it exits the housing.

In some configurations, an end of the flexible printed circuit board is receivable by an edge connector of the controller.

In some configurations, the flexible printed circuit board has one or more stiffened regions to assist with attaching the flexible printed circuit board to other components.

Additionally, in accordance with certain features, aspects and advantages of at least one of the embodiments disclosed herein, an apparatus for delivering a flow of gas is disclosed, the apparatus comprising:

a controller, a sensor system, a housing defining a gasflow passage, a motor with an impeller to deliver gas through the gasflow passage, a flexible printed circuit board having a body and two branches extending from the body, one of the branches electrically connected to the motor for electrically connecting the motor to the controller, and the other of the branches electrically connected to the sensor system for electrically connecting the sensor system to the controller.

In some configurations, the flexible printed circuit board has signal tracks electrically connecting the sensor system to the controller and motor tracks electrically connecting the motor to the controller, wherein, at the body, the signal tracks are positioned towards one side of the flexible printed circuit board and the motor tracks are positioned towards another side of the flexible printed circuit board with a substrate between the signal tracks and motor tracks.

In some configurations, the apparatus further comprises a space or gap formed in the substrate between the signal traces and the motor traces.

In some configurations, the apparatus further comprises a seal that provides a seal around the flexible printed circuit board where it exits the housing.

In some configurations, an end of the flexible printed circuit board is receivable by an edge connector of the controller.

In some configurations, the flexible printed circuit board has one or more stiffened regions to assist with attaching the flexible printed circuit board to other components.

Additionally, in accordance with certain features, aspects and advantages of at least one of the embodiments disclosed herein, an apparatus for delivering a flow of gas is disclosed, the apparatus comprising: a housing defining a gasflow passage, a motor in the housing, the motor including a stator including a laminated stator core and windings, and a shield to pneumatically isolate the stator from the gasflow passage.

In some configurations, gas, which is or comprises oxygen, flows through the gasflow path.

In some configurations, gas is isolated from the stator.

In some configurations, the shield is a substantially annular component.

In some configurations, the shield is selectively removable.

In some configurations, the shield is a separately manufactured component that is later assembled with stator.

In some configurations, the stator is overmoulded with the shield, the shield comprising an overmould material.

In some configurations, the stator further includes one or more guards that insulate the windings from the stator core.

In some configurations, the guards are configured such that overmoulded material lies at least partially between the stator core and the windings.

In some configurations, the stator core comprises an annular portion and a plurality of stator teeth extending from the annular portion, the windings being wound around each of the stator teeth, each stator tooth having an inwardly facing tooth face.

In some configurations, the overmould material further covers the tooth faces of the stator teeth.

In some configurations, the one or more guards have retaining features for retaining the stator within a housing, and wherein the overmould material does not cover the retaining features.

In some configurations, the retaining features include a face of the guard that is configured to cooperate with one or more ledges and/or clips on the housing.

In some configurations, the retaining features are configured to prevent lateral and/or axial motion of the stator.

In some configurations, the overmould material covers all surfaces of the stator except for a portion of the guard or guards.

In some configurations, the motor further comprises an electrical connection on the stator, the electrical connection being at least partially covered by the overmould material.

In some configurations, the electrical connection is a PCB that is electrically connected to the windings.

In some configurations, the PCB is a flexible printed circuit, and wherein the flexible printed circuit includes a first portion connected to the windings and a second portion that extends from the motor, and wherein the first portion is covered by the overmould material.

In some configurations, the first portion is a stiffer section that the adjoining portion of the flexible printed circuit.

Additionally, in accordance with certain features, aspects and advantages of at least one of the embodiments disclosed herein, an apparatus for delivering a flow of gas is disclosed, the apparatus comprising:
a housing defining a gasflow passage, the gas flowing through the gasflow passage being a high concentration oxygen gas,
a motor including a stator including a laminated stator core and windings, and
an elastomeric shield to pneumatically isolate the windings from the gasflow passage.

Additionally, in accordance with certain features, aspects and advantages of at least one of the embodiments disclosed herein, an apparatus for delivering a flow of gas is disclosed, the apparatus comprising:
a controller,
a housing defining a gasflow passage,
a motor with an impeller to deliver gas through the gasflow passage,
a flexible printed circuit electrically connected to the motor for electrically connecting the motor to the controller.

In some configurations, the apparatus further comprises a sensor system, wherein the flexible printed circuit also electrically connects the sensor system to the controller.

Optionally in some configurations, the flexible printed circuit has signal traces electrically connects the sensor system to the controller and motor traces electrically connecting the motor to the controller, wherein the signal traces are positioned over the top of the motor traces with a substrate between the sensor traces and motor traces.

In some configurations, the flexible printed circuit has signal traces electrically connecting the sensor system to the controller and motor traces electrically connecting the motor to the controller, wherein the signal traces are positioned towards one side of the flexible printed circuit and the motor traces are positioned towards another side of the flexible printed circuit with a substrate between the signal traces and motor traces. Optionally a portion of substrate may be provided or may be present between the motor traces and the signal traces. A portion of substrate may be located between the adjacent motor traces. Adjacent motor traces may be disposed on separate layers of the flexible printed circuit. Alternatively an air gap may be located between motor traces and/or the signal traces that are disposed on the same layer of the printed circuit board.

In some configurations, the apparatus further comprises a seal that provides a seal around the flexible printed circuit where it exits the housing.

In some configurations, an end of the flexible printed circuit is receivable by an edge connector of the controller.

In some configurations, the flexible printed circuit has one or more stiffened regions to assist with attaching the flexible printed circuit to other components.

Additionally, in accordance with certain features, aspects and advantages of at least one of the embodiments disclosed herein, an apparatus for delivering a flow of gas is disclosed, the apparatus comprising:
a controller,
a sensor system,
a housing defining a gasflow passage,
a motor with an impeller to deliver gas through the gasflow passage,
a flexible printed circuit having a body and two branches extending from the body, one of the branches electrically connected to the motor for electrically connecting the motor to the controller, and the other of the branches electrically connected to the sensor system for electrically connecting the sensor system to the controller.

Optionally in some configurations, the flexible printed circuit has signal traces electrically connecting the sensor system to the controller and motor traces electrically connecting the motor to the controller, wherein, at the body, the signal traces are positioned over the top of the motor traces with a substrate between the signal traces and motor traces.

In some configurations, the flexible printed circuit has signal traces electrically connecting the sensor system to the controller and motor traces electrically connecting the motor to the controller, wherein, at the body, the signal traces are positioned towards one side of the flexible printed circuit and the motor traces are positioned towards another side of the flexible printed circuit. Optionally a substrate or a portion of substrate is positioned between the signal traces and motor traces.

In some configurations, the apparatus further comprises a seal that provides a seal around the flexible printed circuit where it exits the housing.

In some configurations, an end of the flexible printed circuit is receivable by an edge connector of the controller.

In some configurations, the flexible printed circuit has one or more stiffened regions to assist with attaching the flexible printed circuit to other components.

Additionally, in accordance with certain features, aspects and advantages of at least one of the embodiments disclosed herein, an apparatus for delivering a flow of gas is disclosed, the apparatus comprising:
a housing defining a gasflow passage,
an electrical component in the housing, and
an elastomeric shield to pneumatically isolate the electrical component from the gasflow passage.

In some configurations, the electrical component comprises a motor with windings and an impeller to deliver gas through the gasflow passage, wherein the windings of the motor are pneumatically isolated from the gasflow passage.

In some configurations, the shield is a substantially annular component.

In some configurations, the shield is selectively removable.

In some configurations, the shield is overmoulded with the electrical component.

In some configurations, the shield is a separately manufactured component that is later assembled with the electrical component.

In some configurations, gas that is or comprises oxygen flows through the gasflow path.

In some configurations, the gas is isolated from the electrical component.

Additionally, in accordance with certain features, aspects and advantages of at least one of the embodiments disclosed herein, an apparatus for delivering a flow of gas is disclosed, the apparatus comprising:

a housing defining a gasflow passage, the gas flowing through the gasflow passage being a high concentration oxygen gas, a motor with windings and an impeller to deliver gas through the gasflow passage, and an elastomeric shield to pneumatically isolate the windings from the gasflow passage. Features from one or more embodiments may be combined with features of one or more other embodiments. Additionally, more than one embodiment may be used together during a process of respiratory support of a patient.

In some configurations the elastomeric shield may be made from at least one of a thermoplastic, thermoset or silicone material.

In one configuration the elastomeric shield is formed from a PBT (polybutylene terephthalate) material.

In some configurations the PCB as described herein is a flexible printed circuit (FPC).

In some configurations the FPC as described herein is a multi-layer structure. In one exemplary configuration the FPC may include at least three layers each support a conductive track and three insulation layers, and one optional ground layer.

In some configurations the FPC may include flexible or weakened regions to allow for bending about at least one axis. In some configurations the flexible or weakened regions may allow for bending about 2 axes.

In some configurations the apparatus for delivering gas may include a grommet positioned on or adjacent or in contact with the FPC.

In some configurations the grommet provides a seal between components when assembled. The grommet is preferably coupled to a portion of the FPC. The grommet provides a seal where the FPC leaves the housing where the motor is located.

Additionally, in accordance with certain features, aspects and advantages of at least one of the embodiments disclosed herein, a blower for an apparatus for delivering a flow of gas is disclosed, the blower comprising:

a casing including at least one casing ledge and at least one flexible or resilient member, a stator including a first stator ledge and a second stator ledge, wherein the at least one casing ledge supports the first stator ledge, and the at least one flexible or resilient member supports the second stator ledge.

In some configurations, the blower further comprises:

a casing cap operatively connected to the casing, and a vibration isolating member located between the stator and the casing cap arranged to bias the stator in a direction towards the first stator ledge.

In some configurations, the vibration isolating member is compressible.

In some configurations, the vibration isolating member comprises an elastomeric material.

In some configurations, the elastomeric material is silicone.

In some configurations, the at least one flexible or resilient member is configured to flex beyond a periphery of the stator to allow removal of the stator from the casing.

In some configurations, the casing includes a top casing and a bottom casing, which engage around their respective peripheries, with a partition between the top casing and the bottom casing.

In some configurations, the bottom casing includes a casing cap.

In some configurations, the at least one casing ledge comprises a plurality of casing ledges located on the bottom casing and wherein the at least one flexible or resilient member comprises a plurality of flexible or resilient members located on the bottom casing.

In some configurations, each bottom casing ledge has a curved inner surface that substantially corresponds to a curve of the stator.

In some configurations, the plurality of casing ledges and the plurality of flexible or resilient members are integrally formed with the bottom casing.

Additionally, in accordance with certain features, aspects and advantages of at least one of the embodiments disclosed herein, a blower for an apparatus for delivering a flow of gas is disclosed, the blower comprising:

a casing including:

a casing cap, wherein the casing cap includes a collar defining a bearing mount recess arranged to receive a bearing mount, wherein the bearing mount is arranged to support a bearing, a motor chamber, wherein a first side of the motor chamber is defined by the casing cap, and a second side of the motor chamber is defined by a partition, wherein the partition is arranged to be connected to the casing cap, and wherein connection of the casing cap and the partition causes a preload force to be exerted on the bearing via the bearing mount.

In some configurations, at least part of the bearing mount is arranged to flex or resiliently deform such that another part of the bearing mount moves in a direction generally parallel to a bearing rotational axis when a force is applied to the bearing mount.

In some configurations, at least part of the bearing mount is arranged to flex or resiliently deform when a force is applied to the bearing mount such that a force translated to the bearing retained in a central bore remains generally constant as the force applied to the bearing mount increases beyond a threshold.

In some configurations, the partition is screwed to a bottom casing cap to secure one or more components of the blower in place, which in turn secures a bottom casing in place between the bottom casing cap and the partition, and the bottom casing is sandwiched between the bottom casing cap and the partition at its rim, sealing and preventing, or at least substantially inhibiting, airflow from an inlet aperture and volute into a motor assembly.

In some configurations, a bottom casing is secured to a top casing using a fastening mechanism.

In some configurations, a bottom casing cap includes fastening mechanisms that secure the bottom casing cap to the partition.

In some configurations, a bottom casing cap has an alignment feature that aligns with a protruding section of a bottom casing.

In some configurations, the blow further comprises a biasing component in a form of a modified bottom casing cap, the modified bottom casing cap having resilient fingers integrally formed with a bottom casing cap.

The term "comprising" as used in this specification means "consisting at least in part of". When interpreting each statement in this specification that includes the term "comprising", features other than that or those prefaced by the term may also be present. Related terms such as "comprise" and "comprises" are to be interpreted in the same manner.

It should be understood that alternative embodiments may comprise any or all combinations of two or more of the parts, elements or features illustrated, described or referred to in this specification.

This invention may also be said broadly to consist in the parts, elements and features referred to or indicated in the specification of the application, individually or collectively, and any or all combinations of any two or more said parts, elements or features.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting. Where specific integers are mentioned herein which have known equivalents in the art to which this invention relates, such known equivalents are deemed to be incorporated herein as if individually set forth.

BRIEF DESCRIPTION OF THE DRAWINGS

Specific embodiments and modifications thereof will become apparent to those skilled in the art from the detailed description herein having reference to the figures that follow, of which.

DETAILED DESCRIPTION OF SPECIFIC EMBODIMENTS

Figure 1:
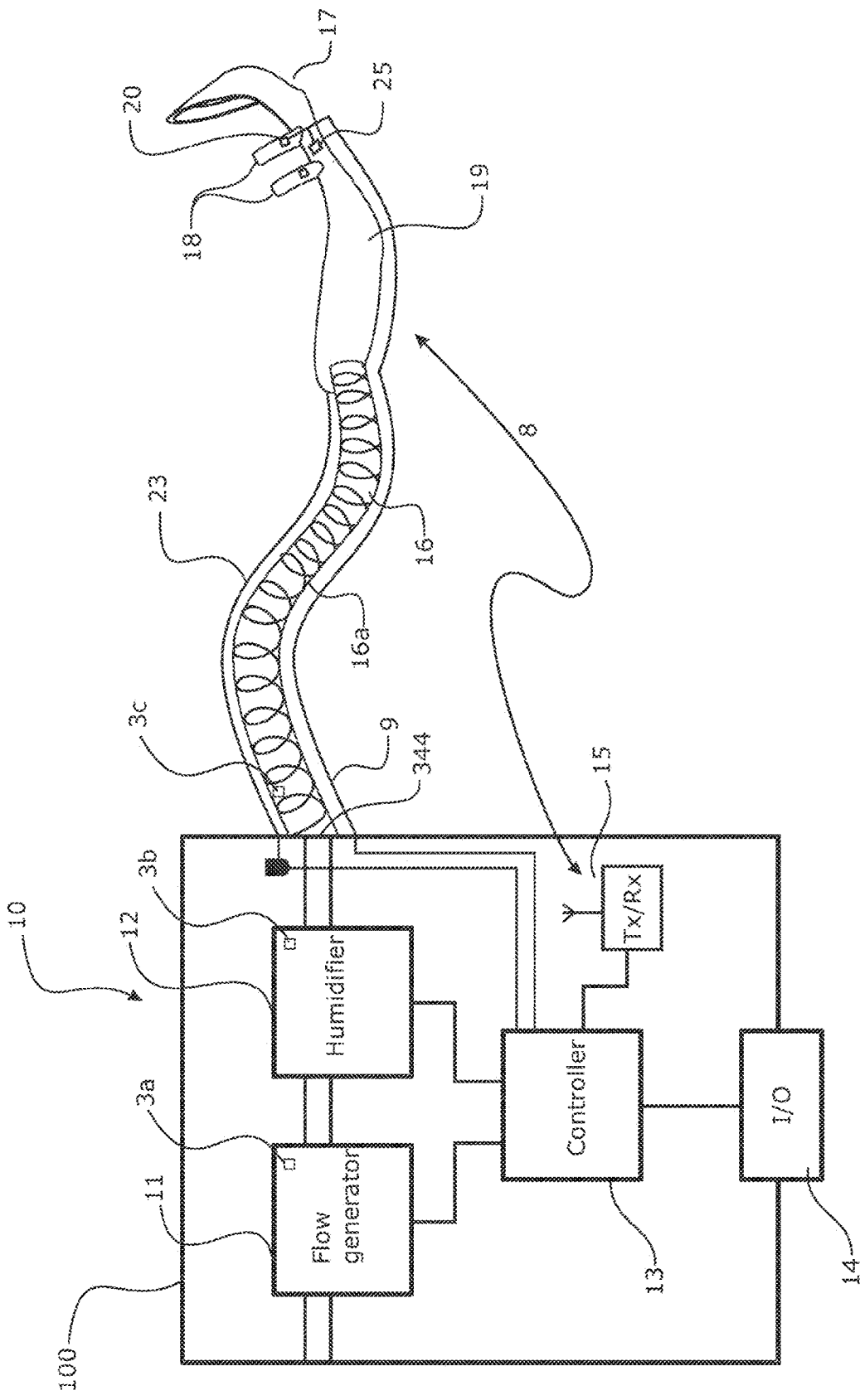
FIG. 1 shows in diagrammatic form a breathing assistance apparatus in the form of a flow therapy apparatus.
Figure 2:
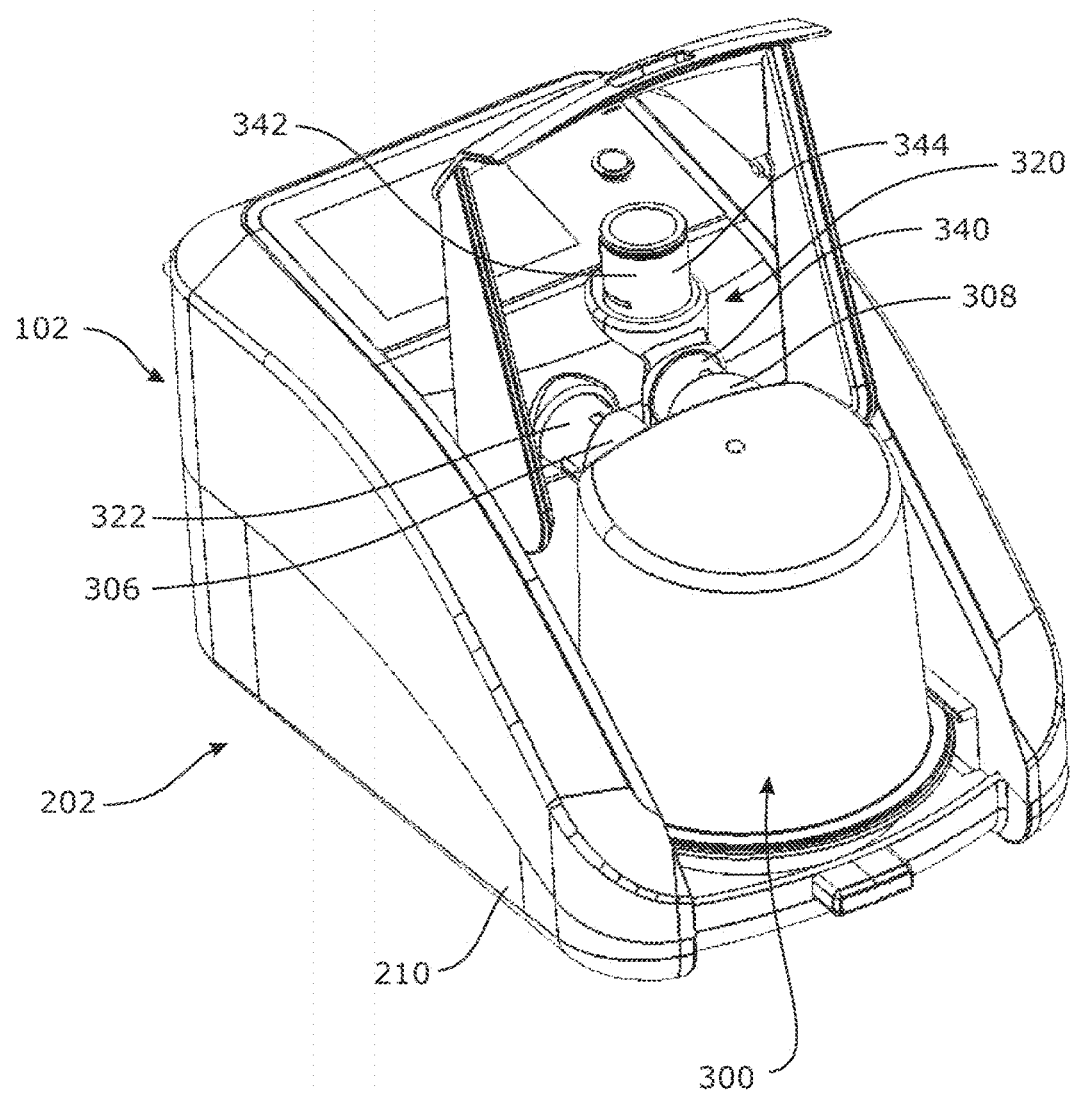
FIG. 2 is a perspective view of the flow therapy apparatus.
Figure 3:
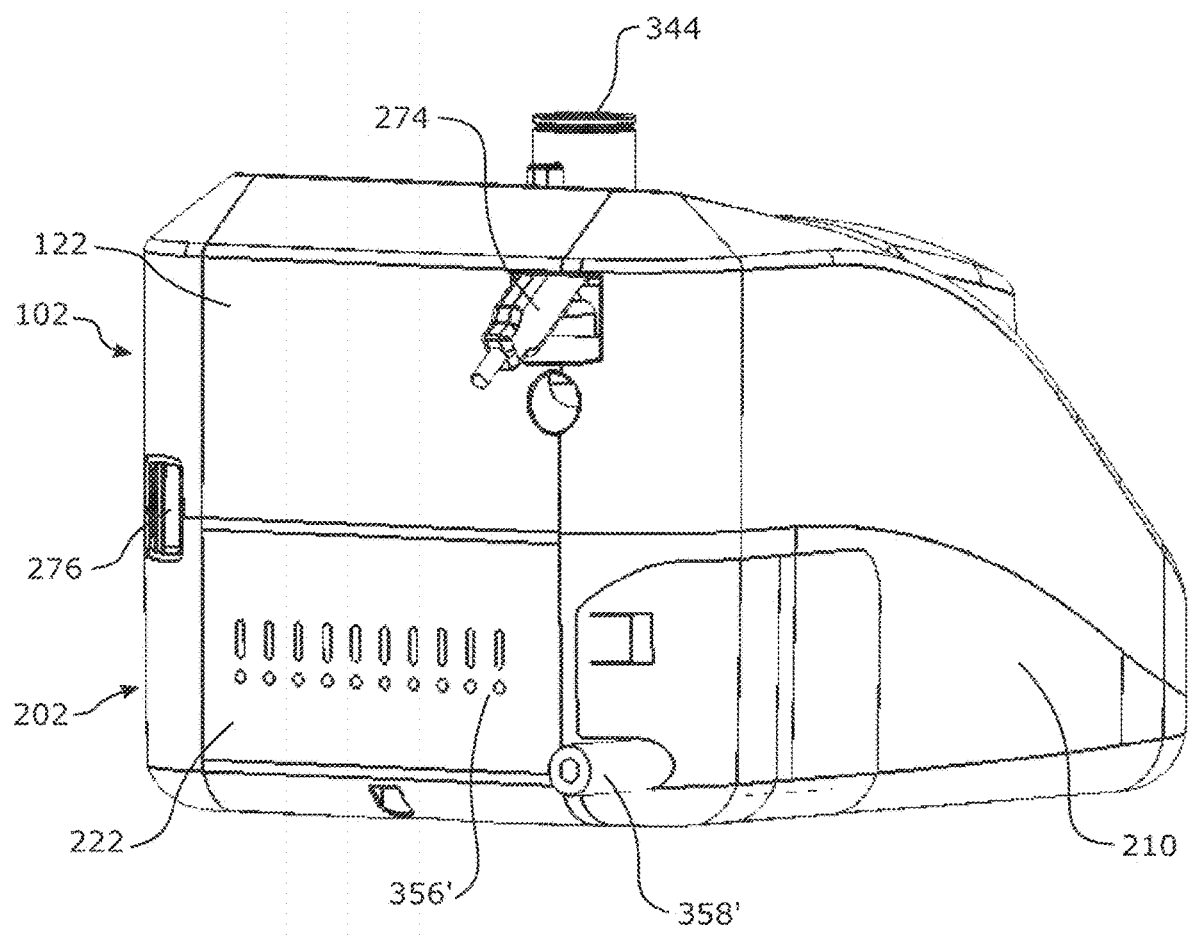
FIG. 3 shows a first configuration of an air and oxygen inlet arrangement of the flow therapy apparatus.
Figure 4:
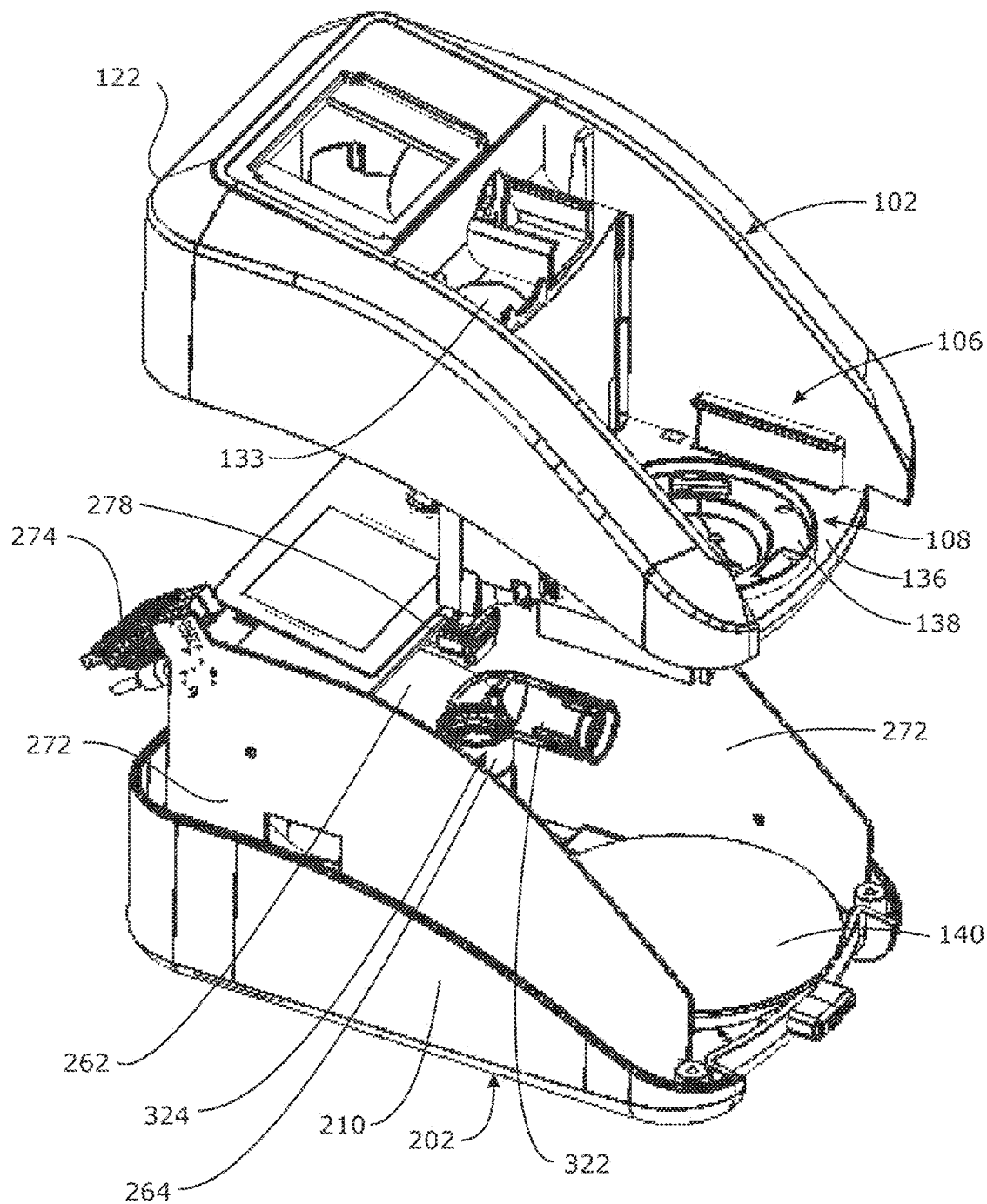
FIG. 4 is an exploded view of upper and lower chassis components of a main housing of the flow therapy apparatus.
Figure 5:
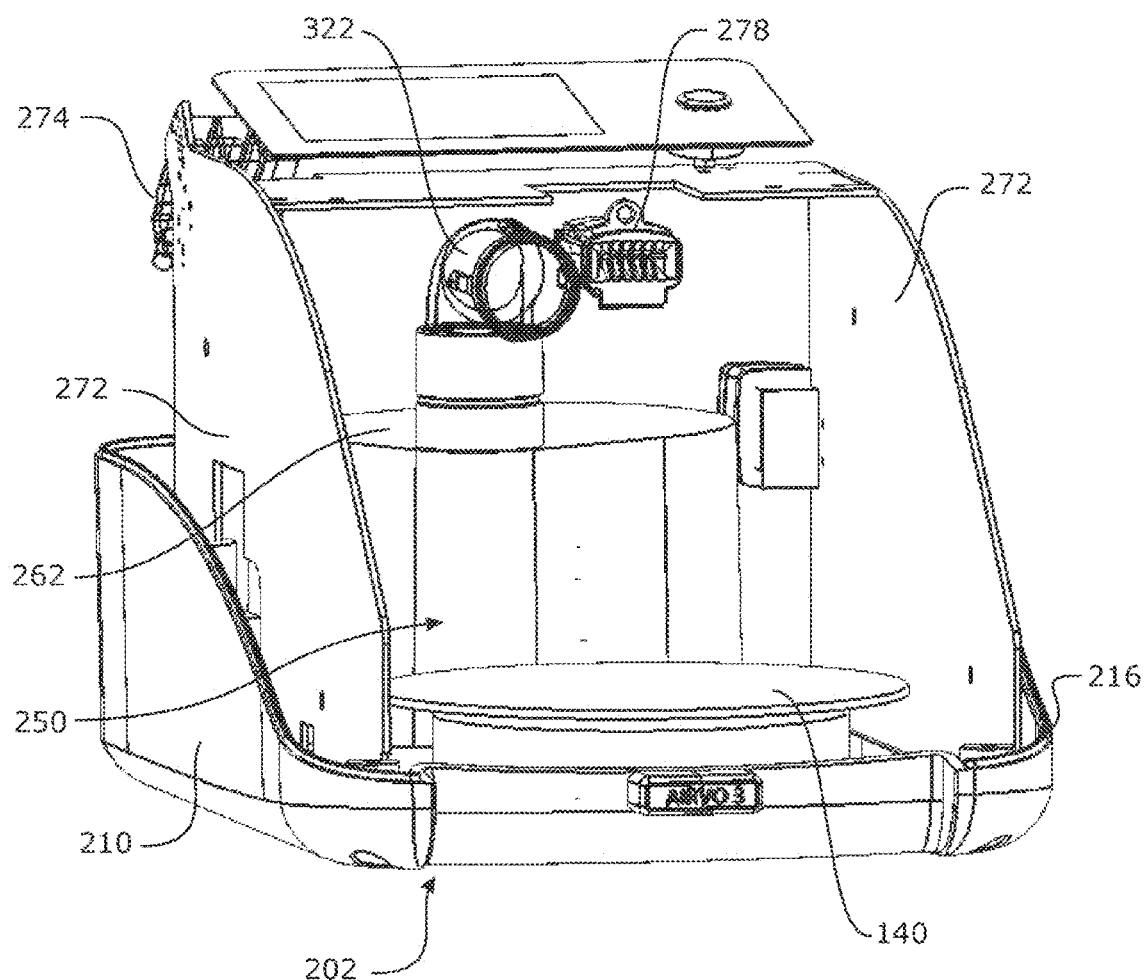
FIG. 5 is a front left side perspective view of the lower chassis of the main housing showing a housing for receipt of a motor and/or sensor module sub-assembly.
Figure 6:
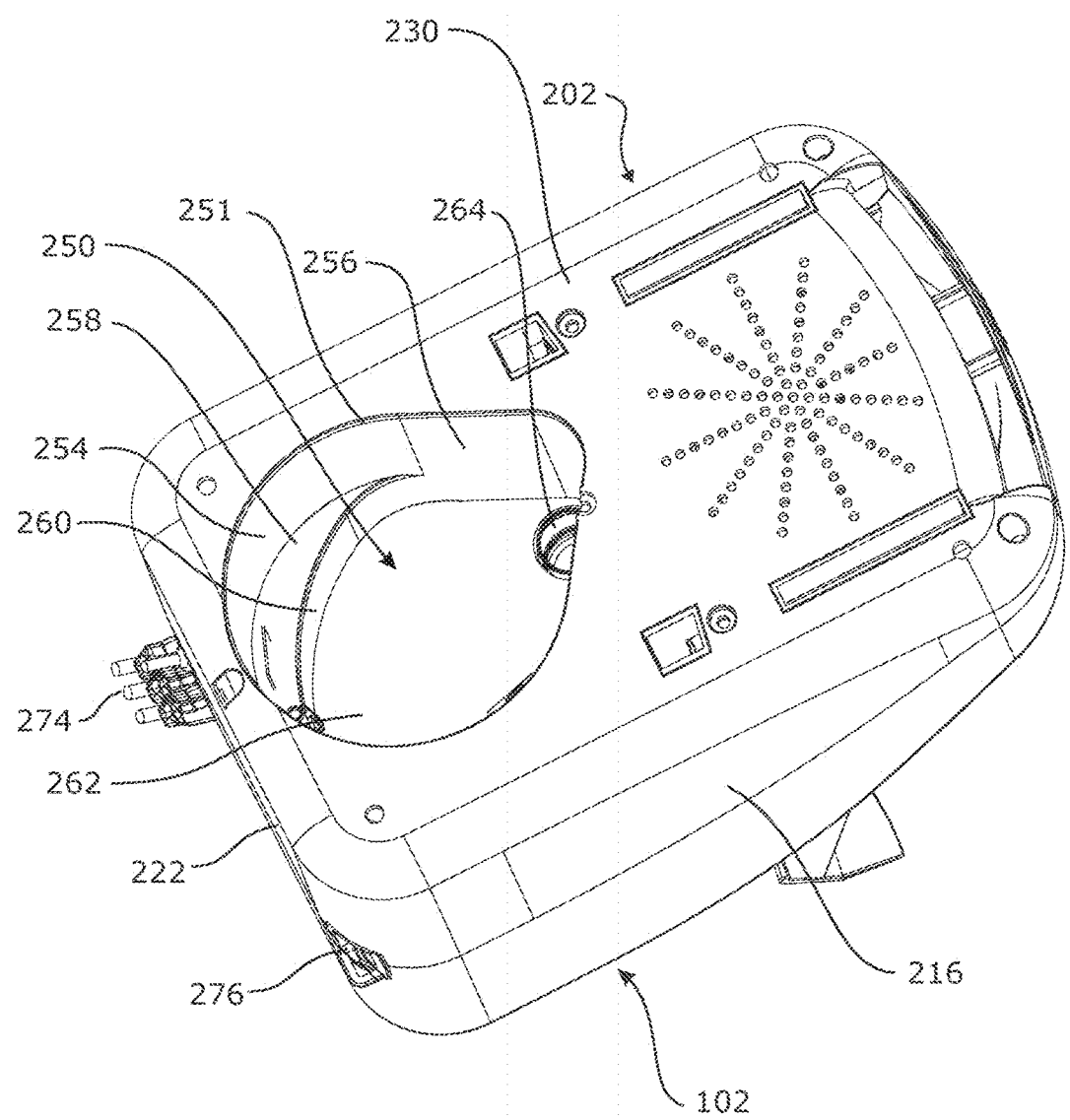
FIG. 6 is a first underside perspective view of the main housing of the flow therapy apparatus showing a recess inside the housing for the motor and/or sensor module sub-assembly.

A flow therapy apparatus 10 is shown in FIG. 1. In general terms, the apparatus 10 comprises a main housing 100 that contains a flow generator 11 in the form of a motor/impeller arrangement, an optional humidifier 12, a controller 13, and a user I/O interface 14 (comprising, for example, a display and input device(s) such as button(s), a touch screen, or the like). The controller 13 is configured or programmed to control the components of the apparatus, including: operating the flow generator 11 to create a flow of gas (gasflow) for delivery to a patient, operating the humidifier 12 (if present) to humidify and/or heat the generated gasflow, receive user input from the user interface 14 for reconfiguration and/or user-defined operation of the apparatus 10, and output information (for example on the display) to the user. The user could be a patient, healthcare professional, or anyone else interested in using the apparatus.

A patient breathing conduit 16 is coupled to a gasflow output 344 in the housing 100 of the flow therapy apparatus 10, and is coupled to a patient interface 17 such as a nasal cannula with a manifold 19 and nasal prongs 18. Additionally, or alternatively, the patient breathing conduit 16 could be coupled to a face mask. Additionally or alternatively, the patient breathing conduit could be coupled to a nasal pillows mask, and/or a nasal mask, and/or a tracheostomy interface, or any other suitable type of patient interface. The gasflow, which may be humidified, that is generated by the flow therapy apparatus 10 is delivered to the patient via the patient breathing conduit 16 through the cannula 17. The patient breathing conduit 16 can have a heater wire 16a to heat gasflow passing through to the patient. The heater wire 16a is under the control of the controller 13. The patient breathing conduit 16 and/or patient interface 17 can be considered part of the flow therapy apparatus 10, or alternatively peripheral to it. The flow therapy apparatus 10, breathing conduit 16, and patient interface 17 together form a flow therapy system.

General operation of a flow therapy breathing apparatus 10 will be known to those skilled in the art, and need not be described in detail here. However, in general terms the controller 13 controls the flow generator 11 to generate a gasflow of the desired flow rate, controls one or more valves to control the mix of air and oxygen or other alternative gas, and controls the humidifier 12 if present to humidify the gasflow and/or heat the gasflow to an appropriate level. The gasflow is directed out through the patient breathing conduit 16 and cannula 17 to the patient. The controller 13 can also control a heating element in the humidifier 12 and/or the heating element 16a in the patient breathing conduit 16 to heat the gas to a desired temperature that achieves a desired level of therapy and/or comfort for the patient. The controller 13 can be programmed with or can determine a suitable target temperature of the gasflow.

Operation sensors 3a, 3b, 3c, 20, 25 such as flow, temperature, humidity, and/or pressure sensors can be placed in various locations in the flow therapy apparatus 10 and/or the patient breathing conduit 16 and/or cannula 17. Output from the sensors can be received by the controller 13, to assist it to operate the flow therapy apparatus 10 in a manner that provides optimal therapy. In some configurations, providing optimal therapy includes meeting a patient's inspiratory demand. The apparatus 10 may have a transmitter and/or receiver 15 to enable the controller 13 to receive 8 signals from the sensors and/or to control the various components of the flow therapy apparatus 10, including but not limited to the flow generator 11, humidifier 12, and heater wire 16a, or accessories or peripherals associated with the flow therapy apparatus 10. Additionally, or alternatively, the transmitter and/or receiver 15 may deliver data to a remote server or enable remote control of the apparatus 10.

The flow therapy apparatus 10 may comprise a high flow therapy apparatus. As used herein, "high flow" therapy refers to administration of gas to the airways of a patient at a relatively high flow rate that meets or exceeds the peak inspiratory demand of the patient. The flow rates used to achieve "high flow" may be any of the flow rates listed below. For example, in some configurations, for an adult patient 'high flow therapy' may refer to the delivery of gases to a patient at a flow rate of greater than or equal to about 10 litres per minute (10 LPM), such as between about 10 LPM and about 100 LPM, or between about 15 LPM and about 95 LPM, or between about 20 LPM and about 90 LPM, or between about 25 LPM and about 85 LPM, or between about 30 LPM and about 80 LPM, or between about 35 LPM and about 75 LPM, or between about 40 LPM and about 70 LPM, or between about 45 LPM and about 65 LPM, or between about 50 LPM and about 60 LPM. In some configurations, for a neonatal, infant, or child patient 'high flow therapy' may refer to the delivery of gases to a patient at a flow rate of greater than 1 LPM, such as between about 1 LPM and about 25 LPM, or between about 2 LPM and about 25 LPM, or between about 2 LPM and about 5 LPM, or between about 5 LPM and about 25 LPM, or between about 5 LPM and about 10 LPM, or between about 10 LPM and about 25 LPM, or between about 10 LPM and about 20 LPM, or between about 10 LPM and 15 LPM, or between about 20 LPM and 25 LPM. A high flow therapy apparatus with an adult patient, a neonatal, infant, or child patient, may deliver gases to the patient at a flow rate of between about 1 LPM and about 100 LPM, or at a flow rate in any of the sub-ranges outlined above. Gases delivered may comprise a percentage of oxygen. In some configurations, the percentage of oxygen in the gases delivered may be between about 20% and about 100%, or between about 30% and about 100%, or between about 40% and about 100%, or between about 50% and about 100%, or between about 60% and about 100%, or between about 70% and about 100%, or between about 80% and about 100%, or between about 90% and about 100%, or about 100%, or 100%.

As used herein, a 'high concentration oxygen gas' is a gas in which air may be supplemented with oxygen.

High flow therapy has been found effective in meeting or exceeding the patient's inspiratory demand, increasing oxygenation of the patient and/or reducing the work of breathing. Additionally, high flow therapy may generate a flushing effect in the nasopharynx such that the anatomical dead space of the upper airways is flushed by the high incoming gas flows. This creates a reservoir of fresh gas available of each and every breath, while minimising re-breathing of carbon dioxide, nitrogen, etc.

The patient interface may be a non-sealing interface to prevent barotrauma (e.g. tissue damage to the lungs or other organs of the respiratory system due to difference in pressure relative to the atmosphere). The patient interface may be a nasal cannula with a manifold and nasal prongs, and/or a face mask, and/or a nasal pillows mask, and/or a nasal mask, and/or a tracheostomy interface, or any other suitable type of patient interface.

As shown in FIGS. 2 to 23 and described below, the flow therapy apparatus 10 has various features to assist with the functioning, use, and/or configuration of the apparatus 10.

As shown in FIGS. 2 to 8, the flow therapy apparatus 10 comprises a main housing 100. The main housing 100 has a main housing upper chassis 102 and a main housing lower chassis 202.

The main housing upper chassis 102 has a peripheral wall arrangement 106. The peripheral wall arrangement defines a humidifier or liquid chamber bay 108 for receipt of a removable liquid chamber 300. The removable liquid chamber 300 contains a suitable liquid such as water for humidifying gases that will be delivered to a patient. A floor portion 136 of the liquid chamber bay 108 has a recess 138 to receive a heater arrangement such as a heater plate 140 or other suitable heating element(s) for heating liquid in the liquid chamber 300 for use during a humidification process.

As shown in FIGS. 6 to 15, the lower chassis 202 has a motor recess 250 having a recess opening 251 for receipt of a motor and/or sensor module 400, which is described in further detail below. In other embodiments, the motor may not be removable. A continuous, gas impermeable, unbroken peripheral wall 252 is integrally formed with the bottom wall 230 of the lower chassis 202 and extends upwardly from the periphery of the opening 251. The tube 264 forming the gasflow passage is integrally formed with the ceiling 262, with the ceiling surrounding and extending outwardly from the tube 264. Therefore, the entire motor recess 250 is gas impermeable and unbroken, other than the gasflow passage.

The tube 264 forming the gasflow passage extends upwardly through a downward outer extension tube or conduit 133 that is integrally formed with the upper housing chassis 102. A soft seal such as an O-ring seal (not shown) is located between the exterior of the gasflow passage tube 264 and the interior of downward outer extension tube or conduit 133, to provide a seal between the components when assembled. In other configurations, the gasflow passage tube 264 and the downward extension tube 133 could be configured to be fitted together via other arrangements while still providing for a seal between the components when assembled.

The configuration is such that if there is any leaking of gas from the motor or gasflow path following the motor via any seals, the gas will vent to atmosphere rather than ingressing into the interior of the main housing that contains the control boards and other electrical components as described below. The electrical components and electronics boards in the housing are pneumatically isolated from the gasflow path. The only way for gas to leak into the portion of the main housing 100 that contains the electronics boards and other electrical components will be if there is a physical crack in the housing 100 or another physical component In the motor and/or sensor module 400, the pressure is lower before/upstream of the motor impeller, and the pressure is higher after/downstream of the motor impeller. An electrical connection will be provided for the motor upstream of the motor impeller, in the lower pressure region. If there is a failure in the housing in the portion near the electrical connection, air will be sucked into the low pressure side.

In an alternative configuration, the motor recess comprising items 252, 254, 256, 258, 260, 264 may be separately formed from the lower chassis 202. The motor assembly including the recess may be insertable into the recess opening 251 and attachable to the lower chassis 202. Upon insertion of the motor and/or sensor module 400 and recess into the lower chassis 202, the gasflow passage tube 264 will extend through the downward extension tube 133 and be sealed by the soft seal.

In the form shown, the recess 250 comprises a recess opening in a bottom wall of the housing. Alternatively, the recess opening could be in a different part of the housing, such as a side, front, or top of the housing.

The described configuration provides a chamber shaped to receive a motor and/or sensor module 400 as described below with reference to FIGS. 9 and 10. The motor may be a removable motor or a non-removable or fixed motor. The interior wall of the recess 250 (including but not limited to portions of the peripheral wall 252) may be provided with guides and/or mounting features to assist with locating and/or attaching the module 400 in the recess 250. The motor and/or sensor module 400 comprises a flow generator 11 with an impeller 72001 that operates as a blower to deliver gases to the patient interface 17 via the liquid chamber 300. It will be appreciated that the shape of the chamber can vary depending on the shape of the motor and/or sensor module 400. However, the chamber will be provided with continuous, gas impermeable, and unbroken walls and a ceiling to isolate the gasflow from electrical and electronic components in the main housing 100.

Figures 17, 18:
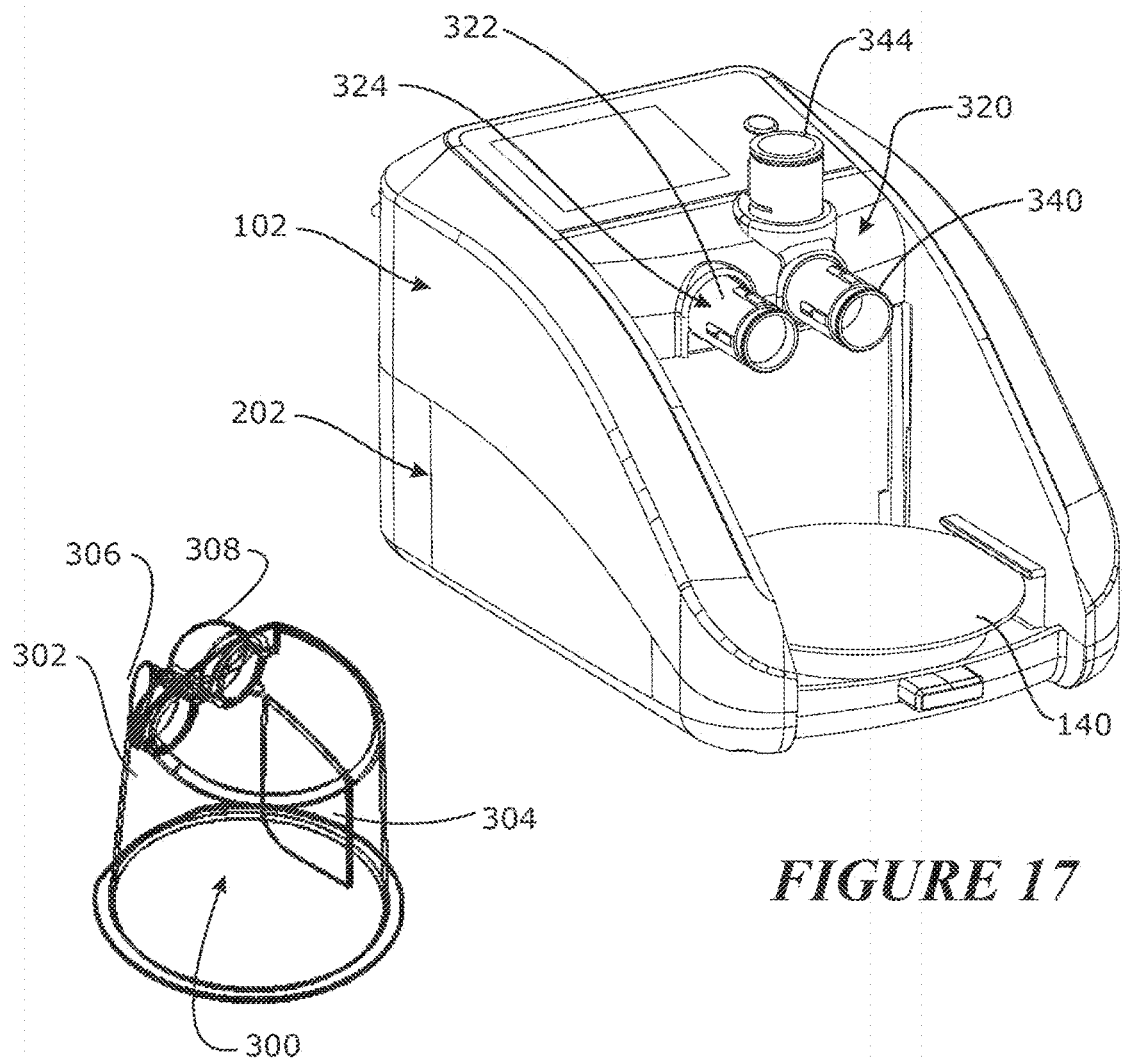
FIG. 17 is a front left side perspective view of some of the components of the flow therapy apparatus.
FIG. 18 is a front left side perspective view of a liquid chamber for use in the flow therapy apparatus.

With reference to FIG. 18, the removable liquid chamber 300 comprises an outer housing 302 defining a liquid reservoir, a liquid chamber gases inlet port 306 in fluid communication with the liquid reservoir, and a liquid chamber gases outlet port 308 in fluid communication with the liquid reservoir. A baffle 304 is provided internally in the liquid reservoir to define a flow path of gases through the liquid chamber 300.

The apparatus 10 comprises a connection arrangement 320 for fluid coupling of the liquid chamber 300 to the apparatus 10. The connection arrangement 320 comprises a gases outlet port 322 that is in fluid communication, via a fixed L shaped elbow 324, with the gasflow passage from the flow generator 11.

The connection arrangement 320 further comprises a gases inlet port 340 (humidified gases return) that is embodied in a removable elbow 342. The removable elbow 342 has a patient outlet port 344 for coupling to the patient breathing conduit 16 to deliver gases to the patient interface 17. The gases outlet port 322, gases inlet port 340, and patient outlet port 344 each comprise soft seals such as O-ring seals (not shown) to provide a sealed gases passageway between the apparatus 10, the liquid chamber 300, and the patient breathing conduit 16.

The apparatus 10 has air and oxygen (or alternative auxiliary gas) inlets in fluid communication with the flow generator 11 to enable the flow generator 11 to deliver air, oxygen (or alternative auxiliary gas), or a suitable mixture thereof to the liquid chamber 300 and thereby to the patient. In some configurations, the gas comprises a blend of oxygen and ambient air. The apparatus 10 may have the arrangement shown in FIG. 3 to enable the flow generator 11 to deliver air, oxygen (or alternative auxiliary gas), or a suitable mixture thereof to the liquid chamber 300 and thereby to the patient. This arrangement comprises an air inlet 356' in the rear wall 222 of the lower chassis 202 of the housing 100. An air filter box is positioned adjacent the air inlet 356' internally in the main housing 100, and comprises an air outlet port to deliver filtered air to the flow generator 11 via an air inlet port in the motor and/or sensor module 400. The air filter box 354' may comprise a filter configured to remove particulates (e.g. dust) and/or pathogens (e.g. viruses or bacteria) from the gasflow. A soft seal such as an O-ring seal will be provided between the air outlet port and air inlet port to seal between the components. The apparatus 10 comprises a separate oxygen inlet port 358' positioned adjacent one side of the housing 100 at a rear end thereof, the oxygen port 358' for receipt of oxygen from an oxygen source such as a tank or source of piped oxygen. The oxygen inlet port 358' is in fluid communication with a proportional oxygen valve 362. The oxygen valve 362 will suitably be a solenoid valve that enables the control of the amount of oxygen that is added to the gasflow that is delivered to the liquid chamber 300. It should be understood that in alternative configurations the oxygen port 358' and proportional oxygen valve 362 may be used with other auxiliary gases to control the addition of other auxiliary gases to the gasflow. The other auxiliary gases may comprise any one or more of a number of gases useful for gas therapy, including but not limited to heliox and nitric oxide.

As shown in FIGS. 4, 5, 15, and 16, the lower housing chassis 202 carries suitable electronics boards 272 such as printed circuit boards. The electronics boards are positioned adjacent respective outer side walls 210, 216 of the lower housing chassis 202. The electronics boards 272 contain, or are in electrical communication with, suitable electrical or electronics components such as but not limited to microprocessors, capacitors, resistors, diodes, operational amplifiers, comparators, and switches. Sensors may be used. Components of the electronics boards 272 (such as but not limited to one or more microprocessors) act as the controller 13 of the apparatus.

One or both of the electronics boards 272 are in electrical communication with the electrical components of the apparatus 10, including the display unit and user interface 14, flow generator 11, oxygen valve 362, and the heater plate 140 to operate the flow generator 11 to provide the desired flow rate of gas, operate the humidifier 12 to humidify and heat the gasflow to an appropriate level, and supply appropriate quantities of oxygen (or in alternative configurations quantities of an alternative auxiliary gas) to the gasflow.

The electronics boards 272 are in electrical communication with a connector arrangement 274 projecting from the rear wall 122 of the upper housing chassis 102. The connector arrangement 274 may be coupled to a nurse alarm, pulse oximetry port, and/or other suitable accessories. The electronics boards 272 are also in electrical communication with an electrical connector 276 that is also provided in the rear wall 122 of the upper housing chassis 102 to provide mains or battery power to the components of the apparatus 10. The electronics boards 272 are also in electrical communication with an electrical connector 278 for the removable elbow 342.

As mentioned above, operation sensors, such as flow, temperature, humidity, and/or pressure sensors can be placed in various locations in the flow therapy apparatus 10 and/or the patient breathing conduit 16 and/or cannula 17. The electronics boards 272 will be in electrical communication with those sensors. Output from the sensors can be received by the controller 13, to assist the controller 13 to operate the flow therapy apparatus 10 in a manner that provides optimal therapy, including meeting inspiratory demand.

As outlined above, the electronics boards 272 and other electrical and electronic components are pneumatically isolated from the gasflow path, thereby reducing or avoiding any explosion risk that could otherwise occur if there was not that isolation.

Various aspects of the device will now be described in more detail.

FIGS. 9 to 16 show the motor and/or sensor module or sub-assembly 400 in greater detail.

Figure 9:
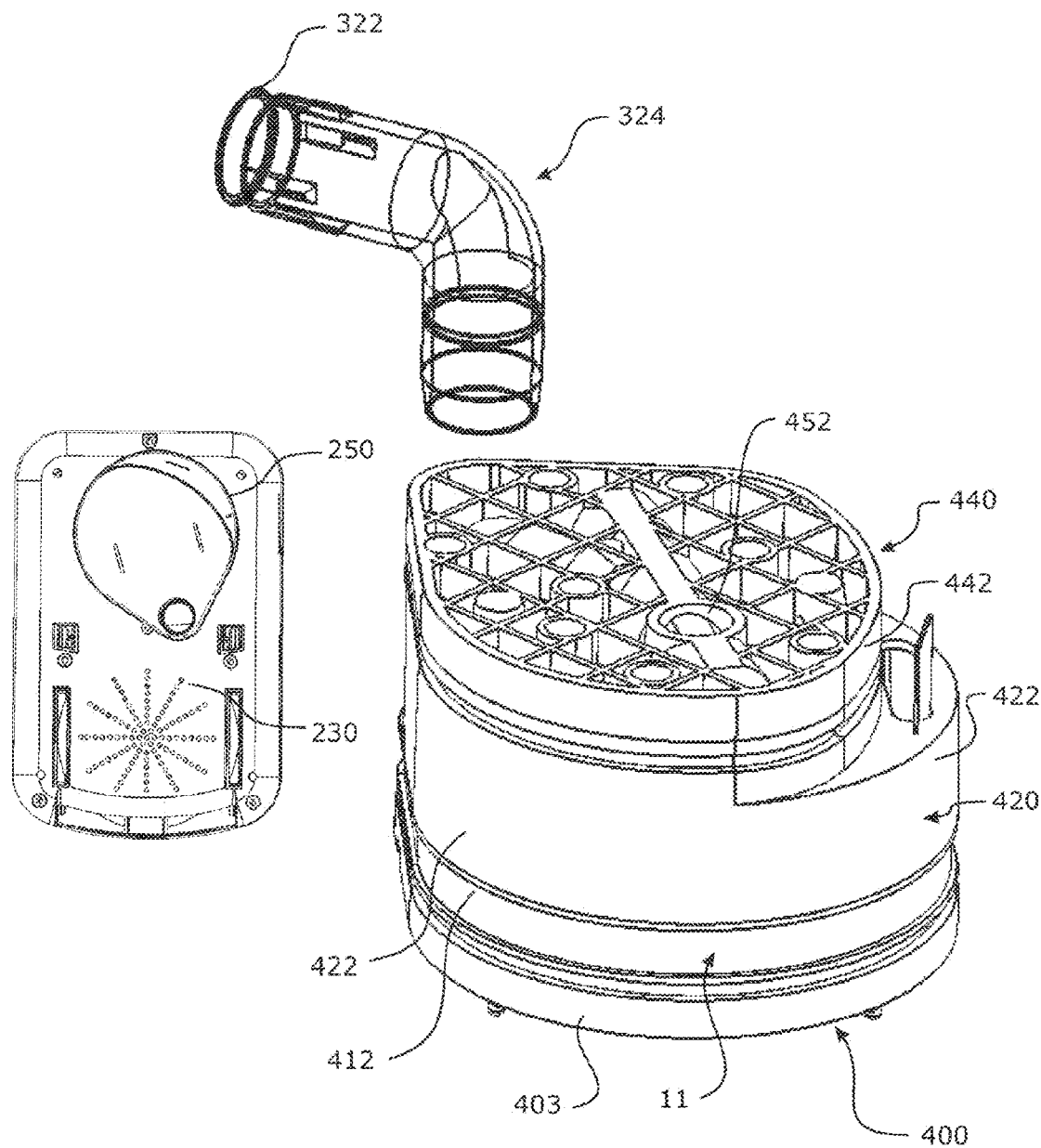
FIG. 9 is a perspective view of the motor and/or sensor sub-assembly, underside of the main housing, and a fixed elbow of the flow therapy apparatus.
Figure 10:
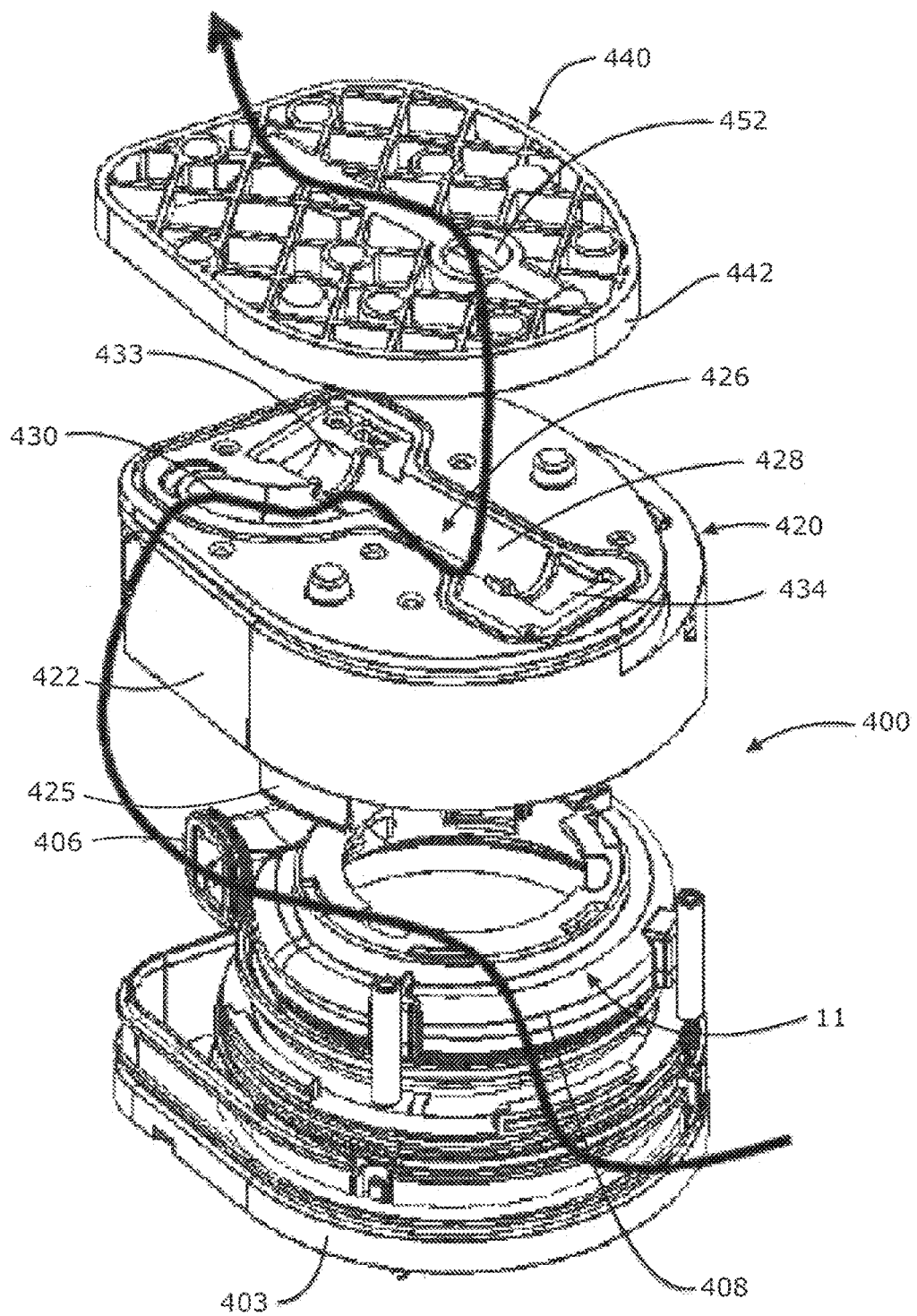
FIG. 10 is an exploded perspective view of components of the motor and/or sensor sub-assembly schematically showing by way of an arrow the gasflow path through the sub-assembly.
Figure 11:
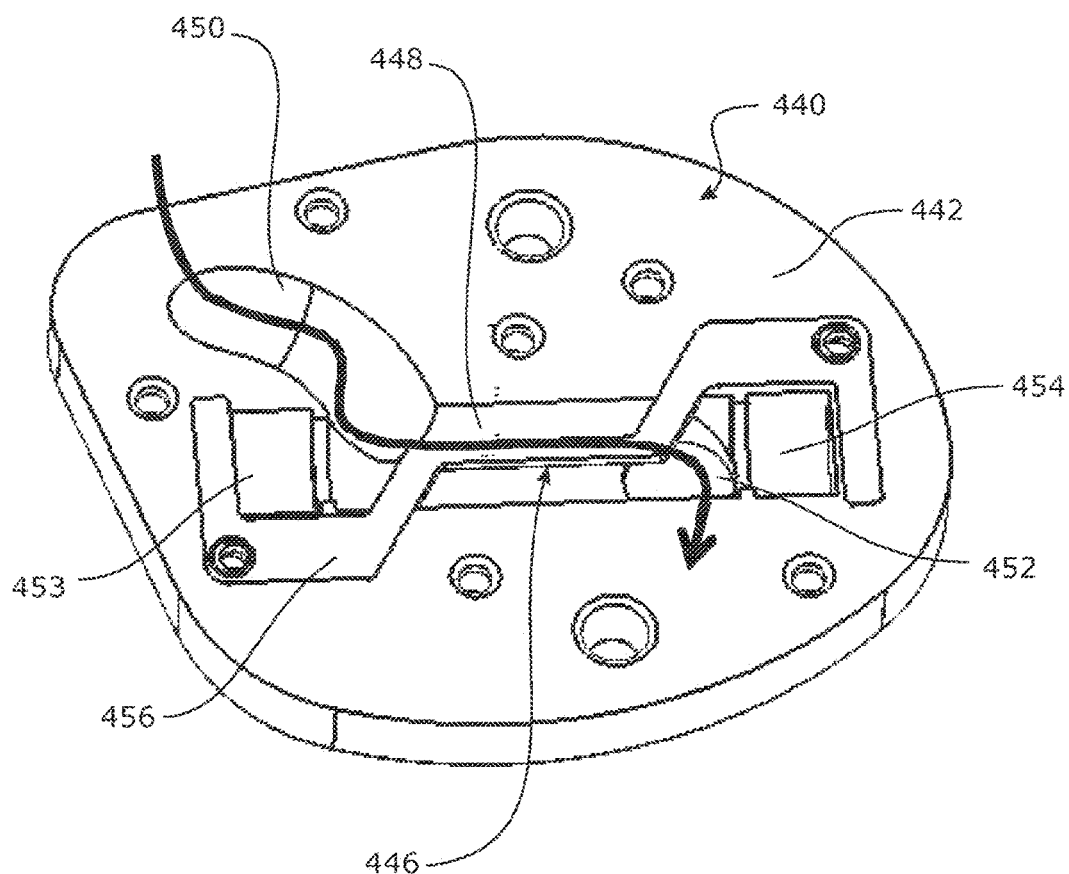
FIG. 11 is an underside view of a cover and sensing PCB of the motor and/or sensor sub-assembly showing the position of sensors.

In the form shown in FIGS. 9 to 11, the motor and/or sensor module 400 comprises a stacked arrangement of three main components; a base 403 of the sub-assembly 400 (on which is positioned the flow generator 11, which includes the motor 402), an outlet gasflow path and sensing layer 420 positioned above the base 403, and a cover layer 440. The base 403, the sensing layer 420, and the cover layer 440 assemble together to form a sub-assembly housing that has a shape that is complementary to that of the recess 250 so that the sub-assembly 400 can be received in the recess 250. The base 403 is configured to close the recess opening 251 when the sub-assembly 400 is positioned in the recess 250. The sub-assembly 400 may be maintained in position in the recess in any suitable way such as with fasteners, clips, or a quick release arrangement for example.

The sensing layer comprises a gasflow path with one or more sensors, the gasflow path arranged to deliver gas to the outlet port of the housing.

The flow generator (blower) 11 will now be described in more detail. The flow generator 11 has a body 408 that defines an impeller chamber that contains a motor 402 that drives an impeller 20031. The motor 402 could be any suitable gas blower motor, and may for example be a motor and impeller assembly of the type described in published PCT specification WO2013/009193 and shown in FIGS. 13A and 13B for example. The contents of that specification are incorporated herein in their entirety by way of reference.

The motor 402 is a brushless DC motor operated using sensorless vector control (also termed 'field oriented control') controlled by the electronics board 272, for example, via a flexible printed circuit (FPC) 10001, which is described in more detail below. The control can be tuned to suit a low inertia impeller. The central hub 20032 of the impeller 20031 is engaged with a shaft 20060 that extends from the motor 402. Mounted to the shaft is a plurality of, preferably small, magnetic segments to form a rotor 20062. In one embodiment the magnet is 20 mm in diameter, but more generally the diameter could be less than 20 mm and preferably between 10 mm to 15 mm. The magnet volume is less than 1600 mm$^3$ and can be between 500 mm$^3$ and 1600 mm$^3$. Surrounding the rotor 20062 is a laminated stator having a plurality of poles 20063 and windings 20068. The windings 20068 are selectively energised by the controller 13 via the FPC 10001 to facilitate rotation of the rotor, and therefore the shaft 20060 and impeller 20031, about the central axis defined by the centreline of the shaft 20060. In an alternate configuration, rather than an FPC, one or more rigid-flexible circuit/s or one or more flexible flat cable/s could be used.

A gases outlet 406 is in fluid communication with a gases inlet of the outlet gasflow path and sensing layer 420, which is stacked on top of the motor 402. This layer 420 comprises a body 422 which comprises a plurality of mounting legs 425 that can be inserted into a plurality of mounting slots (not shown) of the base 403 to secure the body 422 to the base 403. In other configurations, other structures or arrangements may be used to secure the body 422 to the base 403, including but not limited to fasteners, clips, or quick release arrangements. In one configuration, the body 422 defines a gasflow path that couples the gases outlet 406 with the gases inlet of the gasflow path and sensing layer 420. An alternative configuration such as but not limited to a coupling tube could be used to couple the gases outlet 406 with that gases inlet.

The body 422 defines a lower portion 426 of a sensing and gasflow path. The cover layer 440 has a body 442 that defines the upper portion 446 of the sensing and gasflow path, with the shape of the upper and lower portions 426, 446 corresponding substantially to each other.

As shown in FIGS. 10 and 11, the gasflow path comprises a linear elongate gasflow portion 428, 448. The inlet is in fluid communication with an entrance portion 430, 450 of the gasflow path, which is located at or adjacent an entrance end of the linear elongate portion 428, 448 of the gasflow path. Recesses 433, 453 and 434, 454 may be provided at opposite ends of the linear elongate portion of the gasflow path.

Figure 7:
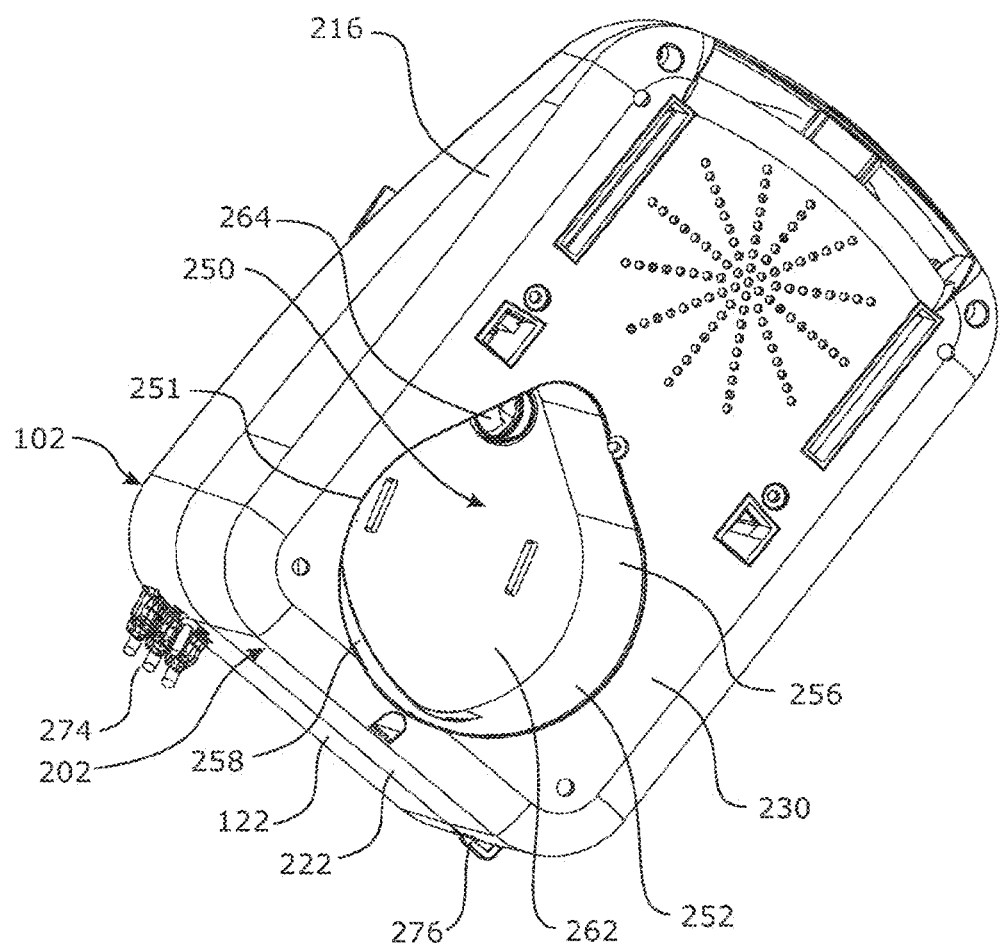
FIG. 7 is a second underside perspective view of the main housing of the flow therapy apparatus showing the recess for the motor and/or sensor module sub-assembly.
Figure 8:
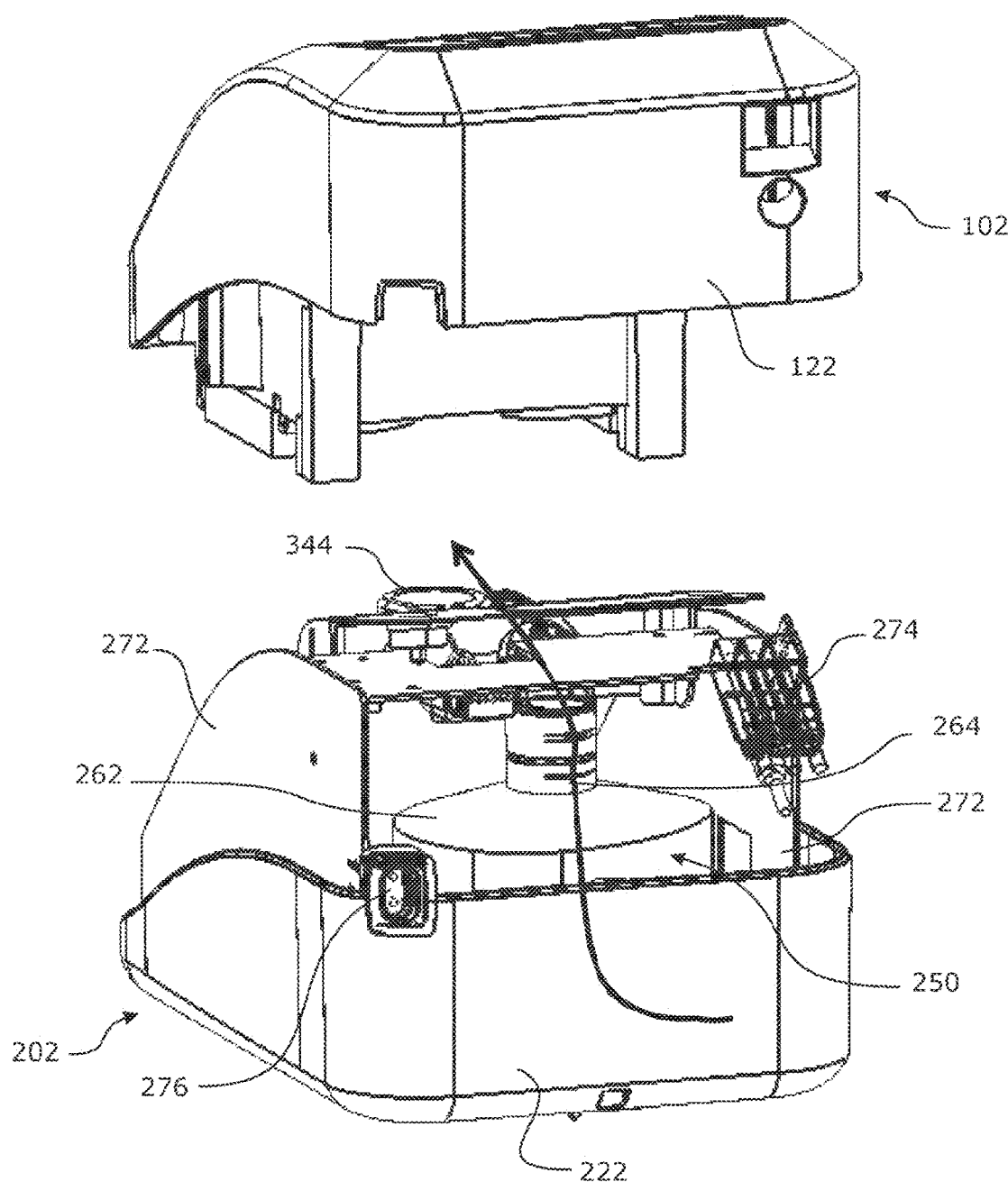
FIG. 8 is an exploded rear perspective view schematically showing by way of an arrow the gasflow path through the flow therapy apparatus.

A gasflow outlet port 452 extends vertically through the body 442 of the cover layer 440, and is located at or adjacent an opposite exit end of the linear elongate portion 428, 448 of the gasflow path. The gas outlet port 452 is in fluid communication with an upper portion of the motor recess 250, which in turn is in fluid communication with the gasflow passage. Again, due to the wall 252 and ceiling 262 configuration of the recess 250, if there is gas leakage from the motor/sensor module 400, that will be vented to atmosphere rather than entering the portion of the main housing 100 that contains the bulk of the electronics and control equipment. The recess 250 may comprise spacer(s), such as lugs that protrude downwardly from ceiling 262 as shown in FIG. 7, to maintain a suitable spacing for gasflow from the gas outlet port 452 and the ceiling of the recess 262.

It can be seen from FIG. 10 that at least part of the gasflow path through and out of the motor and/or sensing module 400 has a tortuous or sinuous configuration.

As shown in FIG. 11, the cover layer 440 comprises a sensing printed circuit board (PCB) 456. The cover layer 440 may also comprise one or more temperature sensors such as thermistors that sit in the elongate portion 428, 448 of the gasflow path. One sensor will measure gas temperature and the other can act as a redundant temperature sensor. Alternatively, one of the thermistors could be used as a reference flow sensor (e.g. via use as a constant-temperature thermistor), and the measured temperatures could be used to determine the gasflow rate through the portion 428, 448 of the gasflow path. The one or more temperature sensors may be located on a portion of the sensing PCB 456 that faces the gasflow. The sensing PCB 456 may additionally comprise other sensors including but not limited to pressure sensors, humidity sensors and dew point sensors.

Figure 12:
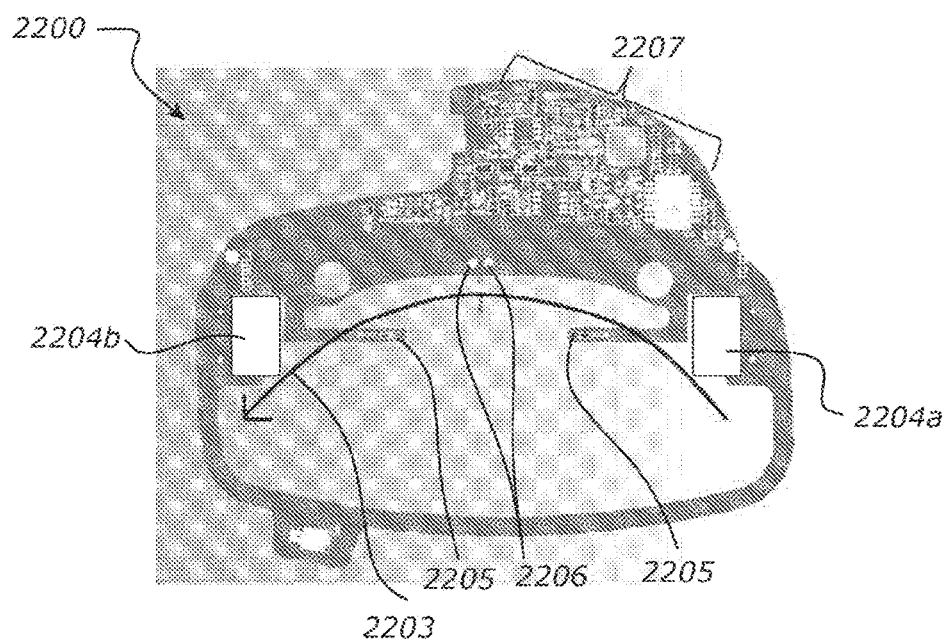
FIG. 12 shows an alternative embodiment of a sensing PCB.
Figure 13A:
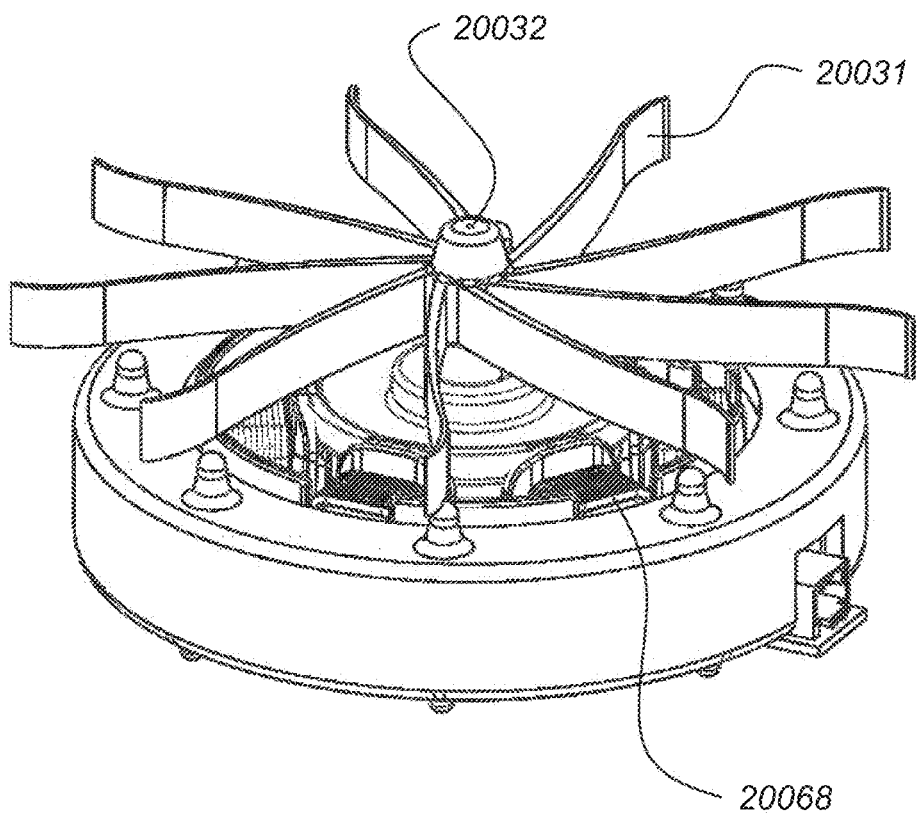
FIG. 13A shows a perspective view of the motor and impeller.
Figure 13B:
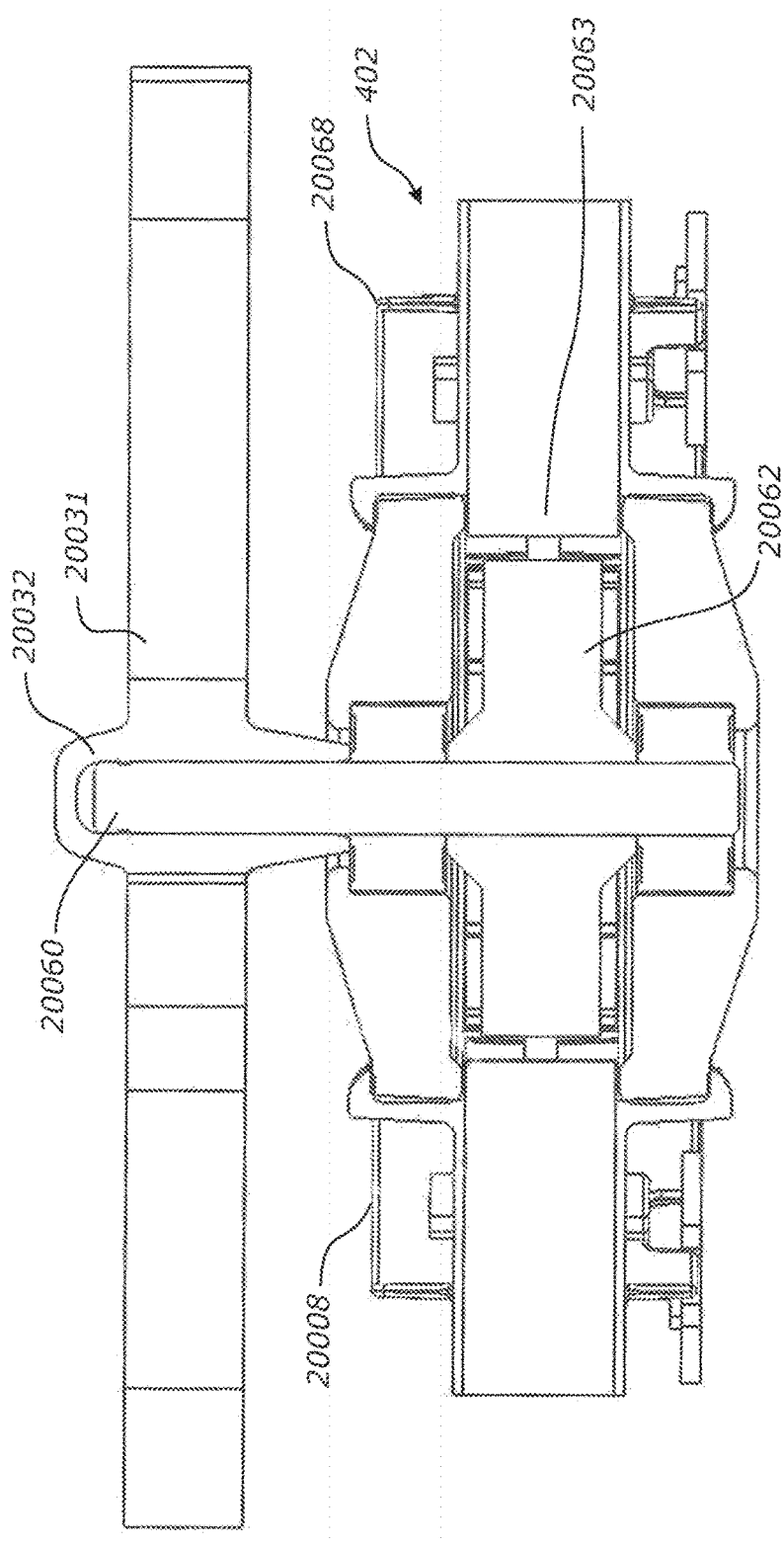
FIG. 13B shows a cross sectional view of the motor and impeller.
Figure 14:
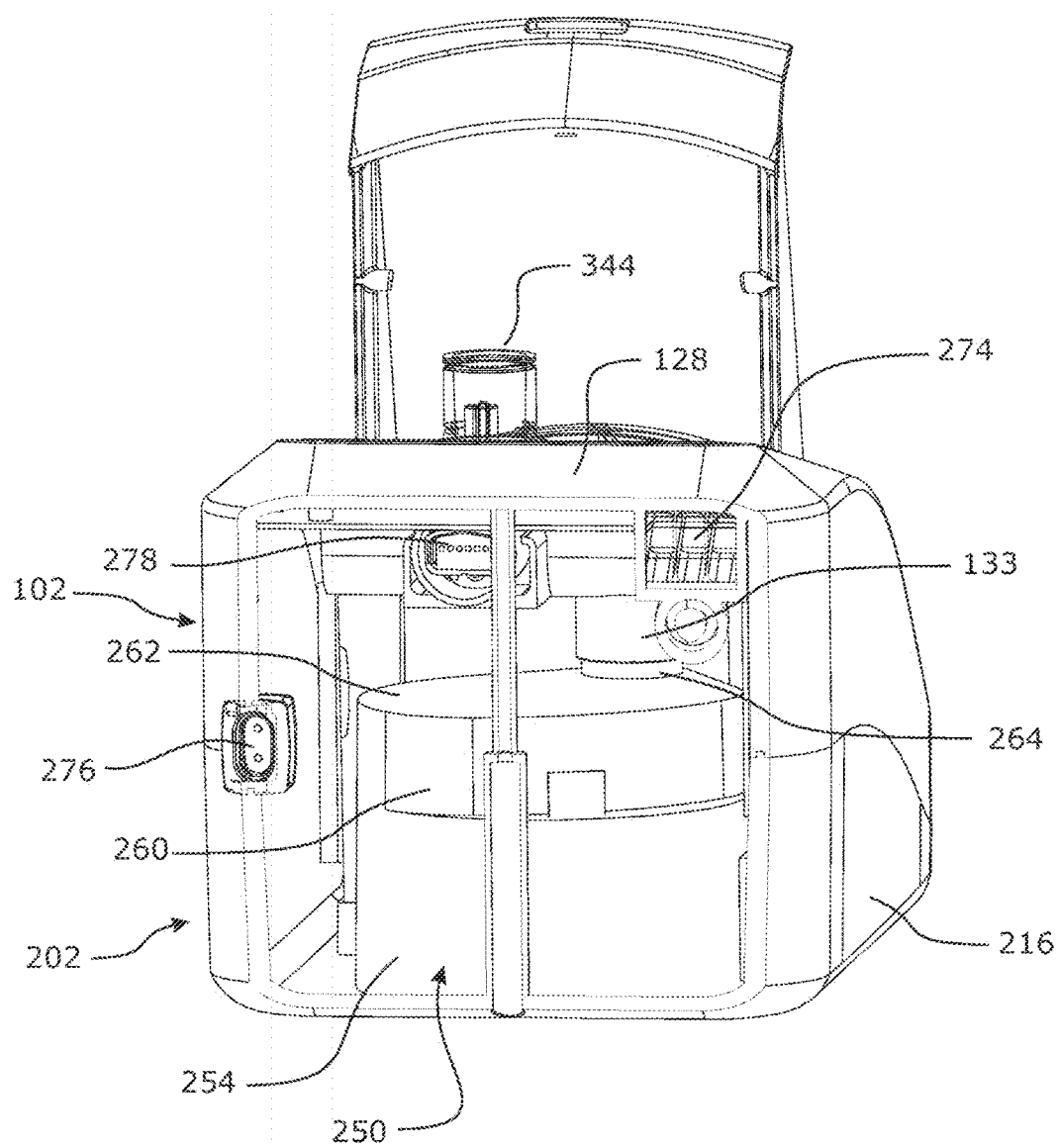
FIG. 14 is a rear perspective view of the flow therapy apparatus sectioned adjacent the rear edge of the apparatus, showing the arrangement of a portion of the main housing that provides the recess for receipt of the motor and/or sensor sub-assembly.
Figure 15:
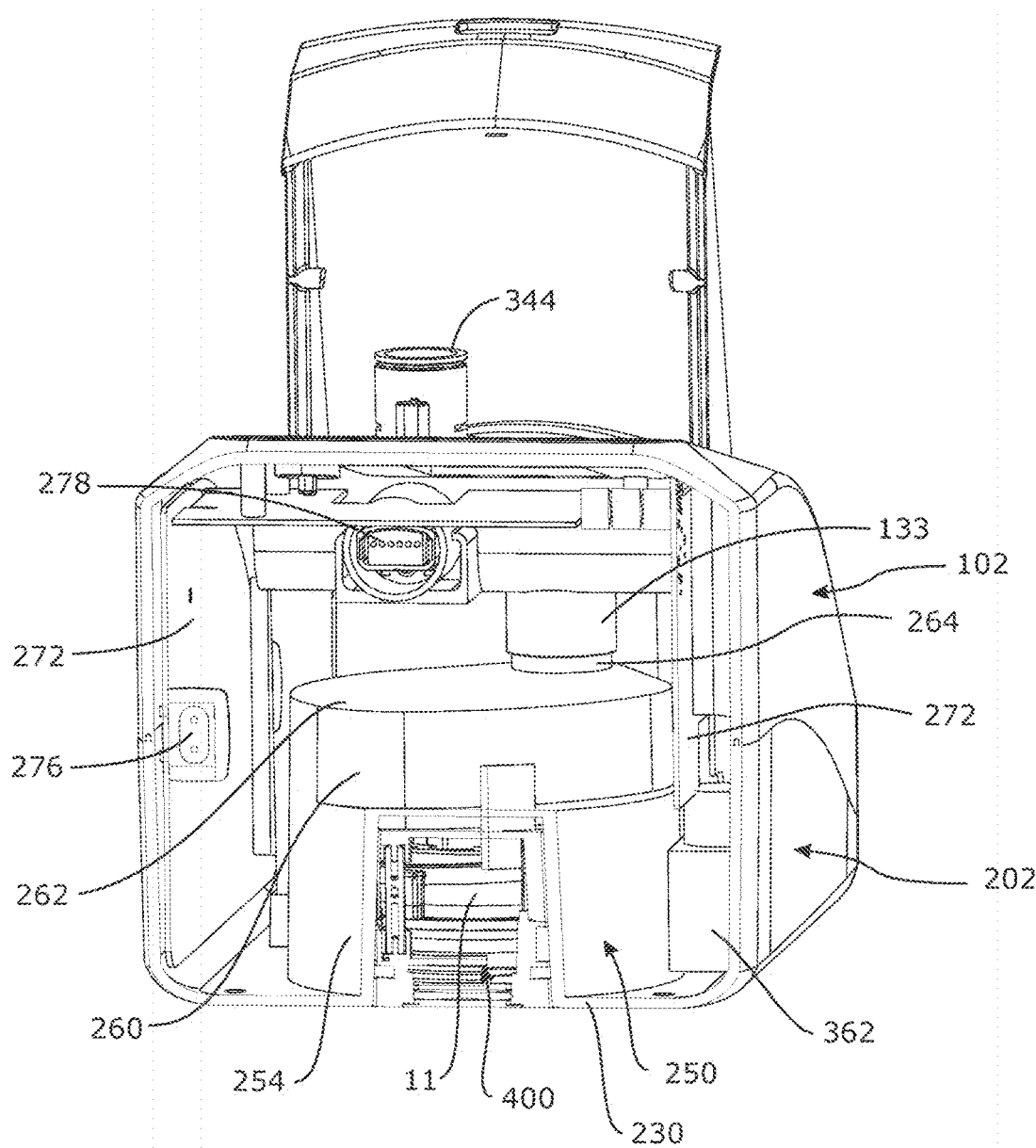
FIG. 15 is a view similar to FIG. 14 but sectioned closer to the front of the apparatus.
Figure 16:
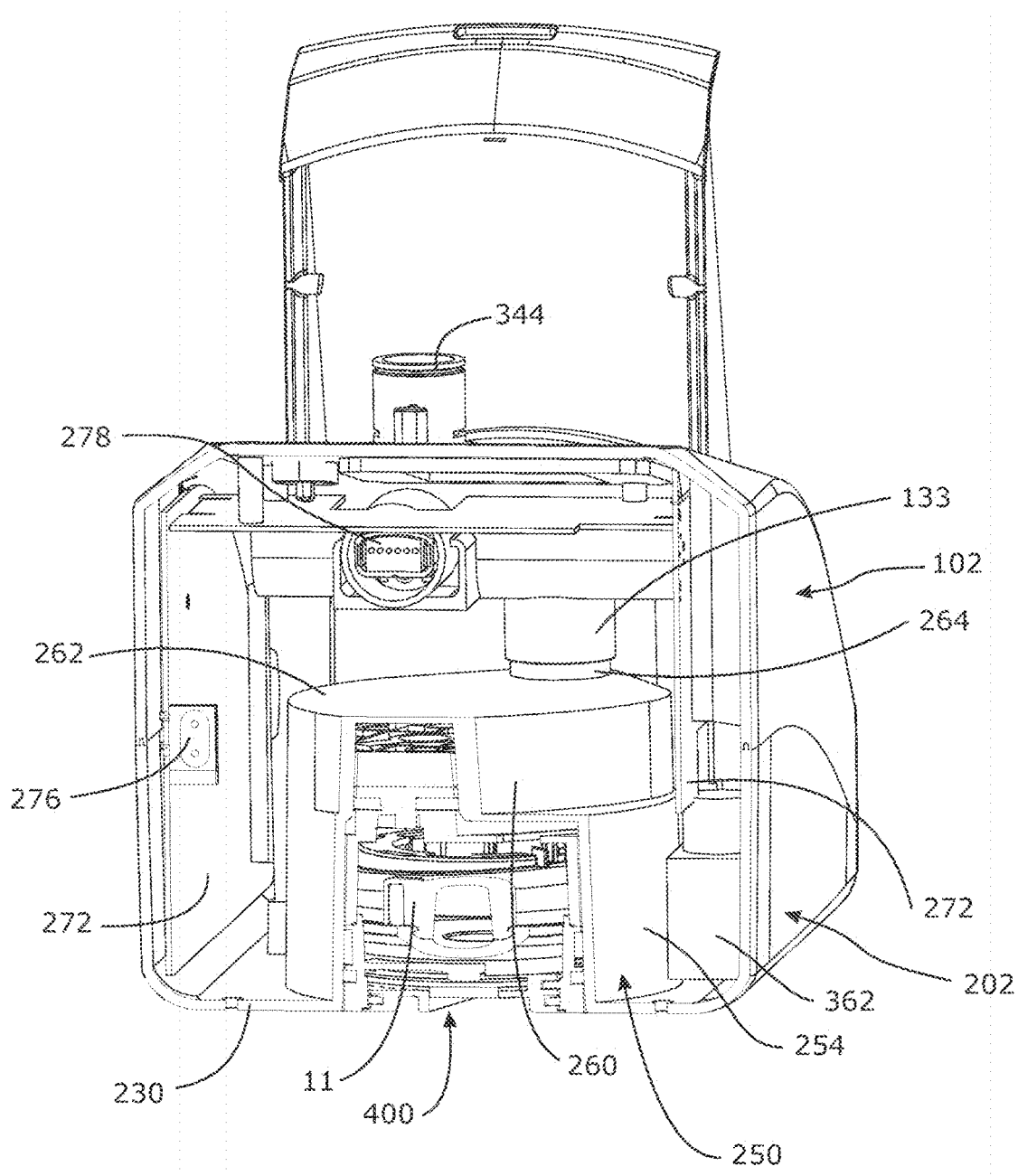
FIG. 16 is a view similar to FIG. 15 but sectioned closer to the front of the apparatus.

FIG. 12 shows an alternative embodiment of sensing printed circuit board (PCB) 2200. The sensing PCB can comprise ultrasonic transducers 2204, and one or more of separate gas temperature sensors 2205, heated temperature sensing elements 2206, humidity sensors including humidity only sensors to be used with a separate temperature sensor and combined humidity and temperature sensors, sensors for measuring barometric pressure, sensors for measuring differential pressure, and/or sensors for measuring gauge pressure, The sensing PCB can comprise drivers, microcontrollers, and/or other circuitry 2207. A heated temperature sensing element can comprise a heated temperature sensing element, hot wire anemometer, such as a platinum wire or heated thermistor, and/or a negative temperature coefficient (NTC) thermistor. Other non-limiting examples of the heated temperature sensing element include glass or epoxy-encapsulated or non-encapsulated thermistors. The heated temperature sensing element is configured to measure flow rate of the gases. The direction of gas flow is indicated in FIG. 12 by the arrow 2203. The general direction of air is away from one upstream transducer 2204a and toward another downstream transducer 2204b.

One or both of the electronics boards 272 will be in electrical communication or coupled with the sensors to process information received from the sensors and operate the apparatus 10 based on the information received from the sensors.

Figure 19:
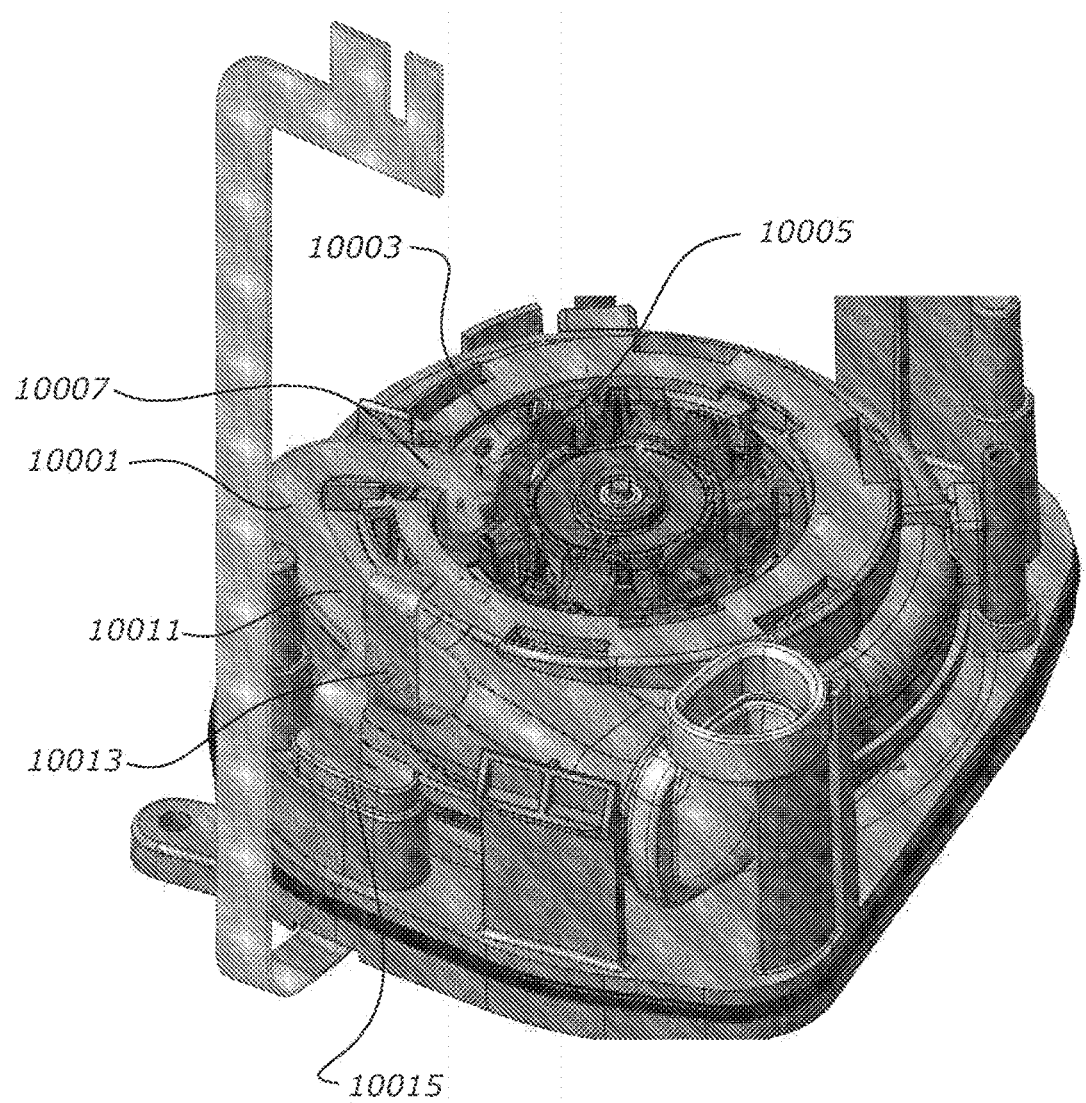
FIG. 19 shows a FPC in an in-use configuration showing the shape of the FPC when installed.
Figure 20:
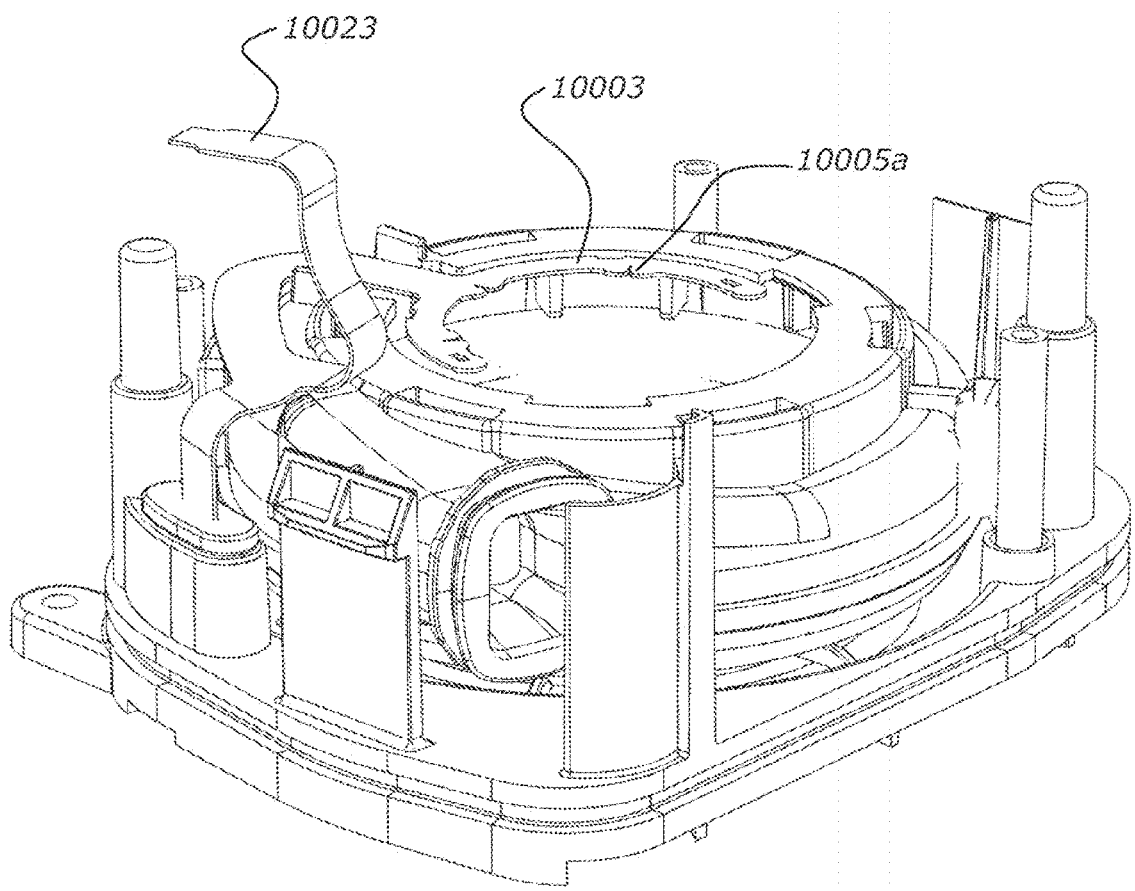
FIG. 20 is a view similar to FIG. 19 with the tail of the FPC not shown and the motor not shown.
Figure 21:
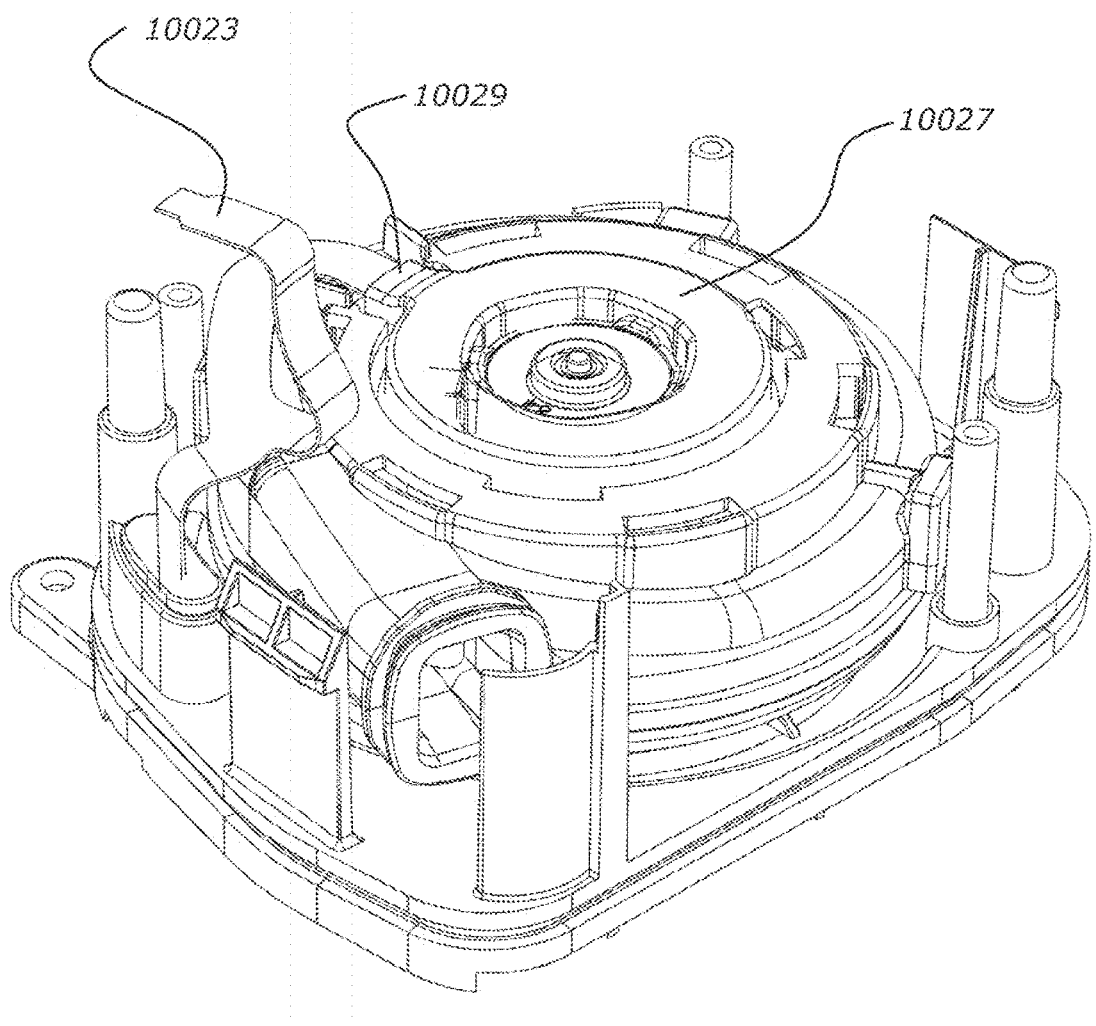
FIG. 21 shows the FPC and motor shield in an in-use configuration showing the shape of the FPC when installed with the tail of the FPC not shown.
Figure 22:
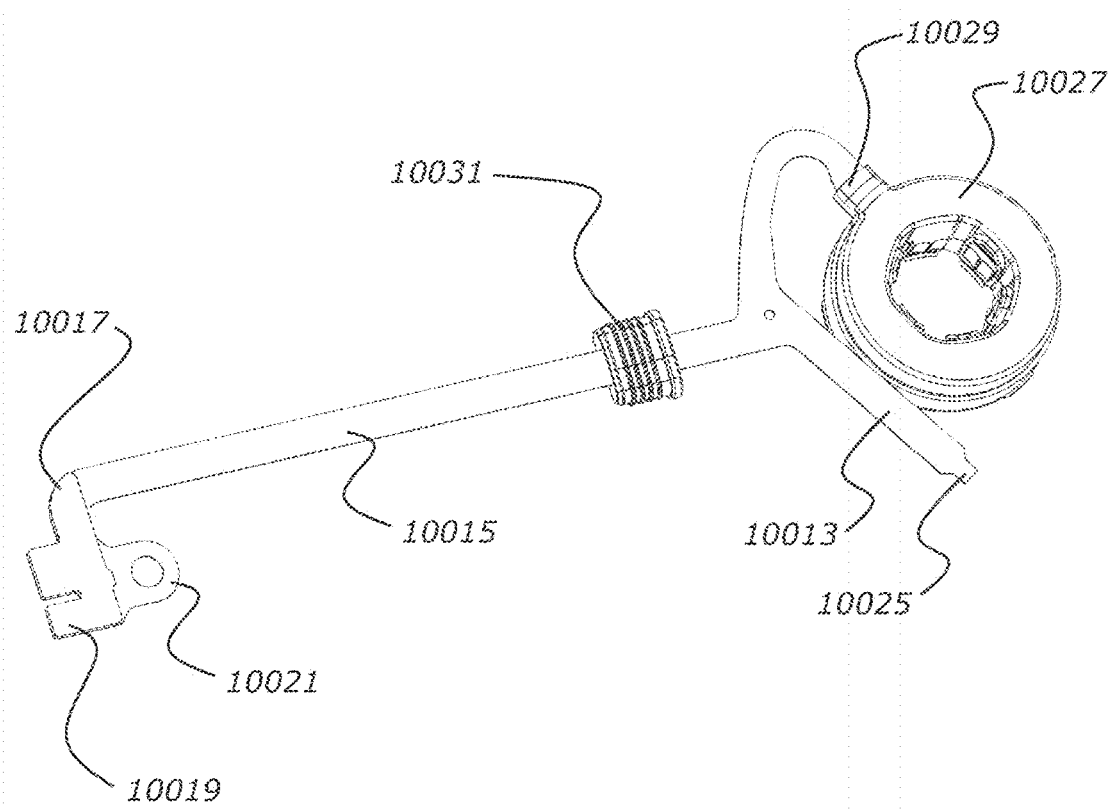
FIG. 22 shows the FPC and motor shield in a non-use configuration.
Figure 23:
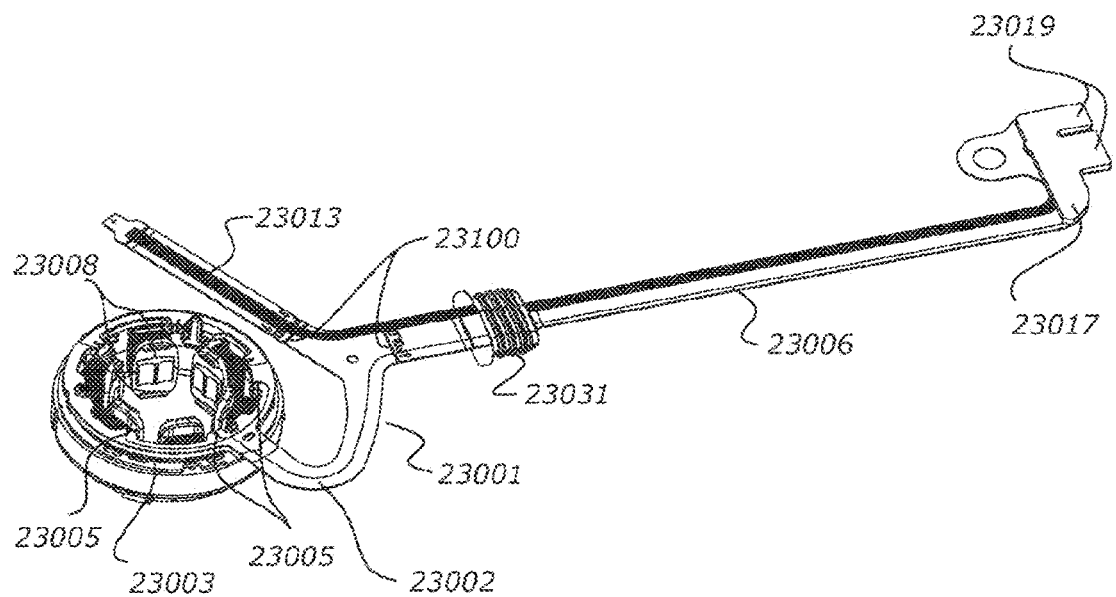
FIG. 23 shows a further configuration of the FPC and motor shield.

FIGS. 19 to 23 show features of the apparatus that pneumatically isolate the motor 402 and associated electrical components from the gasflow path in addition to features described above. In particular, FIGS. 19 to 23 show details of a flexible printed circuit (FPC) 10001. FIGS. 19 to 21 show the FPC 10001, or parts of the FPC in the in-use configuration. The FPC 10001 is electrically connected to the motor 402 for electrically connecting the motor to the electronics boards 272. FIGS. 22 and 23 show exemplary configurations of the FPC 10001 in a non-use or natural configuration before installation. The FPC 10001 is a ribbon-like component having a width, a relatively thin depth, and a relatively long length. The FPC 10001 is a flexible plastic substrate, such as polyimide or FR4 material, and contains a plurality of parallel traces that electronically connect the components. The advantages of a FPC include ease of assembly, ease of replacement, space saving, easier routing, lightweight design, additional design options (i.e. freedom of design) and improved aesthetics if it is necessary to replace one or more components because the interior of the apparatus has a tidy appearance. In addition, the traces of the FPC 10001 are pneumatically isolated from the gases from the gasflow path by the substrate of the FPC 10001, which is the polyimide. This can provide additional safety for the electronic circuits i.e. the traces on the FPC are isolated from the gases flow.

The FPC 10001 has a body 10015 and two branches extending from the body. The branches are described with reference to the drawings in more detail below. In summary, one of the branches is electrically connected to the motor 402 for electrically connecting the motor to the electronics boards 272 or other parts of the controller 13 and the other of the branches electrically connected to the sensor system for electrically connecting the sensor system to the electronics boards 272 or other parts of the controller 13.

The FPC 10001 has an arcuate, circular, or semi-circular first end 10003 that electrically connects to the motor 402. The arcuate, circular, or semi-circular first end 10003 may have one or more fingers 10005. In the embodiment shown, the FPC 10001 has three traces that electrically connect to the motor 402. An adjacent portion 10007 of the FPC 10001 extends radially from the arcuate, circular, or semi-circular first end 10003, which then smoothly transitions into a connecting section 10011. In the embodiment shown the connecting section is an arcuate section that closely follows the shape of the flow generator. In an alternative embodiment, the arcuate section may be another shape, such as a straight section. One branch of FPC 10001 is formed by the connecting section 10011, adjacent portion 10007, and first end 10003. The connecting section 10011 may be a stiffer section that the adjoining portion of the FPC.

FIG. 20 shows the FPC 10001 in an in use condition i.e. the FPC 10001 when it is installed.

The FPC 10001 also electrically connects the sensing PCB 456 to the apparatus. In particular, the FPC 10001 electrically connects the sensing PCB 456 to the electronics boards 272. The FPC 10001 has a branch 10013 with a plurality of traces that electrically connect to the sensing PCB 456. The FPC 10001 includes at least two traces. More preferably the FPC includes at least four traces. In one embodiment, the plurality of traces is nine traces. The end of the branch 10013 is formed as a narrow extension 10025 for being received by the sensing PCB 456.

The branch 10013 and connecting section 10011 join together to lead all twelve traces to the electronics board 272. It will be appreciated that the number of traces in the FPC 10001 will depend on the signals and data that is required to be transmitted by the sensing printed circuit board (PCB) 456 or 2200.

In one embodiment, the FPC 10001 is configured with the eight signal traces being positioned towards one side of the ribbon and the three motor traces on the other side of the ribbon. An advantage of this embodiment is that the motor traces and signal traces are spaced apart from each other and cross-talk between the traces is eliminated, or at least reduced. In another embodiment, the FPC 10001 is configured with the signal traces being positioned over the top of the three motor traces. In such an embodiment, the FPC 10001 has a layer of polyimide or other substrate between the traces.

FIG. 22 shows the FPC 10001 having a grommet 10031. The grommet 10031 provides a seal between the components when assembled. In particular, the grommet provides a seal where the FPC 10001 leaves the housing of the motor and/or sensor module 400.

The end of the FPC 10001 includes an opposing end 10017 that connects to electronic boards 272. The opposing end 10017 is formed as two parallel tags 10019 for being received by an edge connector of the electronic boards 272 or other parts of the controller 13. The end of the FPC 10001 also has an extension 10021. Extension 10021 is a pull tab so a user can remove the FPC from the electronic boards easily (e.g. for maintenance).

The FPC 10001 may have one or more stiffened regions to assist with attaching the FPC 10001 to other components. The stiffened regions may be formed as tags or ears or may simply be a stiffer part of the ribbon. The stiffened regions are thickened regions of the FPC. For example particular areas e.g. areas requiring strengthening may be thicker areas. The thickened areas or regions of the FPC are stiffer than other areas. Alternatively stiffened areas of the FPC 10001 may be thicker regions of the FPC that can be achieved by depositing additional material within those specific regions. The additional material may be FR4 material or additional polyamide material or polyimide material. The stiffened regions can have any suitable shape.

The FPC 10001 also includes meshed ground plane. An advantage of the meshed ground plane is that it has some flexibility compared to a solid ground plane. However, the ground plane may be a solid plane in some embodiments.

The apparatus may have one FPC 10001 that electrically connects the sensors and motor to the control board as described and shown in FIGS. 19 to 22. In an alternative embodiment, the apparatus may have one FPC for the motor 402 and one apparatus may have one or more FPCs for the sensors.

In another example embodiment the FPC 10001 comprises a plurality of signal traces and a plurality of motor traces. In this example the FPC 10001 comprises a total of eight sensor signal traces and three motor traces. The three motor traces correspond to each phase of the motor 402 (i.e. a three phase motor has three phases and hence each motor signal line corresponds to each phase of the motor). Preferably the FPC also includes a ground plane or a ground track. Alternatively any other suitable configuration for ground may be utilised. There in this example the FPC 10001 comprises eleven traces.

The shape of the FPC 10001 shown in FIGS. 19 to 22 and described has been designed to fit around the various components of the apparatus. It will be appreciated that the size and shape of the FPC 10001 may be chosen or designed differently depending on the shape, size, and/or location of the other components of the apparatus.

With reference to FIG. 21, the motor assembly includes a shield 10027. The shield 10027 is a non-permeable component to prevent, or at least substantially inhibit gases from the gasflow path reaching the windings 20068 and other electrical parts of the motor 402. In other words, the electrical components of the flow generator 11, including the electrical components of the motor 402, are pneumatically isolated from the gases from the gasflow path. In particular, the windings 20068 of the motor are pneumatically isolated from the gases from the gasflow path. Other components that are pneumatically isolated from the gases are the poles 20063.

The shield 10027 is a substantially annular component. When viewed from below, the shield completely covers the motor and part of the FPC 10001. In an alternative embodiment, the shield may not completely cover the motor from below, provided the shield isolates the windings and other electrical components. The shield 10027 fits snuggly around the motor and in particular, the windings 20068. The shield 10027 substantially encapsulates the motor to prevent or at least substantially inhibit oxygen ingress into the motor near the windings. This helps to reduce fire risk due to oxygen ingress into an area that can cause sparks due to short circuit or arcing. In some configurations the shield 10027 may completely encapsulate the motor windings. In some configurations the windings may be substantially sealed or isolated from air/oxygen.

The shield 10027 may be overmoulded onto the motor 402 as part of the manufacturing process. In an alternative embodiment, the shield 10027 may be formed, for example by moulding, as a separate component and then assembled with the motor 402. In this alternative embodiment, the shield may be formed as two or more parts that are assembled and sealed such that the electrical components of the motor 402 are pneumatically isolated from the gases from the gasflow path. The two or more components may be plastic components.

The shield 10027 has a tab 10029 for receiving the FPC 10001. The shield may be overmoulded onto the FPC as part of the manufacturing process. The overmould material flows into the gaps to encapsulate the FPC 10001. In an alternative embodiment, the shield may be formed, for example by moulding, as a separate component and then assembled with the FPC. The FPC 10001 also includes an extension 10023 that extends substantially upwardly and includes a bent section to direct upwardly to connect at least the motor traces to the control board e.g. control board 272. Alternatively the extension 10023 may connect to the sensing traces or a sensing PCB.

The shield 10027 may also act as a vibration isolator. The shield 10027 is configured to absorb vibrations caused by movement of the impeller or of other components of the motor during operation. The absorption of vibrations can mitigate rattling of the motor inside of the sub-assembly housing, which in turn can reduce noise emitted by the motor 402. The absorption of vibrations can also mitigate material fatigue on various components of the motor and/or sensor module 400. The shield 10027 may be constructed from a silicone material. In other configurations, other resilient materials including but not limited to acrylic resins and polyurethane resins might be used. In some configurations the shield may comprise an overmoulded material such as a thermoplastic or thermoset or silicone material. Preferably the material is an inert material that does not react to high oxygen concentrations. In one example the shield may be formed from PBT material (polybutylene terephthalate). Alternatively the shield material may be HDPE material or a nylon material.

In an alternative configuration, the vibration isolation properties of the shield 10027 may be increased by providing one or more springs or resilient structures that further vibrationally isolate and/or absorb vibrations caused by movement of the impeller or of other components of the motor during operation.

Figure 23A:
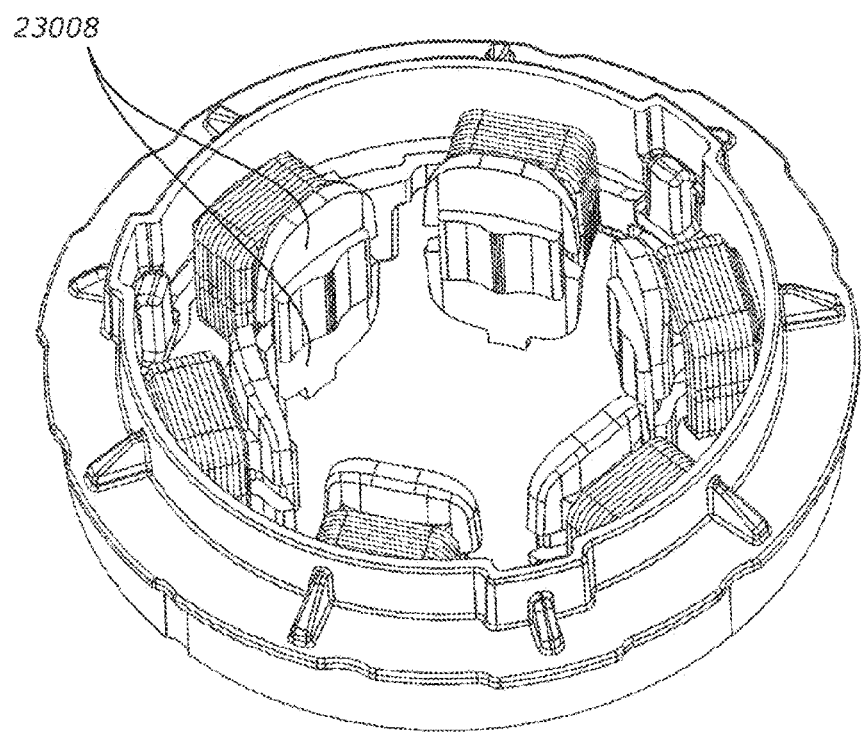
FIG. 23A is a detailed view of the FPC circular portion of FIG. 23.

FIG. 23 shows a further configuration of the FPC 23001 and the shield 10027 that can be used with the motor and FIG. 23a is a detailed viewed. As shown in FIG. 23 the FPC 23001 has an arcuate section 23002 that leads into a circular portion 23003 that extends around and connects the windings (i.e. coils) of the electrical motor. The motor includes three pairs of windings i.e. total of 6 coils. The circular portion 23003 interconnects all the windings of the motor 402. The circular portion 23003 interconnects the two halves together. The circular portion is can be semicircular or horse shoe in shape. Alternatively a completely circular element may be used to interconnect the windings. The circular portion 23003 includes three slots 23005 that correspond to and connect with three coils of three coil pairs of the stator. The stator includes three coil pairs with three active coils that are connected to the slots 23005 and then connected to the rest of the electronics via the FPC 23001. The other three coils (i.e. the ones not connected to the slots 23005) are connected to a common node (not illustrated). The common node may be located in any suitable location, and in one example may be located at the edge of the circular portion 23003 of the FPC. The motor in the illustrated configuration is a three phase motor, and hence uses three coil pairs. It will be appreciated that another motor may be used that is not a three phase motor.

The FPC 23001 may further include a supporting structure, for example a supporting ring, on the circular portion that connects to the stator. The supporting structure may be any substantially rigid material, such as FR4 material, or additional polyamide material or polyimide material. The circular portion 23003 may be bonded (e.g. glued) to the supporting structure, and the combined structure may then clipped to the stator. This occurs before the windings are electrically connected to the FPC and the entire stator structure is overmoulded. The supporting structure holds the FPC in place during overmoulding to prevent, or at least substantially inhibit, the FPC from floating to the top of the overmould material during moulding before the overmoulded material sets. The supporting structure also prevents, or at least substantially inhibits, the FPC from distorting during overmoulding. In an alternative embodiment, the supporting structure may be a thickened region of the FPC substrate.

The FPC 23001 includes three motor traces. Each motor track corresponds to each pair of windings. The extension 23013 interconnects with the sensing PCB and supports the sensing traces from the sensors. Preferably at least one or more guards 23008 may be located that sandwich the stator core. The windings are wound around the guards as shown in FIG. 23A, insulating the coils from the stator core. The guards 23008 are preferably formed of plastic.

The FPC includes a grommet 23031, which provides a seal between the components when assembled. In particular, the grommet 23031 provides a seal where the FPC 23001 leaves the housing of the motor and/or sensor module 400. An elongate section 23006 extends from the FPC portion adjacent the windings to a circuit end 23017. The circuit end 23017 of the FPC may further comprise a pair of legs 23019 for being received by an edge connector of the electronic boards 272 or other parts of the controller 13. The FPC also includes a shield (not shown in FIG. 23) that is preferably formed by overmoulding the windings. The overmould material can be any suitable material and at least partially isolates the windings. The windings are covered and at least partly pneumatically isolated. In some configurations the windings may be totally pneumatically isolated i.e. totally encased in the shield.

The FPC 23001 described is advantageous because it functions as a support to manage the wires from the stator.

The use of the FPC provides for increased use configurations and prevents wires from getting tangled. The flexibility allows the FPC to be routed through various paths. The FPC may be a single layer FPC but alternatively may be a multi-layer FPC. The FPC 23001, as shown in FIG. 23 is a multi-layer FPC. The motor traces are preferably disposed on separate layers of the FPC. Each of the layers supporting the motor traces is separated by an insulation layer. Preferably there is an insulation layer between each of the separate layers. The separation of motor traces maintains a required separation distance between the motor traces to comply with safety standards and to prevent arcing. There is also a ground track disposed on a layer of the FPC and helps to reduce electrical interference. The FPC is preferably made of polyamide material layers and layers of a suitable insulation material. There may be insulation provided on one or both edges of the FPC to prevent arcing with any other electrical components.

Some sections of the FPC 23001 may also include weakened sections or bending zones 23100. These weakened sections or bending zones 23100 are labelled FOLD on FIG. 23. The weakened sections or bending zones allow for easier bending or flexing of the FPC. The weakened sections or bending zones allow for easier routing of the FPC within the housing of the apparatus for delivering flow (i.e. a breathing assistance apparatus). In some configurations the FPC 23001 may include stiffened or reinforced regions. The stiffened regions may be formed from thicker PCB material e.g. FR4 material by deposition or any other suitable process. Alternatively the stiffened regions may be created by adding or attaching a stiffer material at specific regions of the FPC. In one example the circuit end 23017 may be formed as an edge connector and may be stiffer than other sections of the FPC.

The configuration described with reference to FIG. 23 can be particularly useful for high flow devices e.g. devices that provide high flow therapy or high flow oxygen therapy. It is understood that the configuration of FIG. 23 can be used with any type of flow generator in a breathing assistance apparatus or any other apparatus for delivering flow.

Figure 24:
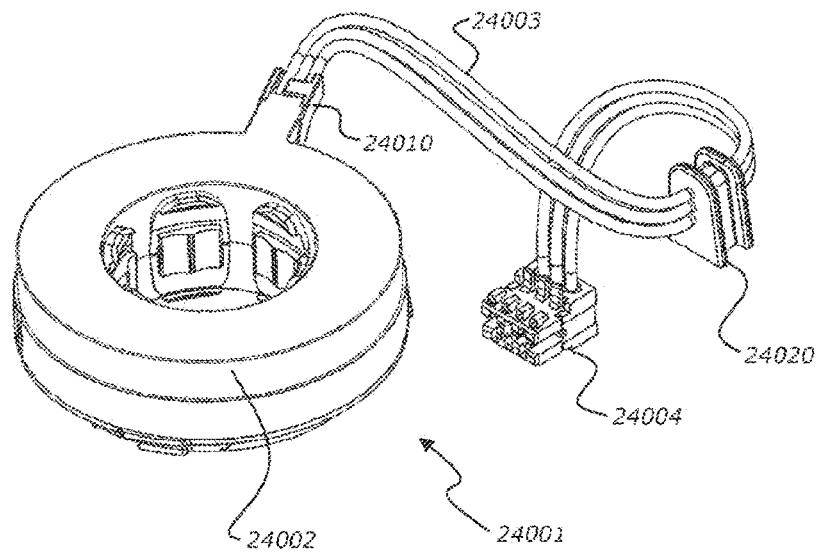
FIG. 24 shows a view of components of a motor and/or sensor module of a breathing assistance device that includes a covered stator.

FIG. 24 shows components of the motor assembly that includes a covered stator 24001. The stator is covered by a shield 24002. The shield 24002 is preferably an overmoulded material. The stator 24001 is potted (covered) by the overmoulded material to isolate the conducting surfaces/conducting regions from the air path. The motor includes a chassis and a tongue portion 24010 extending from the chassis. The tongue portion 24010 routes the wires from the motor outward and prevents tangling of the wires. The wires from the motor are flying leads 24003. There are at least three flying leads each one corresponding to a wire pair. The motor in FIG. 24 is a three phase motor and hence includes three wire pairs forming three phases. The flying leads includes a grommet 24020 that helps to seal off the motor from the air path. The flying leads 24003 terminates in a connector 24004 to connect to a corresponding connector at a controller, circuit or another PCB. The shield 24002 helps to prevent or at least reduce ingress of oxygen around the motor in order to prevent fires from occurring within the motor or around the stators due to any sparks or short circuits in the stator windings.

Further components of the motor and/or sensor module will now be described in more detail. In particular, components of the flow generator 11 will now be described, with particular reference to FIGS. 25 to 82. In the preferred form, the flow generator (also referred to as a blower or fan unit) 11 comprises the rotating impeller 72001 located inside a casing having the form of a snail or scroll casing 25001.

With reference to FIGS. 77 to 82, another embodiment of the shield 77001 will now be described. The features and functions of this embodiment are the same as the features and functions of the embodiments shown and described in relation to FIGS. 19 to 24, except as described below.

The stator is overmoulded with the shield 77001, the shield comprising an overmould material.

The stator preferably comprises a stator core having an annular portion 82003 and a plurality of stator teeth 82005 extending from the annular portion, each stator tooth having an inwardly facing tooth face. The stator core may be a laminated stator core in a preferred embodiment. The windings are wound around each of the stator teeth 82005.

The stator further includes one or more guards 82001 that sandwich the stator core, and are located between the stator core and the windings, insulating the windings from the stator core.

Figure 82:
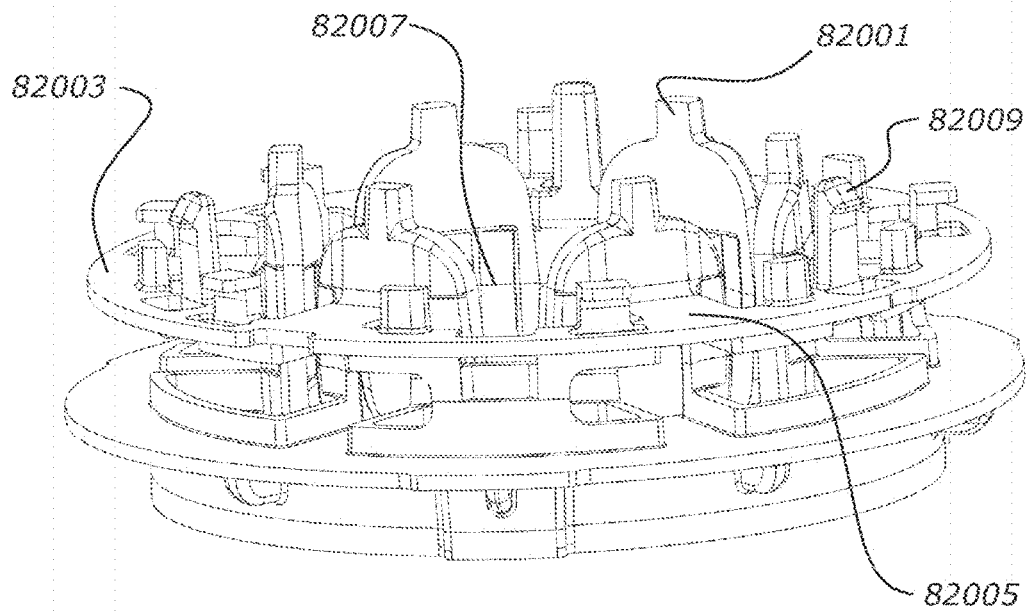
FIG. 82 is a perspective view of the stator.

The guards 82001 are preferably configured such that overmould material reaches at least partially between the stator core and the windings. For example, the guards 82001 may include apertures or recesses for ingress of overmould material during the overmould process. In the preferred embodiment, two guards 82001 are used, one being located on an upper face of the stator core and one being located on the lower face of the stator core. The two guards 82001 connect at a joining region 82007 in a plane of the stator faces, as shown in FIG. 82. Preferably the overmould material covers the joining region, such that oxygen ingress is minimised or prevented through any gaps between the guards 82001. The overmould material preferably further covers the tooth faces of the stator teeth 82005.

The one or more guards 82001 may have retaining features for retaining the stator within a housing. In the preferred embodiment the overmould material does not cover the retaining features. The retaining features include a face of the guard that is configured to cooperate with one or more ledges and/or clips on the housing. The retaining features are configured to prevent lateral and/or axial motion of the stator 35003. The overmould material covers all surfaces of the stator except for a portion of the guard or guards 82001. The motor further comprises an electrical connection on the stator 35003. The electrical connection is at least partially covered by the overmould material. As described above in relation to earlier embodiments, the electrical connection is preferably an FPC that is electrically connected to the windings. The connecting section 10011 of the FPC has a first portion connected to the windings and a second portion that extends from the motor 402. The first portion is covered by the overmould material. As mentioned above, the connecting section is a stiffer section than the adjoining portion of the FPC.

The FPC may further include a supporting structure on the portion that connects to the stator. The supporting structure may be any substantially rigid material, such as FR4 material, or additional polyamide material or polyimide material. The supporting structure may be bonded (e.g. glued) to the supporting structure, and the combined structure may then clipped to the stator. This occurs before the windings are electrically connected to the FPC and the entire stator structure is overmoulded. The supporting structure holds the FPC in place during overmoulding to prevent, or at least substantially inhibit, the FPC from floating to the top of the overmould material during moulding before the overmoulded material sets. The supporting structure also prevents, or at least substantially inhibits, the FPC from distorting during overmoulding. In an alternative embodiment, the supporting structure may be a thickened region of the FPC substrate.

To manufacture the stator, two guards 82001 are placed on the core, one above the stator core and one below the stator core. Wire is then wound around each of the stator teeth using conventional techniques to provide the windings. The FPC is then placed on the guard and electrically connected to the windings. The stator core, surrounded by the guards 82001, and the windings are then placed in a mould and the shield is formed by moulding a suitable material around those components to form the shield. In a preferred embodiment, the shield material covers the joining region, such that oxygen ingress is minimised or prevented through any gaps between the guards 82001. The overmould material preferably further covers the tooth faces of the stator teeth.

In alternative embodiments, the order of the steps described above may be different. For example, the stator core, windings, and guard may be placed in a mould, the FPC is placed in the mould, then the shield is formed by moulding a suitable material around those components to form the shield.

In an alternative embodiment, the shield may be selectively removable. In particular, the shield may be a separately manufactured component that is later assembled with the stator 35003.

The drawings and related description of the flow generator show the flow generator upside down compared to the typical in-use position. That is the component referred to as a top casing will be a bottom part of the flow generator in use and the components referred to as a bottom casing and bottom casing cap will be top parts of the flow generator in use.

Figure 25:
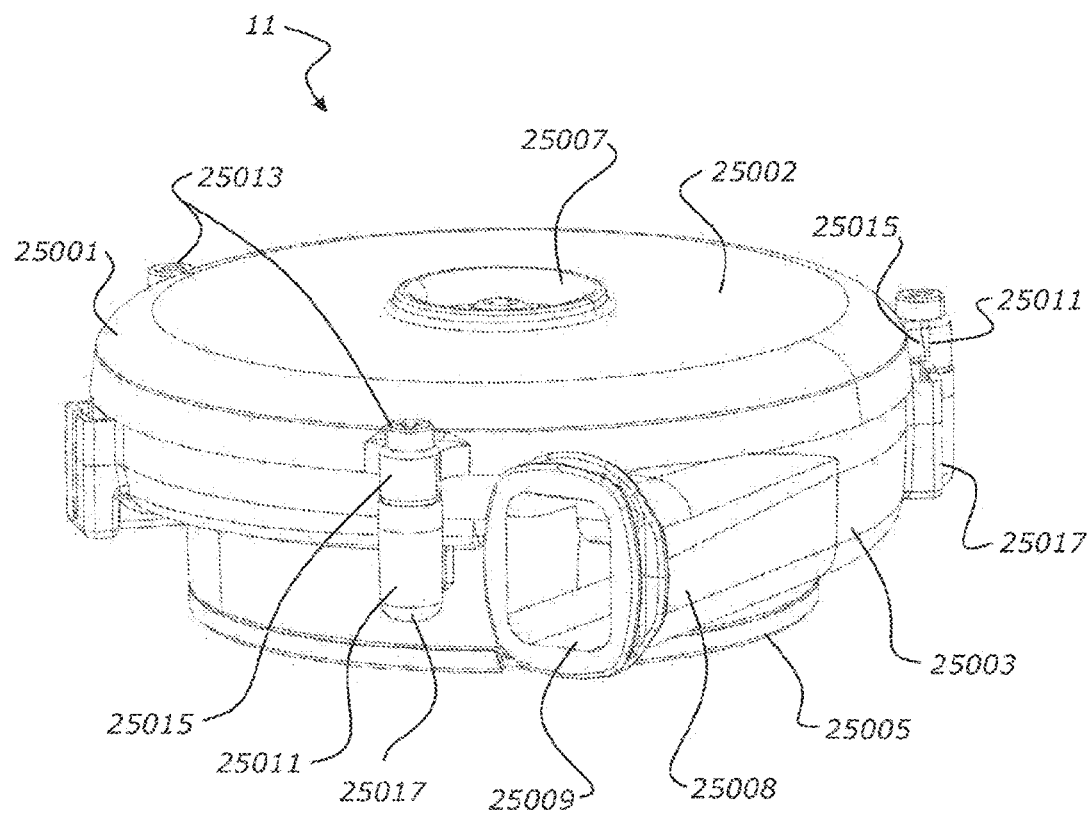
FIG. 25 is a perspective view of a flow generator of a breathing assistance device.
Figure 26:
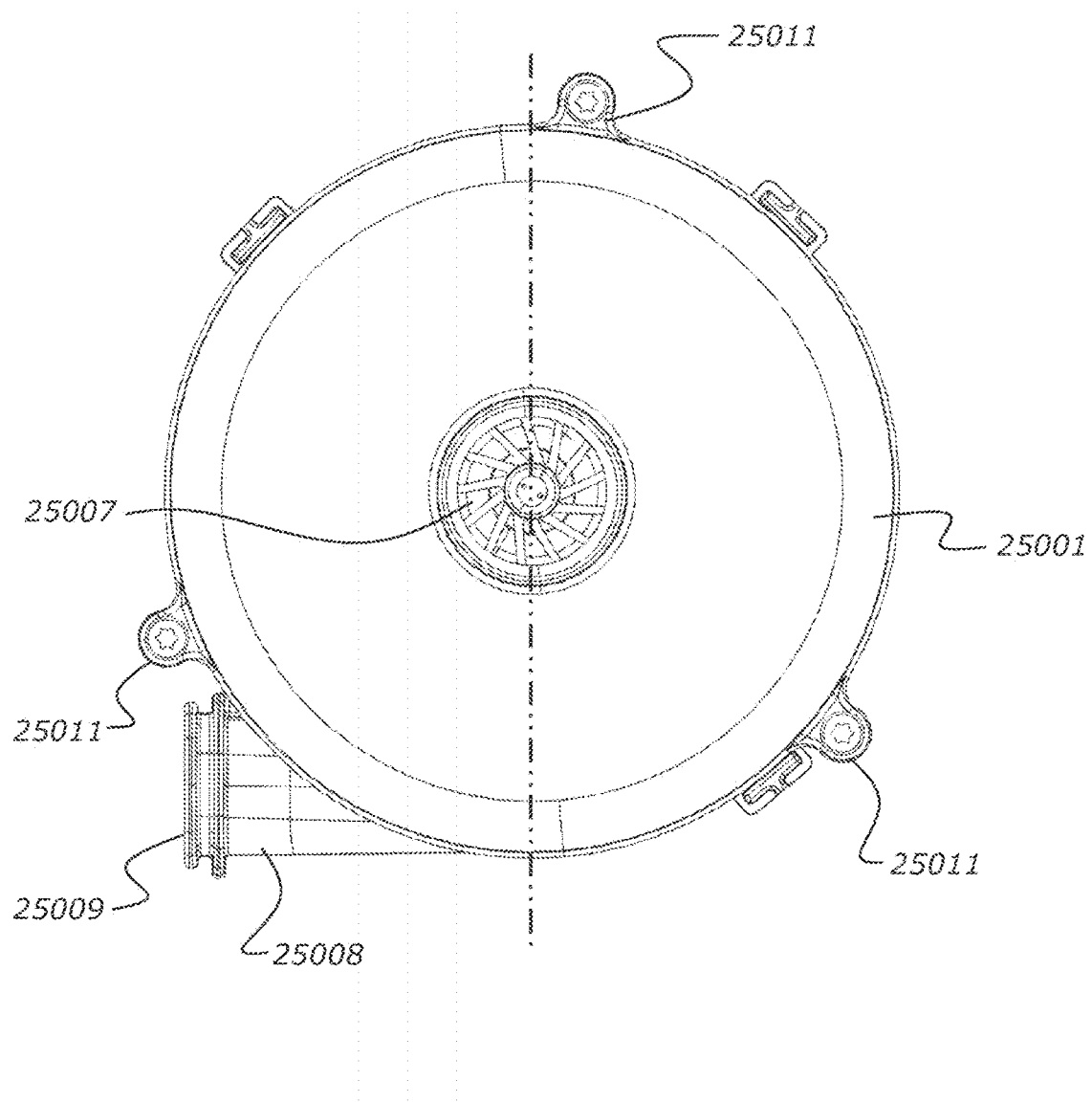
FIG. 26 is a top view of the flow generator of FIG. 25.
Figure 27:
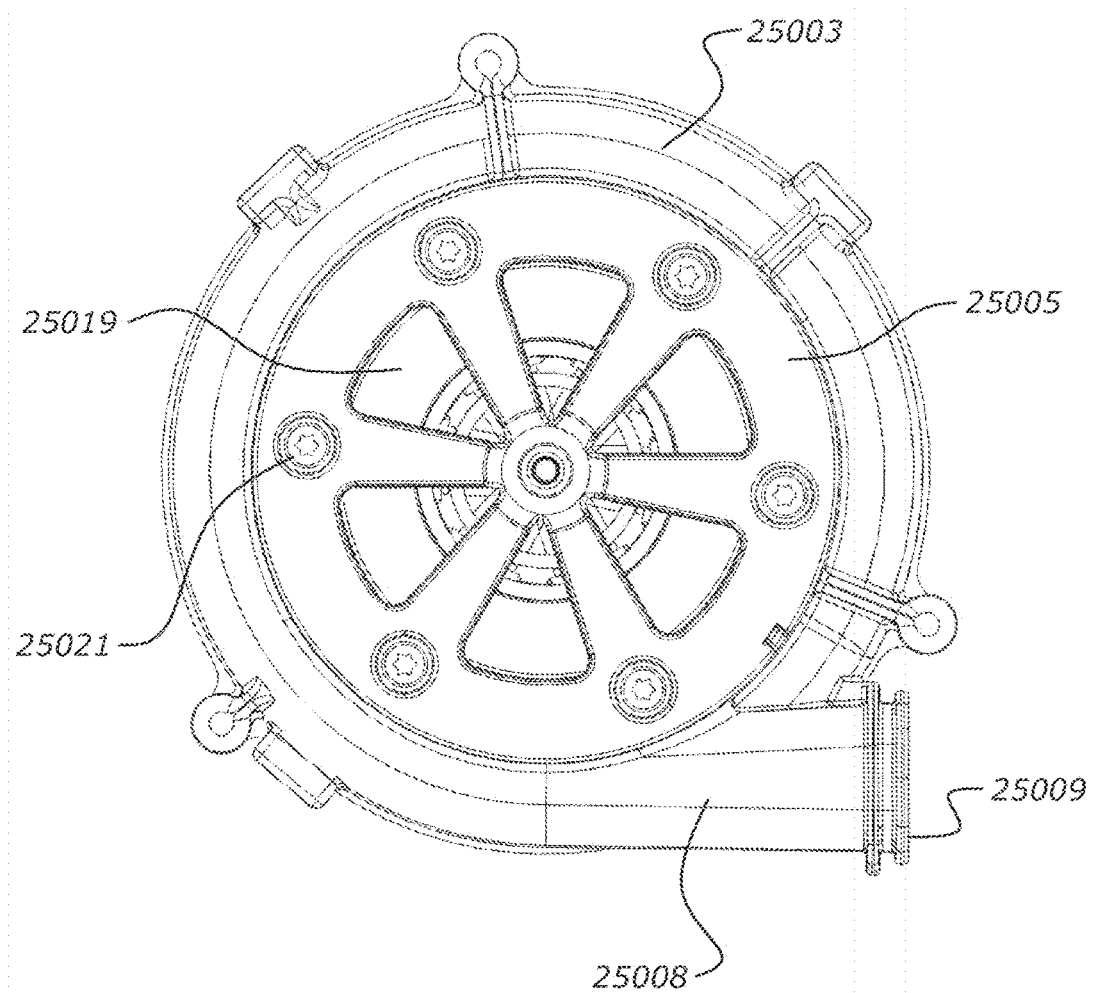
FIG. 27 is a bottom view of the flow generator of FIG. 25.
Figure 28:
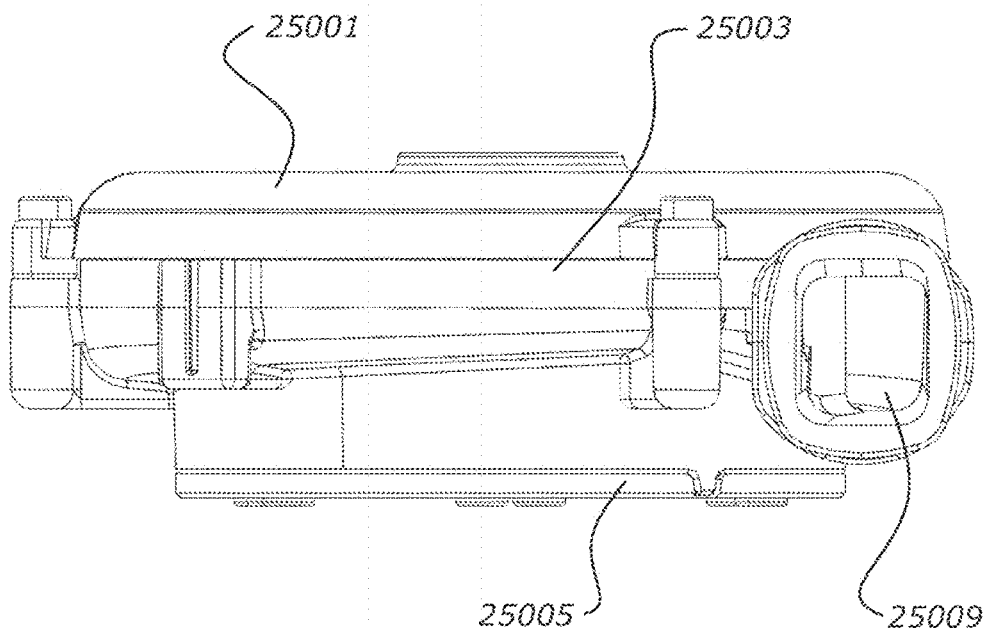
FIG. 28 is a front view of the flow generator of FIG. 25.
Figure 29:
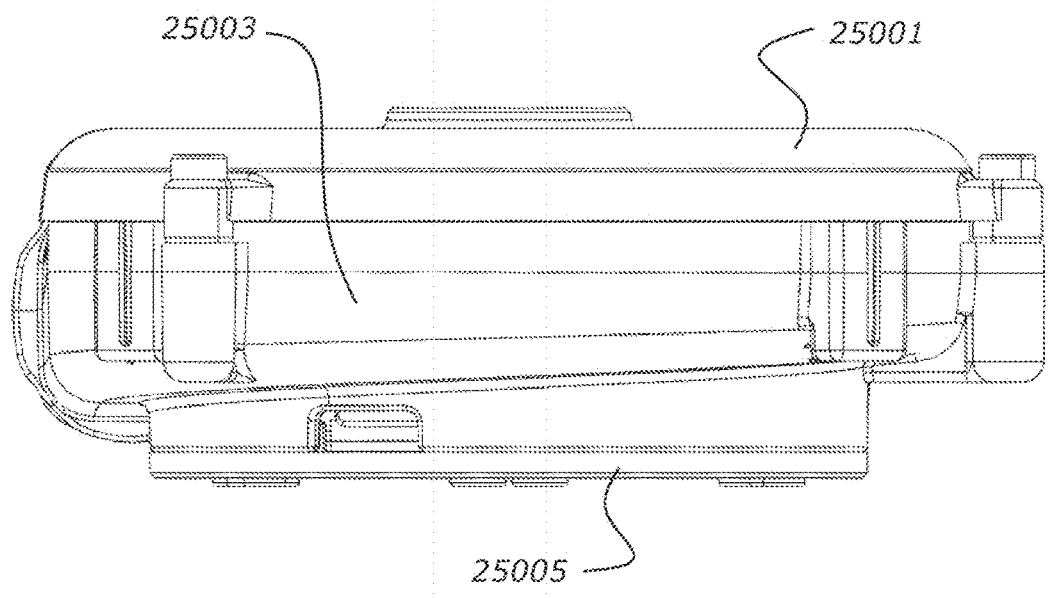
FIG. 29 is a rear view of the flow generator of FIG. 25.

It can be seen that the flow generator 11 appears generally circular in plan view, as shown in FIGS. 25 to 27. The flow generator casing 25001 includes a top casing 25002 and a bottom casing 25003, which engage around their respective peripheries. The top casing includes an inlet 25007. In the preferred form, the inlet 25007 is a circular hole located in approximately the centre of the top casing 25002 and passing from the outside of the casing to the inside. Air enters the flow generator casing 25001 via the inlet 25007. The preferred form of the casing 25001 of the flow generator 11 also includes an outlet passage 25008. In the illustrated configuration, the bottom casing 25003 includes the outlet passage 25008. The bottom casing also includes a bottom casing cap 25005.

In the preferred form, the outlet passage 25008 is a short passage formed as an integral part of the casing 25001 and aligned substantially tangentially to the circumference to the remainder of the generally circular casing 25001. A flow generator casing outlet or exit 25009 (see e.g. FIG. 25) is located at the outer end of the passage 25008. The outlet or exit 25009 is an aperture or hole. It should be noted that the flow generator casing exit 25009 could be located wherever is convenient on the outlet passage 25008 (i.e. it does not have to be at the end of the passage, it could be through the passage wall partway along its length, for example). The exit 25009 opens into a duct. The outlet passage 25008 forms part of the air path from the impeller 72001 to the humidifier inlet.

The flow generator casing 25001 encloses the impeller 72001 in use, except for the inlet 25007 and the exit 25009 of the outlet passage 25008. As described elsewhere in this specification, rotation of the impeller 72001 is driven by the motor 402, the fan or impeller 72001 being adapted for connection to the motor.

In the preferred form, the flow generator outlet passage or exit passage 25008 has a generally rectangular cross-section, and the exit passage 25008 is aligned substantially tangentially to the casing 25001. However, the cross-section of the flow generator outlet passage 25008 could be any suitable shape, such as oval, rectangular or circular. The flow generator outlet passage 25008 could also be arranged at any suitable angle to the impeller unit, for example facing radially outwards, or at any suitable angle between tangential and radial. The flow generator outlet passage 25008 causes the gases forced outwards by the impeller unit to coalesce as a fluidic gases stream, and dictates the direction in which the gases stream flows. The overall path or overall direction of the gases flow will be along the passage from the fan towards the flow generator casing exit 25009.

With reference to FIG. 26, the flow generator 11 includes three casing fastening mechanisms 25011 to secure the top casing 25002 and the bottom casing 25003 together. In the embodiment shown, the fastening mechanism 25011 are screws 25013. The screws 25013 extend through clearance apertures provided in bosses in the top casing. The screws are in threaded engagement with apertures provided in bosses in the bottom casing 25003. It will be appreciated that screws are readily removable and allow easy disassembly of the components, if required. For example, if components require maintenance. Other fastening mechanisms may be used, such as gluing, welding, or chemical bonding.

Figure 62:
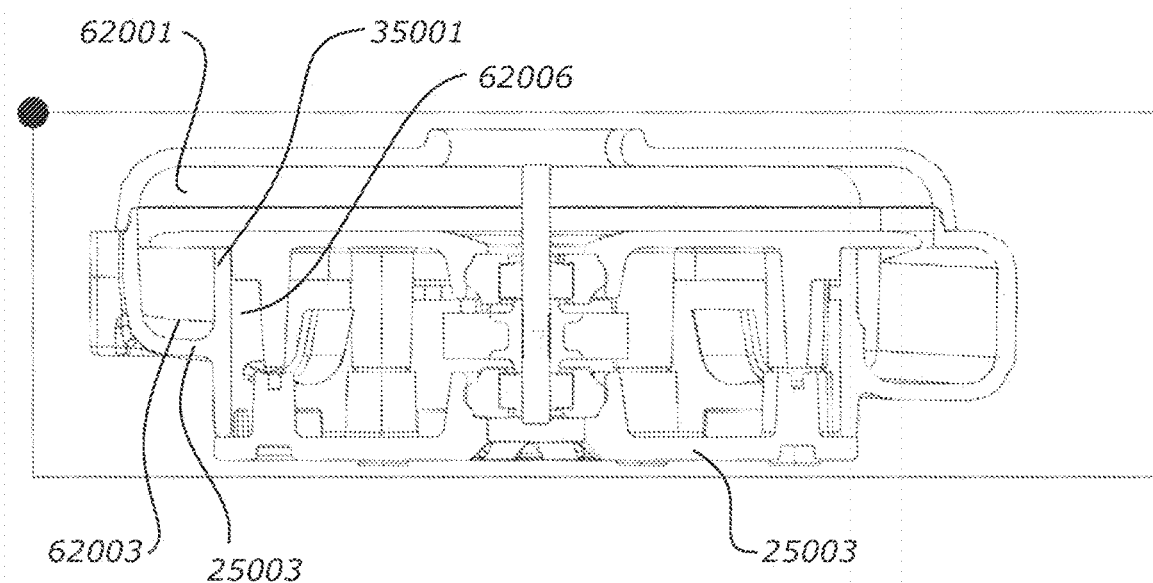
FIG. 62 is a cross-sectional view showing the housing.
Figure 63:
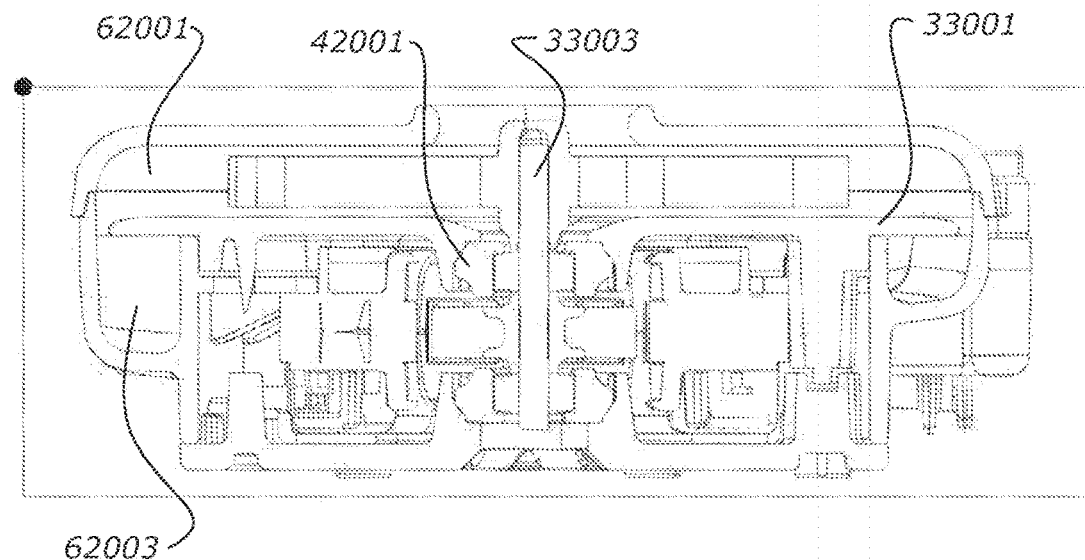
FIG. 63 is a cross-sectional view showing of the flow generator (blower).

The flow generator also includes a partition 33001 between the top casing 25002 and the bottom casing 25003. The partition 33001 and the inner surface of the top casing 25002 are profiled to substantially enclose the impeller blades when the top casing 25002, bottom casing 25003, partition 3301 and bottom casing cap 25005 are assembled. This forms a first interior region 62001 ("upper region"), which is shown in FIGS. 62 and 63. FIG. 33 shows a view similar to FIG. 32 with the impeller 72001 hidden, clearly showing the partition 33001.

The top casing 25002 has the inlet 25007 that defines the gases entry into the flow generator 11. The flow generator casing 25001 defines a volute where gases are collected and directed through before emission from the blower. In one configuration, the volute can be considered to be defined by the bottom casing 25003 and comprises a scroll disposed on an opposing side of the partition 33001 as the impeller 72001. In another configuration, the volute can be considered to be defined by the top casing 25002 and the bottom casing 25003, comprising the aforementioned scroll, in addition to the first interior region. The scroll transitions into the outlet passage 25008.

The scroll can increase from a lower cross sectional surface area to a higher cross sectional surface area along a length of the scroll. In other words, the cross sectional area of the scroll can increase as the scroll tends towards the outlet passage 25008.

Preferably the volute of either configuration also has a sealing inner wall 35001. The sealing inner wall 35001 defines a space internal to the lower casing that may be used to house the motor 402. The bottom casing 25003 and the partition 33001 form a second interior region 62003 ("lower region"), which is shown in FIGS. 62 and 63. When the casing is assembled, a seal is formed between the sealing inner wall 35001 and the partition 33001, which separates the gas flow path through the flow generator 11 from the motor 402.

The outlet passage 25008 of the flow generator unit 11 is connected to the volute via an opening. The opening and the volute wall define a tongue whereby gases circulating in the volute are diverged into the outlet passage 25008.

The partition 33001 is generally circular and substantially divides the top casing 25002 from the bottom casing 25003 thereby defining the upper and lower gases flow (interior) regions of the blower. To allow gases to flow from the upper region to the lower region an opening is located at, or close to the outer edge of the partition. The opening is most preferably formed by a cut-away in the partition 33001, or some other configuration/shape of the casing such that the combination/arrangement of the partition 33001 and the casing creates an opening or gap between the two. In the embodiment shown, the opening partition 33001 is circular and is located concentrically within the casing. As a result, the opening is an annular opening that is the same width around the perimeter of the partition 33001.

In an alternative embodiment, the curvature/centre of radius of the circumferential aperture may be offset from the centre of radius of the partition 33001 or otherwise has a curvature that differs from that of the circumference of the partition 33001 resulting in an eccentric or otherwise offset circumferential aperture around the circumference of the partition 33001. This produces an aperture with a crescent ("smile") shaped opening that spans a leading edge to a trailing edge, the aperture may be of any shape with a gradual opening and closing relative to the plane of impeller rotation.

The width and length of the aperture controls the velocity in the lower (volute) section of the housing. A wider and longer aperture increases velocity in the volute, for example.

By dividing the flow generator internal space into two separate regions a number of advantages can be realised. In a conventional blower, high velocity gases leaving the impeller are incident to the edge, or tongue, that defines a physical boundary where gases are split from the volute to enter the outlet passage. High velocity gas flow incident the tongue is turbulent and results in inefficiency, reducing flow generator performance. The turbulence caused by the tongue also introduces a source of noise. In contrast, dividing the casing of the preferred blower into the upper and lower regions reduces the impact caused by the tongue. The upper region allows the gases to circulate at a high speed. The gradual radial opening and closing of the preferred 33001 provides a fluid path to the lower region that is free from (or has reduced) aerodynamically turbulent edges. When circulating gases have entered the lower region, the enlarged volume of the volute encourages the gases to slow and increase pressure. The reduced gases velocity reduces the impact of turbulence normally caused by the tongue to a low or negligible level. The flow generator is therefore able to operate across a wide pressure and flow range with substantially reduced noise output when compared to other blowers. A wider and longer opening increases the flow rate of the lower region relative to the upper region. Therefore, the size of the opening is selected according to the desired flow rate and pressure range of the flow generator 11.

The shaft 33003 is held within the motor by a bearing structure. Preferably the bearing structure has one or more bearings 48001 and one or more bearing mounts 42001/50001. In one embodiment, the bearing mounts 42001/50001 engage with an outer race 48003 of each respective bearing on an inner surface and with the stator 35003 on an outer surface. The preferred engagement of the bearing mounts 42001/50001 to the bearings and the stator is frictional. To promote a frictional engagement, the bearing mounts 42001/50001 are made of a soft, yet resilient and/or flexible material such as silicone rubber or other elastomeric material. The material can be low creep, temperature stable, low compression set with a high tan delta (highly viscous), highly damped. Examples comprise:

Dough Moulding Rubbers like—NBR, Nitrile and Flouro silicone.

Thermo Plastic Elastomers (TPE's) like Santoprene™ by Exxon

Thermo Plastic Urethanes like Dynaplast™ by GLS Corporation

Heat Cured Casting Urethanes like 10T90 by National Urethanes

Other cold cast rubbery compounds such as RTV (Room Temperature curing Vulcanites) by Dow Corning, Whacker and others.

Such materials allow the bearing mounts 42001/50001 to compress when installed, then expand or deform into their chosen location to be held in place.

The bearing mounts 42001/50001 provide compliance to the rotatable shaft 33003. As rotatable objects, such as the rotor, shaft 33003 and impeller 72001 usually suffer from some degree of rotational imbalance, the bearing mounts 42001/50001 are able to isolate inherent rotation induced vibration from the motor rotor. It has been found that combination of the lightweight, shroudless impeller having a low rotational inertia, as described above, together with the given compliance of the bearing mounts 42001/50001 enables the rotor, shaft 33003 and impeller 72001 to be manufactured and any post manufacture balancing process for the rotating components entirely omitted. These advantages benefit manufacturing costs and time. The lightweight nature of the impeller allows any imbalances to be compensated by the bearing mounts 42001/50001. A lightweight impeller also allows faster speed response of the impeller to changing conditions. Any unwanted fluctuations in pressure due the lack of shroud can be compensated for by quickly changing the impeller speed to return pressure to the desired level.

With reference to FIGS. 37 to 47, a first preferred embodiment of a bearing mount will now be described together with associated components including the shaft. The bottom casing cap 25005 includes a bearing mount recess 57003 for receiving a first bearing mount. The partition 33001 also includes a bearing mount recess 33002 for receiving a second bearing mount.

Figure 37:
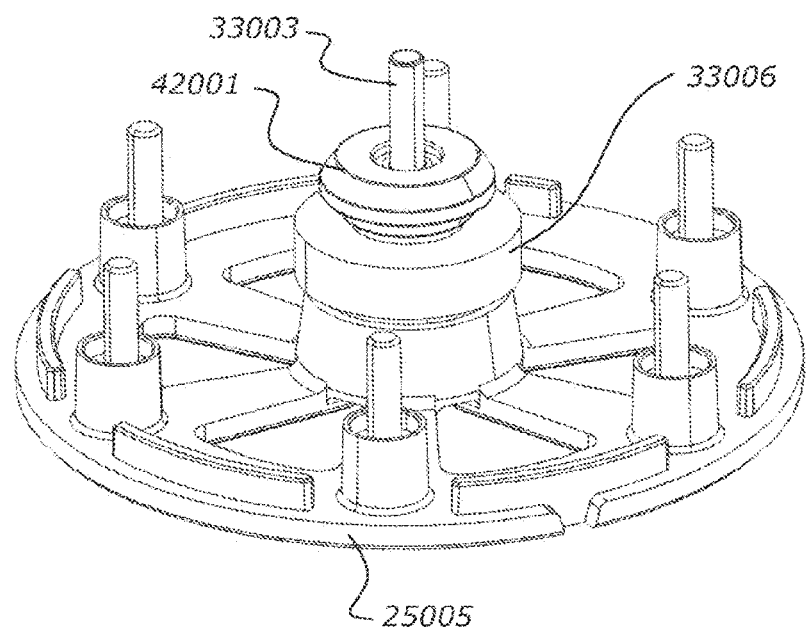
FIG. 37 is a perspective view of the flow generator of FIG. 25 with the stator assembly hidden.
Figure 38:
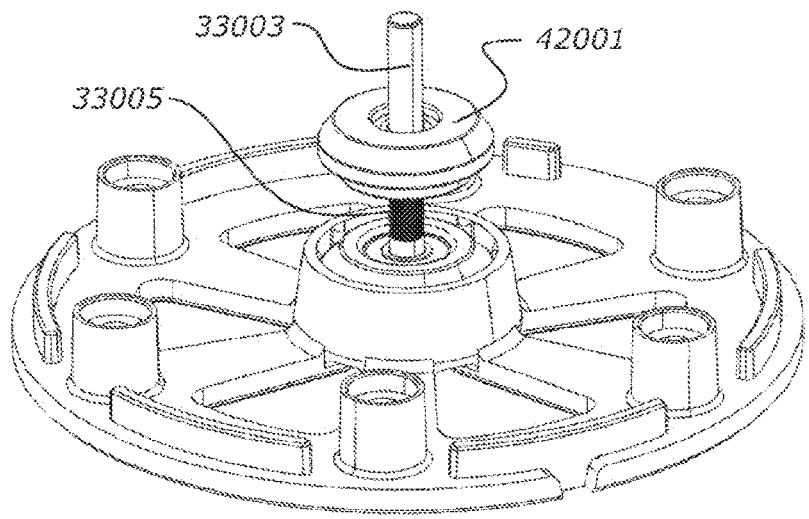
FIG. 38 is a perspective view of the flow generator of FIG. 25 with the rotor hidden.

FIG. 38 is a view similar to FIG. 37 with the rotor also hidden. A rotor 33006 connects to the shaft 33003 as described in WO2014/007655A1 and WO2014/097030A1. The contents of each of those specifications are incorporated herein in their entirety by way of reference.

Figure 36:
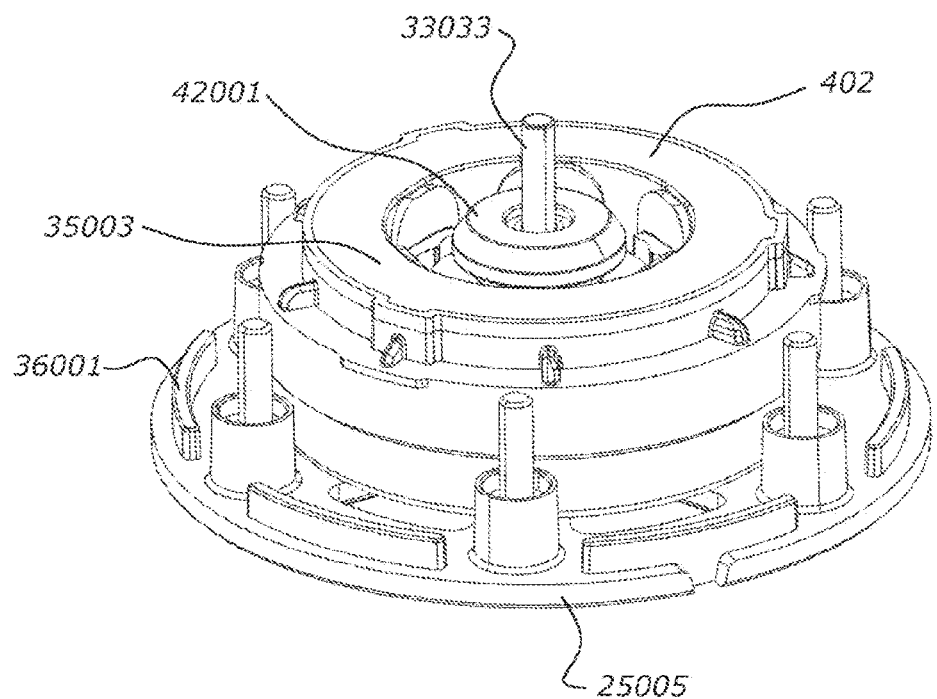
FIG. 36 is a perspective view of the flow generator of FIG. 25 with the bottom housing hidden.
Figure 39:
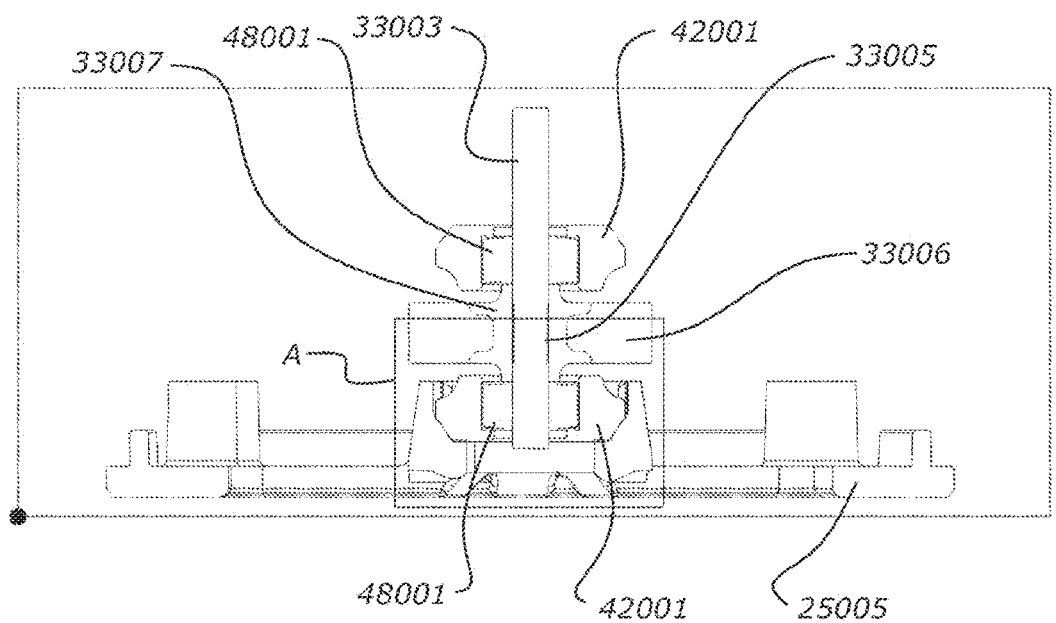
FIG. 39 is a cross-sectional view of the flow generator of FIG. 25 with the stator assembly hidden.

FIG. 39 is a cross-sectional view of the arrangement of FIG. 36. As described in WO2014/007655A1 and WO2014/097030A1, the shaft 33003 engages the rotor 33006 via a rotor/shaft engagement piece 33007. The preferred embodiment also has a roughened rotor section 33005 that may assist to maintain the position of the rotor/shaft engagement piece. However, both the rotor/shaft engagement piece 33007 and the roughened sections 33005 are optional features. The rotor/shaft engagement piece 33007 abuts the inner race of each of the upper and lower bearings so that the shaft 33003 and rotor 33006 spin in conjunction with this inner race.

Figure 40:
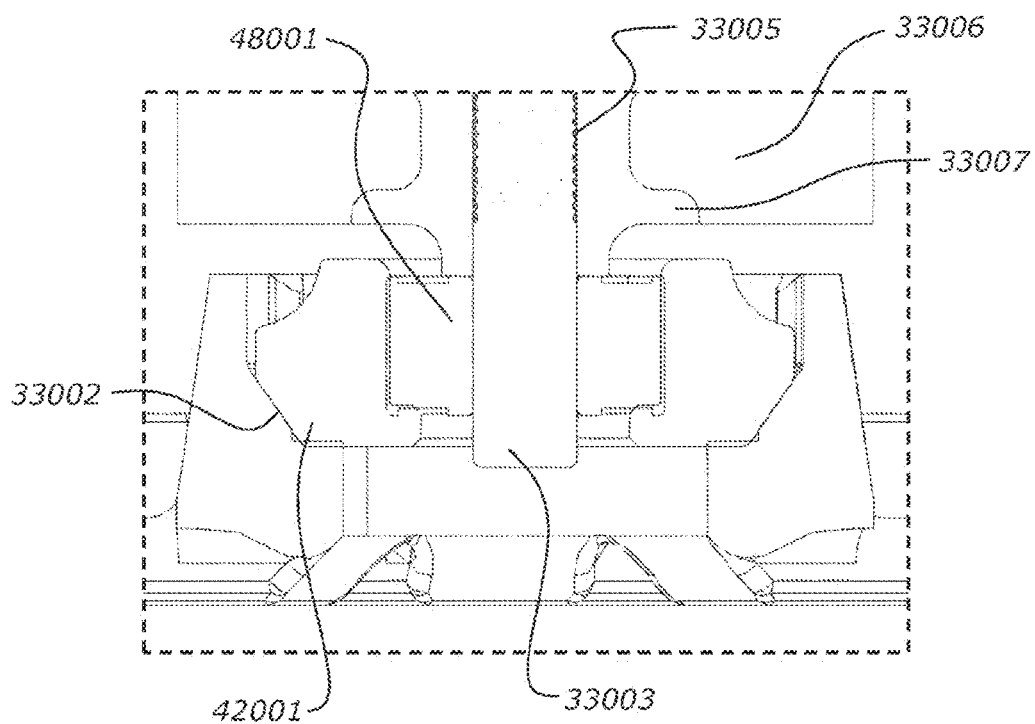
FIG. 40 is a detailed cross-sectional view of the flow generator of FIG. 25 with the stator assembly hidden.

FIG. 40 shows a detailed cross section of region A in FIG. 39. The shaft 33003 forms a running or slip fit with the bearing 48001, which itself forms an interference fit with the bearing mount 42001.

Figure 42:
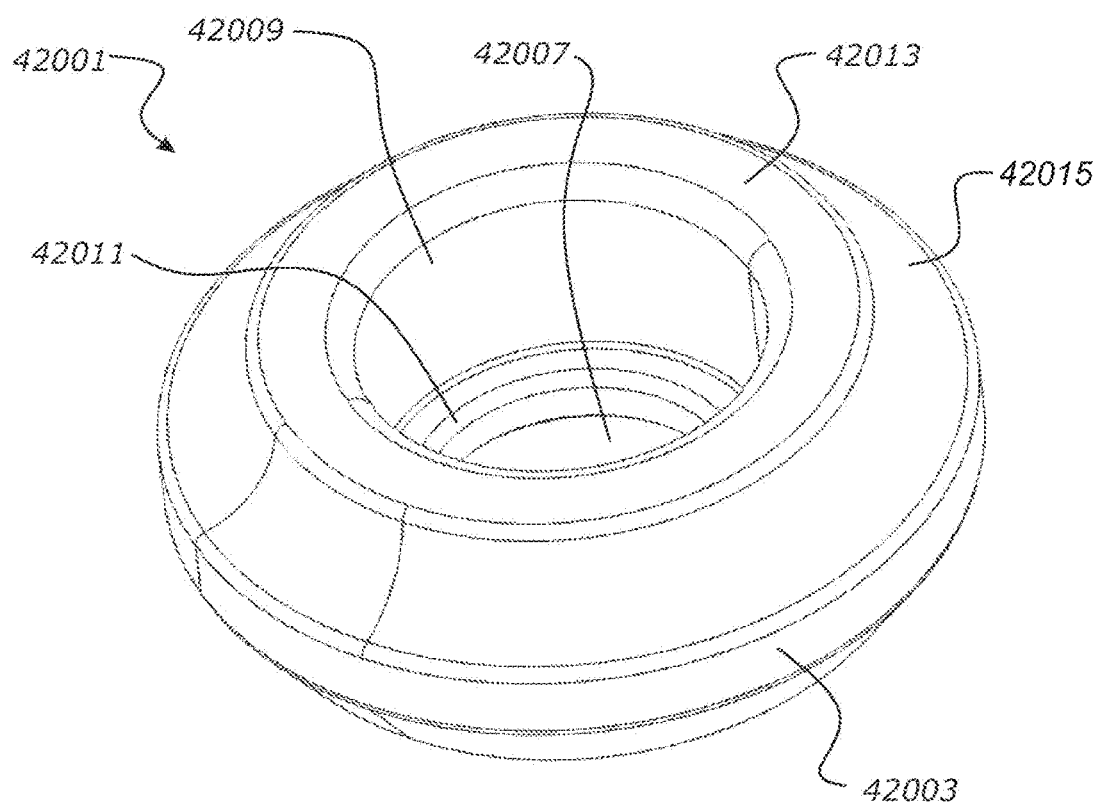
FIG. 42 is a perspective view of a bearing mount.

FIG. 42 shows a perspective view of a bearing mount 42001. The bearing mount 42001 is suitable for use with the flow generator 11 described herein. In particular, the bearing mount 42001 is suitable for use with a bearing 48001 that supports the shaft 33003 of the motor of the centrifugal blower. The bearing 48001 can include an inner race that can rotate with respect to an outer race.

The bearing mount 42001 has an annular body 42003, a collar 42005 extending from the annular body, and a central bore 42007 extending through the annular body and the collar. The central bore 42007 has a wall and a ledge 42011 extending radially inwardly from the wall of the central bore. The central bore defines a bearing rotational axis. The annular body and the collar are substantially concentric with the bearing rotational axis. The ledge is disposed near one end of the central bore and the collar is disposed near another end of the central bore.

Figure 47:
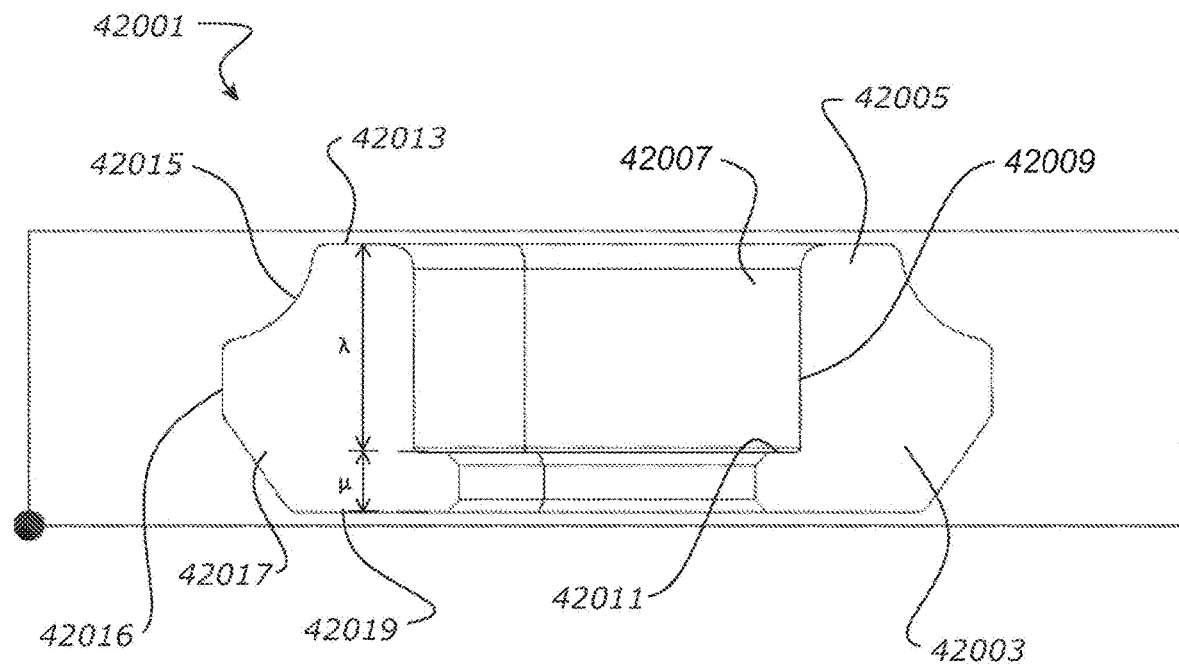
FIG. 47 is a cross sectional view of the bearing mount of FIG. 42.

The bearing mount 42001 also includes a tapered surface 42017, as shown in FIG. 47. When viewed from the side, the combination of the annular body 42003, collar 42005, and the tapered surface form a bearing mount 42001 having a top flat surface 42013, a recess 42015, a ridge 42016, the tapered surface 42017, then a flat bottom surface 42019.

The bearing mount 42001 is arranged to receive the bearing 48001 in the central bore 42007 such that the bearing 48001 is radially supported by the inner surface of the bearing mount 42001. The bearing 48001 is axially supported by the ledge 42011. The bearing mount 42001 acts to isolate the shaft 33003 and bearing 48001 from external vibrations, whilst preventing any vibrations sourced from the rotor 33006 or shaft 33003 from being transferred outside the shaft assembly.

Figure 41:
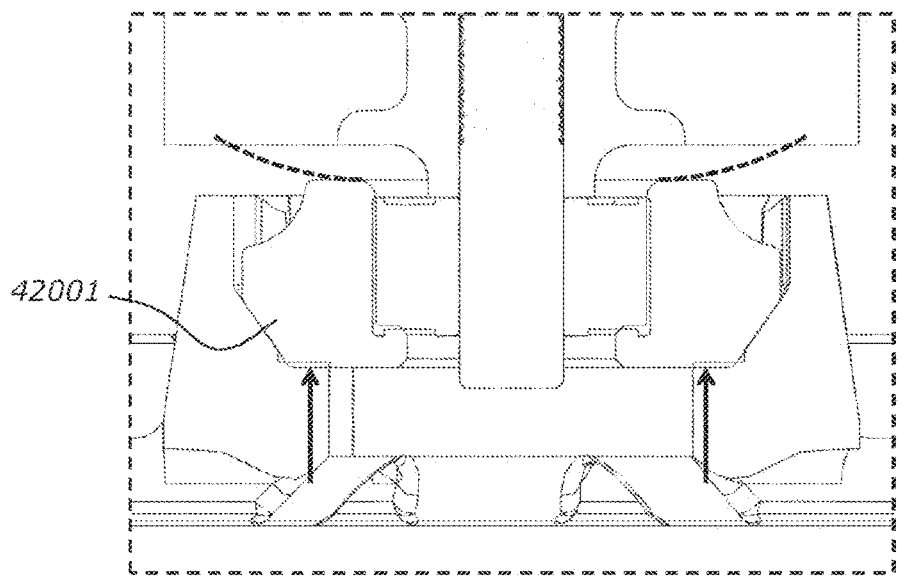
FIG. 41 is a view similar to FIG. 40 showing an extrapolation of bearing mount flex.

FIG. 41 shows the same detailed cross section of region A in FIG. 39. In the embodiment shown, the bearing mount 42001 fully retains the bearing 48001; that is, when the bearing mount 42001 and the bearing 48001 are assembled together, the bearing mount extends in a direction parallel to the axis of the shaft 33003 beyond the length of the bearing to hold the entire length of the bearing. In other words, the bore of the bearing mount spans and exceeds the entire length of the bearing. Holding the entire length of the bearing prevents, or at least substantially inhibits, the bearing 48001 popping out during assembly.

At least part of the bearing mount 42001 is arranged to flex or resiliently deform when a force is applied to the bearing mount 42001 to reduce the amount of the force that is translated to the bearing 48001 and therefore the shaft 33003

The at least part of the bearing mount 42001 is arranged to flex or resiliently deform such that the collar 42005 moves in a direction generally parallel to the bearing rotational axis when the force is applied to the bearing mount 42001.

The at least part of the bearing mount 42001 is arranged to flex or resiliently deform when a force is applied to the bearing mount 42001 such that the force translated to the bearing retained in the bearing mount 42001 remains generally constant as the force applied to the bearing mount increases beyond a threshold.

The recess 42015 reduces the likelihood that, when the bearing mount 42001 flexes under axial load, the bearing mount 42001 will contact the rotor. This recess 42015 is applied to both the bottom bearing mount flexing upwards and contacting the underside of the rotor, and the top bearing mount flexing downwards and contacting the top side of the rotor.

The collar is disposed on an opposite side of the annular body to the ledge 42011.

The ledge 42011 is substantially perpendicular to the bearing rotational axis.

At least the annular body comprises a silicone material. In the preferred embodiment, the entire bearing mount 42001 comprises a silicone material. The bearing mount 42001 is a unitary component. The silicone material is liquid silicone rubber (LSR). The silicone material may be a vibration resistant grade of silicone. The desired material properties include, but are not limited to:

Low compression set
High tear resistance
Thermally stable
High stability in $O_2$.

A circular bearing mount 42001 evenly distributes the load on the bearing mount 42001 along the structure that supports it (the bottom casing cap 25005 and/or the partition 33001).

Figure 43:
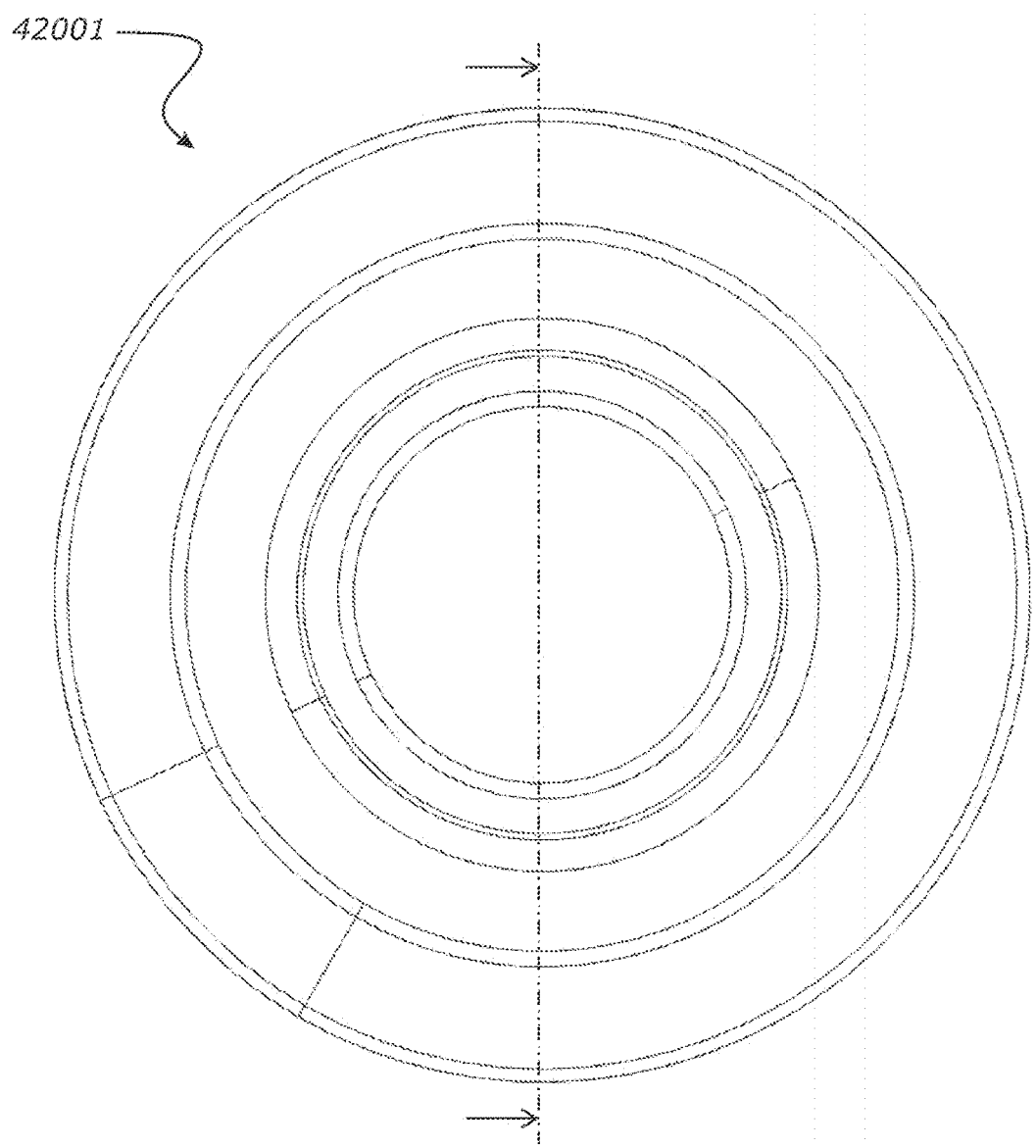
FIG. 43 is a top view of the bearing mount of FIG. 42.
Figure 44:
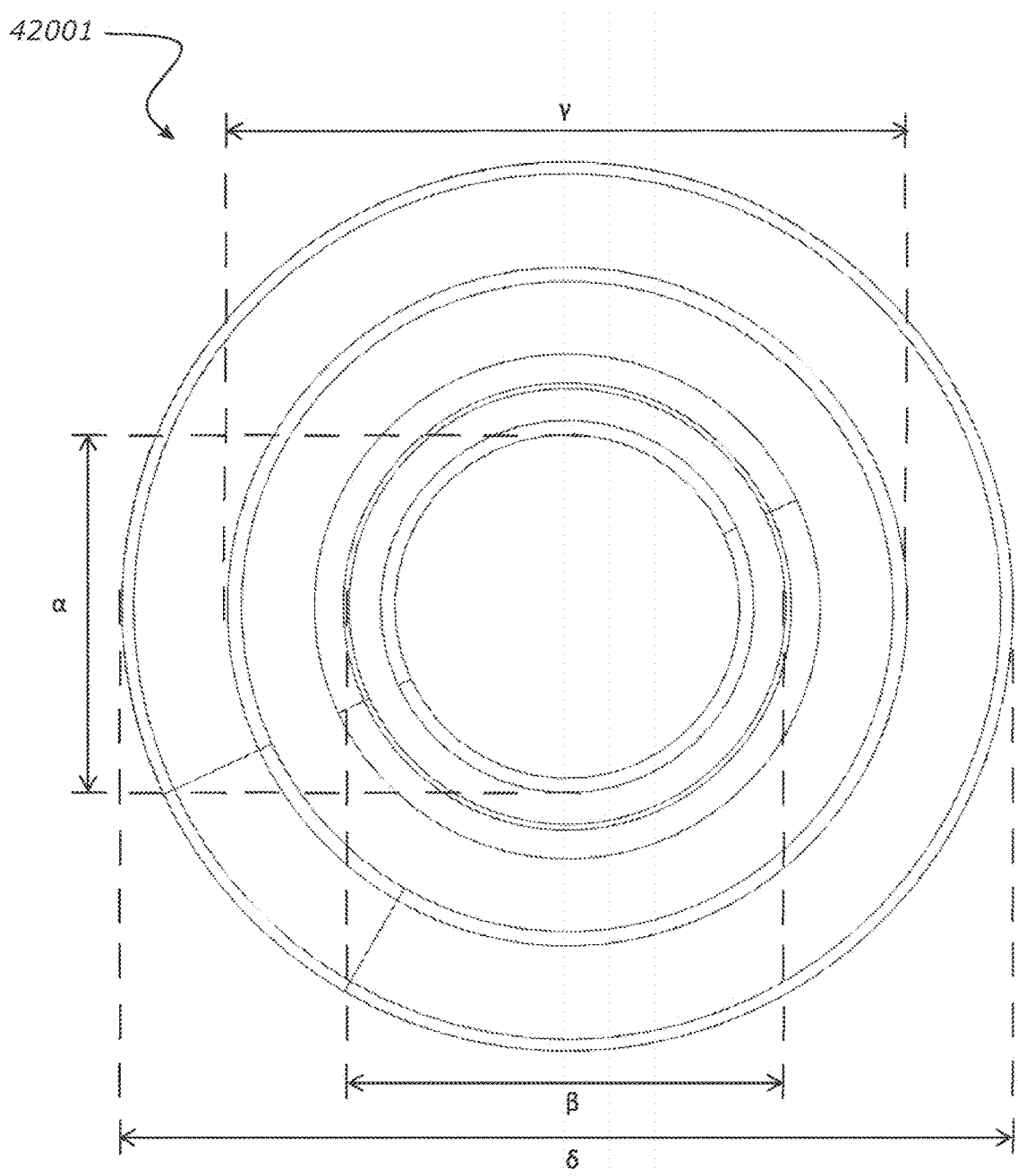
FIG. 44 is a top view of the bearing mount of FIG. 42 with dimensions.

FIG. 43 shows a top view of the bearing mount 42001 and FIG. 44 shows a top view of the bearing mount 42001 identifying some dimensions. In a preferred embodiment, the bearing mount 42001 has an external diameter $\delta=15.5$ mm. That diameter is the diameter of the annular body 42003. The central bore 42009 has a diameter (corresponding to the inner diameter of the bearing mount collar 42005) $\beta=7.8$ mm. The bearing mount collar 42005 has an outer diameter $\gamma=11.9$ mm. The bearing mount ledge 42011 defines an aperture with a diameter $\alpha=6$ mm.

In this configuration, $\delta>\gamma$ and $\beta>\alpha$, while $\beta<\gamma$. More specifically:

$$\delta:\alpha=2.6:1, \delta:\beta=2:1 \text{ and } \delta:\gamma=1.3:1$$

Providing a bearing mount 42001 having an annular body external diameter greater than the collar outer diameter ($\delta>\gamma$), results in a bearing mount having a lateral distance between the top of the bearing mount 42001 collar and the outer edge of the bearing mount 42001. This distance provides the recess 42015 around the edge of the bearing mount 42001. The recess allows the bearing mount 42001 to flex and behave as described around FIG. 41.

Providing a bearing mount 42001 having a bearing mount 42001 aperture greater than the bearing mount ledge aperture ($\beta>\alpha$), provides the bearing mount ledge 42011. As described earlier, this ledge 42011 supports the bearing 48001 in the axial direction.

Figure 45:
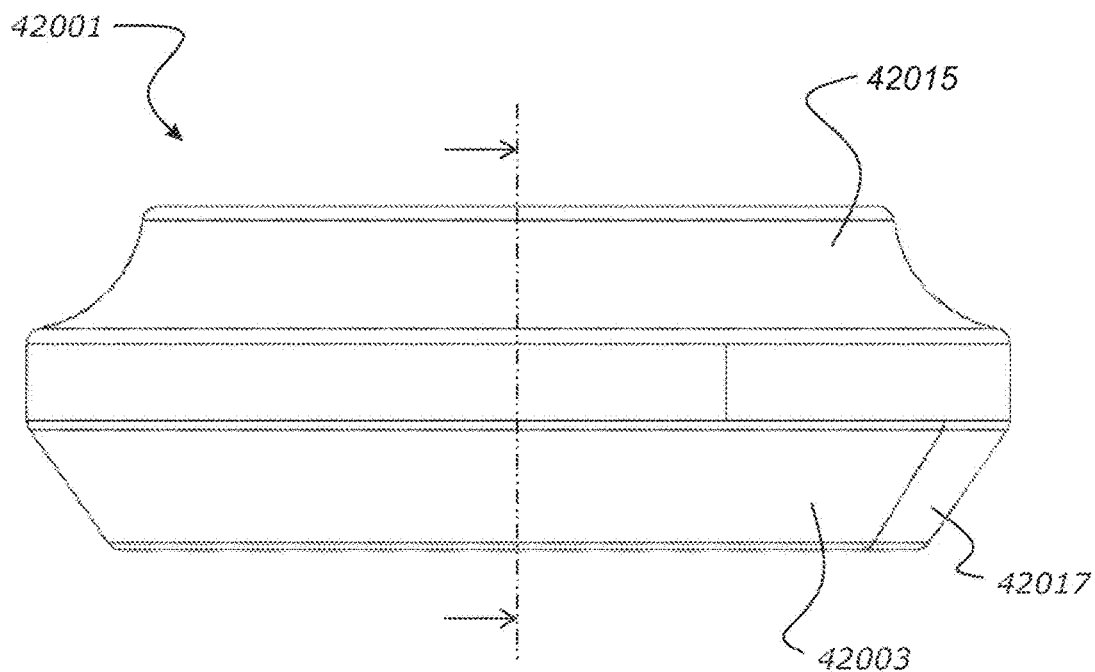
FIG. 45 is a side view of the bearing mount of FIG. 42.

FIG. 45 shows a side view of the bearing mount 42001. The bearing mount 42001 includes a tapered surface 42017. With reference to the orientation of FIG. 45, the surface tapers downwardly and inwardly towards the rotational axis. The tapered surface 42017 acts as an alignment feature, making it easier to place the bearing mount 42001 in the bearing mount 42001 recess of the bottom casing cap/partition.

Figure 46:
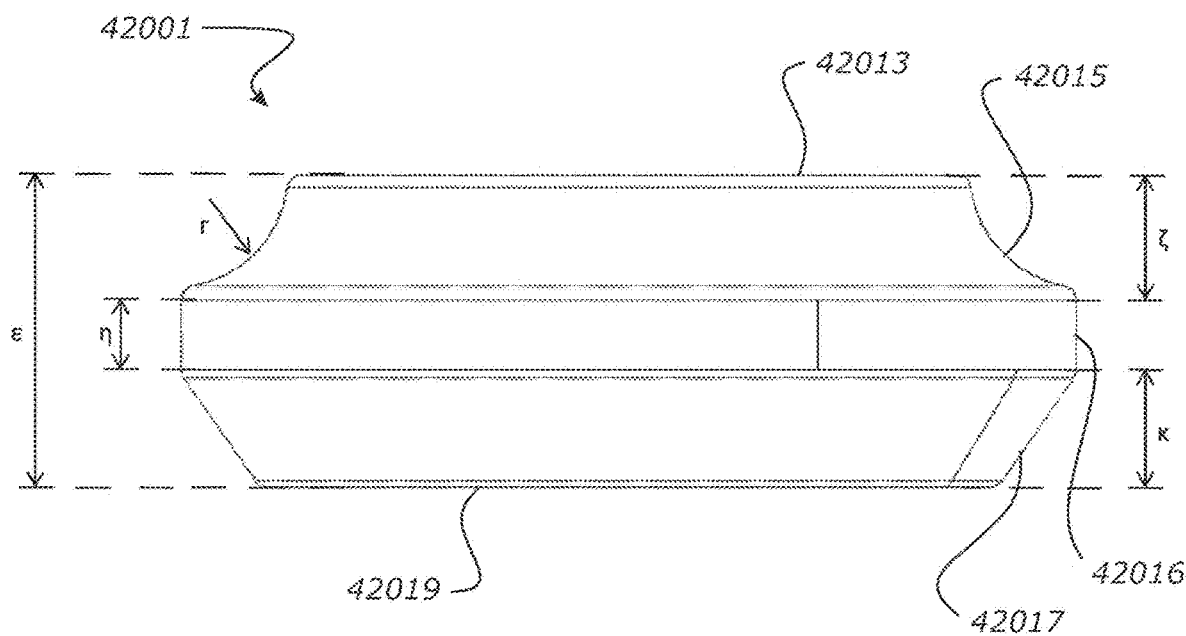
FIG. 46 is a side view of the bearing mount of FIG. 42 with dimensions.

FIG. 46 shows a side view of the bearing mount 42001 with dimensions shown. The bearing mount 42001 includes a total height $\varepsilon$, a collar height $\zeta$, a ridge height $\eta$ and a tapered surface height $\kappa$. In this configuration, $\varepsilon=5.4$ mm, $\zeta=2.2$ mm, $\kappa=2$ mm and $\eta=1.2$ mm. The recess has a radius $r=2$ mm.

In this configuration, the collar height is greater than the ridge height ($\zeta>\eta$) and the tapered surface height is greater than the ridge height ($\kappa>\eta$).

FIG. 47 shows the section plane identified in FIG. 43. The bearing mount 42001 has a bearing mount ledge thickness $\mu$ and a bearing mount 42001 aperture thickness $\lambda$. In this case, $\lambda=1.2$ mm and $\lambda=4.2$ mm. As a result, the ratio of $\lambda:\mu$ is 3.5:1.

It is preferred that the bearing mount ledge thickness µ is relatively small to reduce the profile of the bearing mount 42001, while also having sufficient thickness to retain and secure the bearing.

Figure 48:
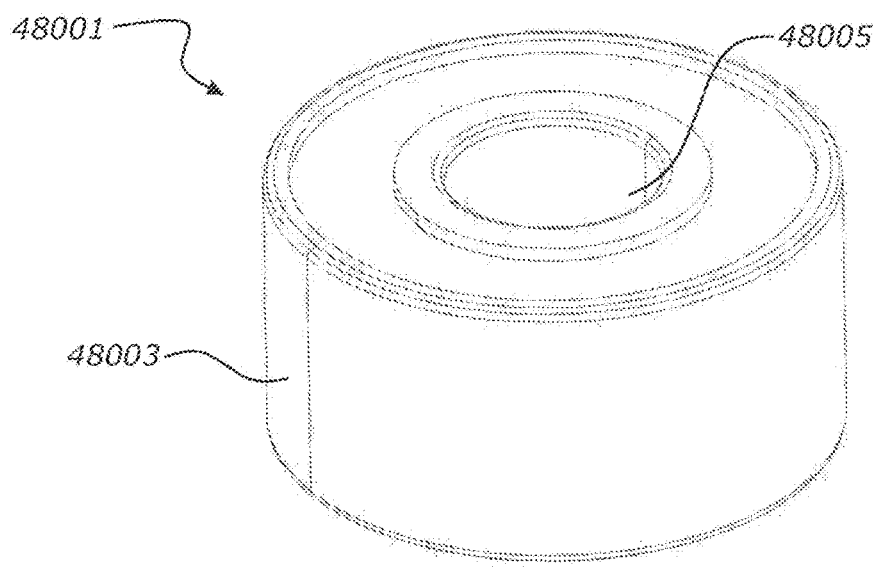
FIG. 48 shows a bearing.
Figure 49:
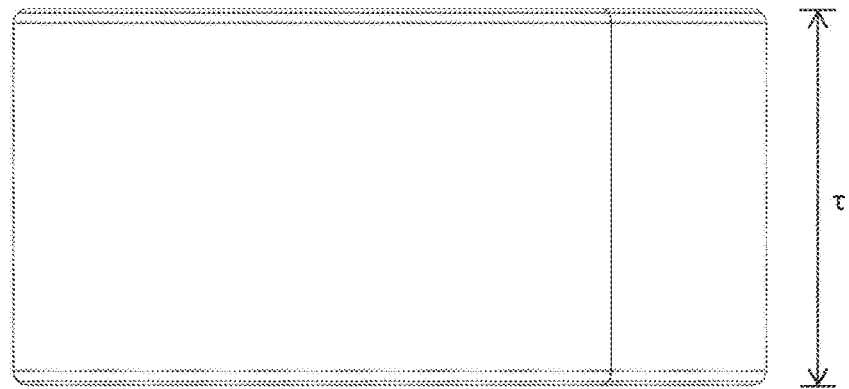
FIG. 49 is a side view of the bearing of FIG. 48.
Figure 50:
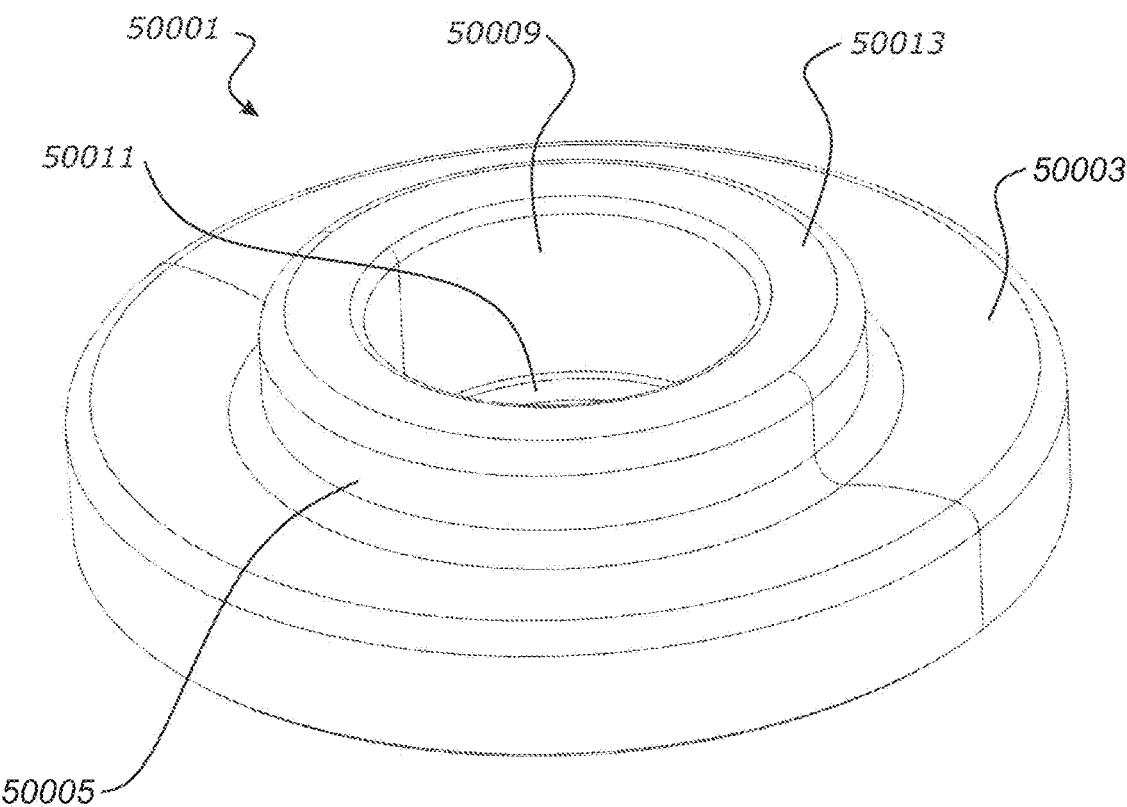
FIG. 50 is another embodiment of a bearing mount.

FIG. 48 shows a perspective view of a bearing 48001 that can fit into the bearing mount 42001 and FIG. 49 shows a side view of the bearing 48001. The bearing includes an inner race 48005 and an outer race 48003 that can rotate with respect to the inner race #. The bearing has an outer diameter dimension τ=4 mm. The ratio τ:∈ is therefore 4:5.4 or about 1:1.35, the ratio τ:µ is 4:1.2 or about 3.3:1, and the ratio τ:λ is 4:4.2 or about 1:1.05.

The τ:µ ratio of 4:1.2 results in a relatively thin ledge thickness µ minimising the profile of the bearing mount 42001, whilst being thick enough to provide enough support for the bearing.

It will be appreciated that one or more of the dimensions discussed above may be altered depending on different factors, such as the amount of vibration dampening required, or the size and shape of other components. However, the bearing mount will meet the conditions set out above, including:

δ>γ
β>α
β<γ

For example the annular body external diameter could be about 12.5 mm, about 13 mm, about 13.5 mm, about 14 mm, about 14.5 mm, about 15 mm, about 15.5 mm, about 16 mm, about 16.5 mm, about 17 mm, about 17.5 mm, about 18 mm, or about 15.5 mm.

The collar diameter could be about 9 mm, about 9.5 mm, about 10 mm, about 10.5 mm, about 11 mm, about 11.5 mm, about 12 mm, about 12.5 mm, about 13 mm, about 13.5 mm, about 14 mm, about 14.5 mm, or about 15 mm.

The central bore diameter could be about 5 mm, about 5.5 mm, about 6 mm, about 6.5 mm, about 7 mm, about 7.5 mm, about 8 mm, about 8.5 mm, about 9 mm, about 9.5 mm, about 10 mm, about 10.5 mm, or about 11 mm.

The ledge diameter could be 3 mm, about 3.5 mm, about 4 mm, about 4.5 mm, about 5 mm, about 5.5 mm, about 6 mm, about 6.5 mm, about 7 mm, about 7.5 mm, about 8 mm, about 8.5 mm, or about 9 mm.

The collar height could be 1.7 mm, about 1.8 mm, about 1.9 mm, about 2 mm, about 2.1 mm, about 2.2 mm, about 2.3 mm, 2.4 mm, about 2.5 mm, about 2.6 mm, or about 2.7 mm.

The ridge height could be 0.7 mm, about 0.8 mm, about 0.9 mm, about 1 mm, about 1.1 mm, about 1.2 mm, about 1.3 mm, 1.4 mm, about 1.5 mm, about 1.6 mm, or about 1.7 mm.

The tapered surface height could be about 1.5 mm, about 1.6 mm, about 1.7 mm, about 1.8 mm, about 1.9 mm, about 2 mm, about 2.1 mm, about 2.2 mm, about 2.3 mm, 2.4 mm, or about 2.5 mm.

The ledge thickness could be 0.7 mm, about 0.8 mm, about 0.9 mm, about 1 mm, about 1.1 mm, about 1.2 mm, about 1.3 mm, 1.4 mm, about 1.5 mm, about 1.6 mm, or about 1.7 mm.

The central bore thickness (or depth) to the top of the ledge could be about 2.3 mm, about 2.5 mm, about 3 mm, about 3.5 mm, about 4 mm, about 4.5 mm, about 5 mm, about 5.5 mm, about 6 mm, about 6.3 mm, or about 6.5 mm.

The total height of the bearing could be about 4 mm, about 4.5 mm, 5 mm, about 5.5 mm, about 6 mm, about 6.5 mm, about 7 mm.

The ratio of λ:µ could be about 3:1, about 3.5:1, about 4:1, about 4.5:1, about 5:1, about 5.5:1, about 6:1, about 6.5:1, about 7:1, about 7.5:1, about 8:1, about 8.5:1, about 9:1, about 9.5:1, about 10:1, about 10.5:1, about 11:1, about 11.5:1, about 12:1, about 12.5:1, about 13:1, about 13.5:1, about 14:1, about 14.5:1, about 15:1, about 15.5:1, or about 16:1. Ratios greater than or equal to 3.5:1 can be advantageous when a stronger or more rigid material is used to manufacture the bearing mount 42001. In this case, less material can be used in ledge 42011 relative to ratios with an antecedent below 3.5:1 whilst still providing similar performance supporting the bearing 48001. Ratios lower than 3.5:1 can be advantageous when a softer, less rigid and/or more flexible material is used to manufacture the bearing mount 42001. In this case, a thicker ledge is beneficial to provide sufficient support to the bearing 48001. The ratio τ:∈ could be about 1:0.95, about 1:1, about 1:1.05, about 1:1.1, about 1:1.15, about 1:1.2, about 1:1.25, about 1:1.3, about 1:1.35, about 1:1.4, about 1:1.45, about 1:1.5, about 1:1.55, about 1:1.6, about 1:1.65, about 1:1.7, or about 1:1.75. Ratios less than or equal to 1:1 can be advantageous in providing smaller profile bearing mount 42001. Ratios greater than 1:1 can be advantageous in providing increased support to the bearing 48001 within the bearing mount 42001.

The ratio τ:µ could be about 2.5:1, about 3:1, about 3.5:1, about 4:1, about 4.5:1, about 5:1, about 5.5:1, or about 6:1. Ratios greater than or equal to 3.3:1 can be beneficial in providing enhanced support to the bearing 48001. Ratios less than 3.3:1 can be beneficial in providing a reduced bearing mount 42001 profile, and requiring less material.

The ratio τ:λ could be about 2.4:1, about 2.5:1, about 3:1, about 3.5:1, about 4:1, about 4.5:1, about 5:1, about 5.5:1, or about 6:1. Ratios less than or equal to 1:1.05 can be beneficial in providing a reduced profile bearing mount 42001 requiring less material. Ratios greater than 1:1.5 can advantageously provide additional support to the bearing 48001 or a more resilient and/or stiffer bearing mount 42001 where desired.

FIGS. 50 to 58 show a second embodiment of a bearing mount 50001 suitable for use with the flow generator 11 described herein.

This embodiment of the bearing mount 50001 has similar features and functions to the features and functions of the first bearing mount 42001 described above. The features and functions of the second embodiment bearing mount 50001 that are different to those of the first embodiment are described below.

Figure 56:
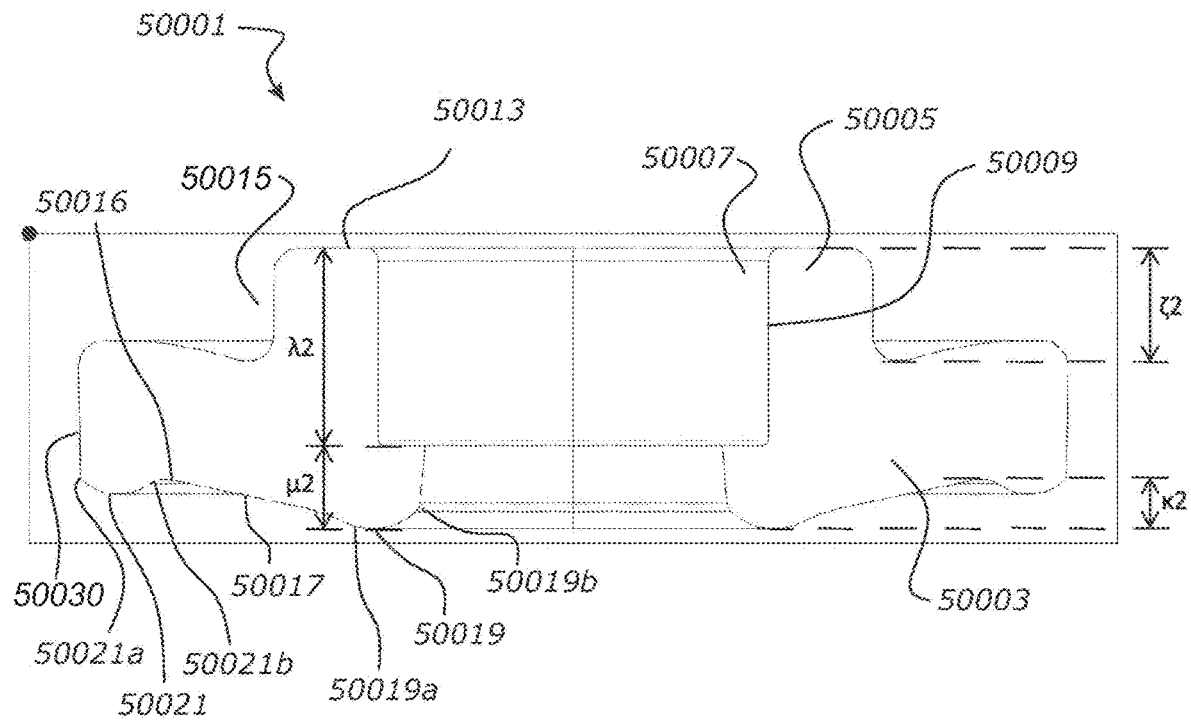
FIG. 56 shows a bearing mount section plane.

The differences between this second embodiment of the bearing mount 50001 and the first embodiment of the bearing mount 42001 are:

The annular body 50003 extends outwardly at a non-perpendicular angle relative to the bearing rotational axis. The annular body 50003 includes an outer protruding rim or lip 50021, as shown in FIG. 56. The outer protruding rim 50021 is located at or near the outer periphery of the annular body 50003. The outer protruding rim 50021 has a convex curved profile, when viewed from below when viewed in the orientation of FIG. 56. The outer rim 50021 has an outer edge 50021a and an inner edge 50021b. The outer edge 50021a joins sharply with the outer edge 50015 of the annular body 50003. The inner edge transitions into a tapered surface 50017 via a concave curved surface 50016 (when viewed from below). The tapered surface 50017 extends inwardly and downwardly when viewed in the orientation of FIG. 57. The tapered surface 50017 transitions into an inner rim 50019.

The inner rim 50019 has a convex curved profiled, when viewed from below. The inner rim 50019 has an outer edge 50019a and an inner edge 50019b. The inner edge joins sharply with the inner surface of the annular body. The thickness of the annular body 50003 remains generally constant from the outer surface 50015 to where it meets the collar 50005. Accordingly, the top surface of the body is a tapered surface that extends inwardly and downwardly when viewed in the orientation of FIG. 57. The annular body 50003 transitions smoothly via a concave curve into the collar 50005. These differences from the first embodiment also lead to a differently shaped recess 50015 and collar 50005.

Figure 57:
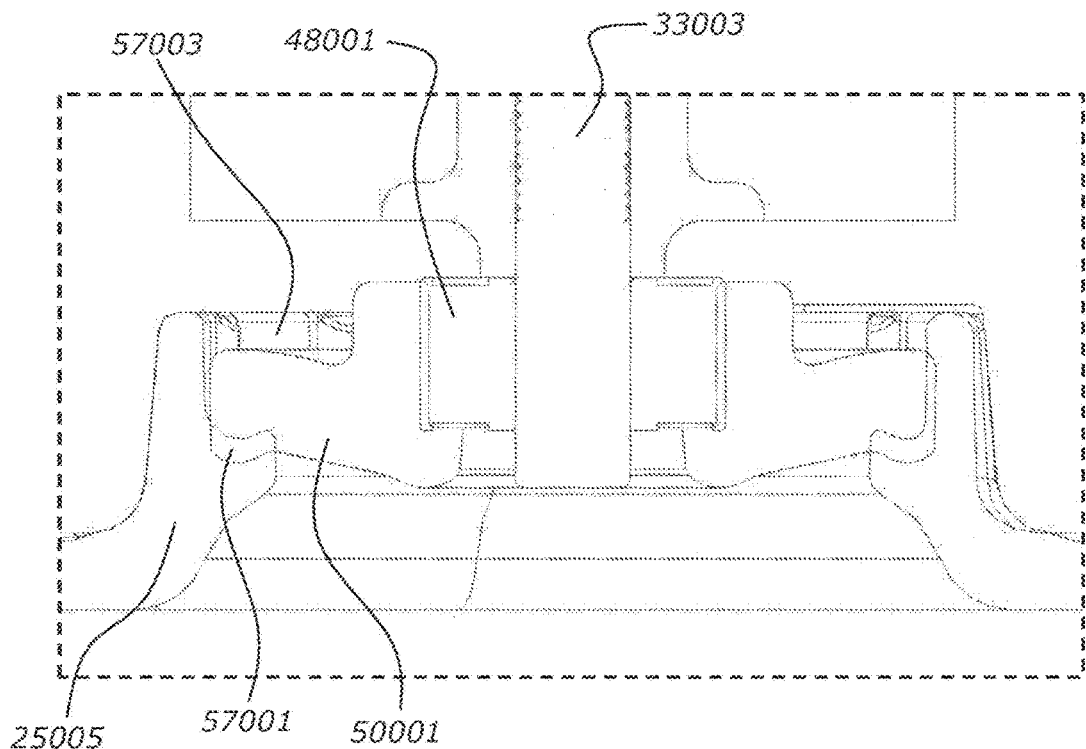
FIG. 57 is a detailed cross-sectional view of the flow generator with the bearing mount of FIG. 50.

FIG. 57 shows an overlap 57001 between the bearing mount 50001 and the bearing mount recess 57003 supporting the bearing mount 50001. That overlap 5700a represents the interference fit between the components.

Figure 51:
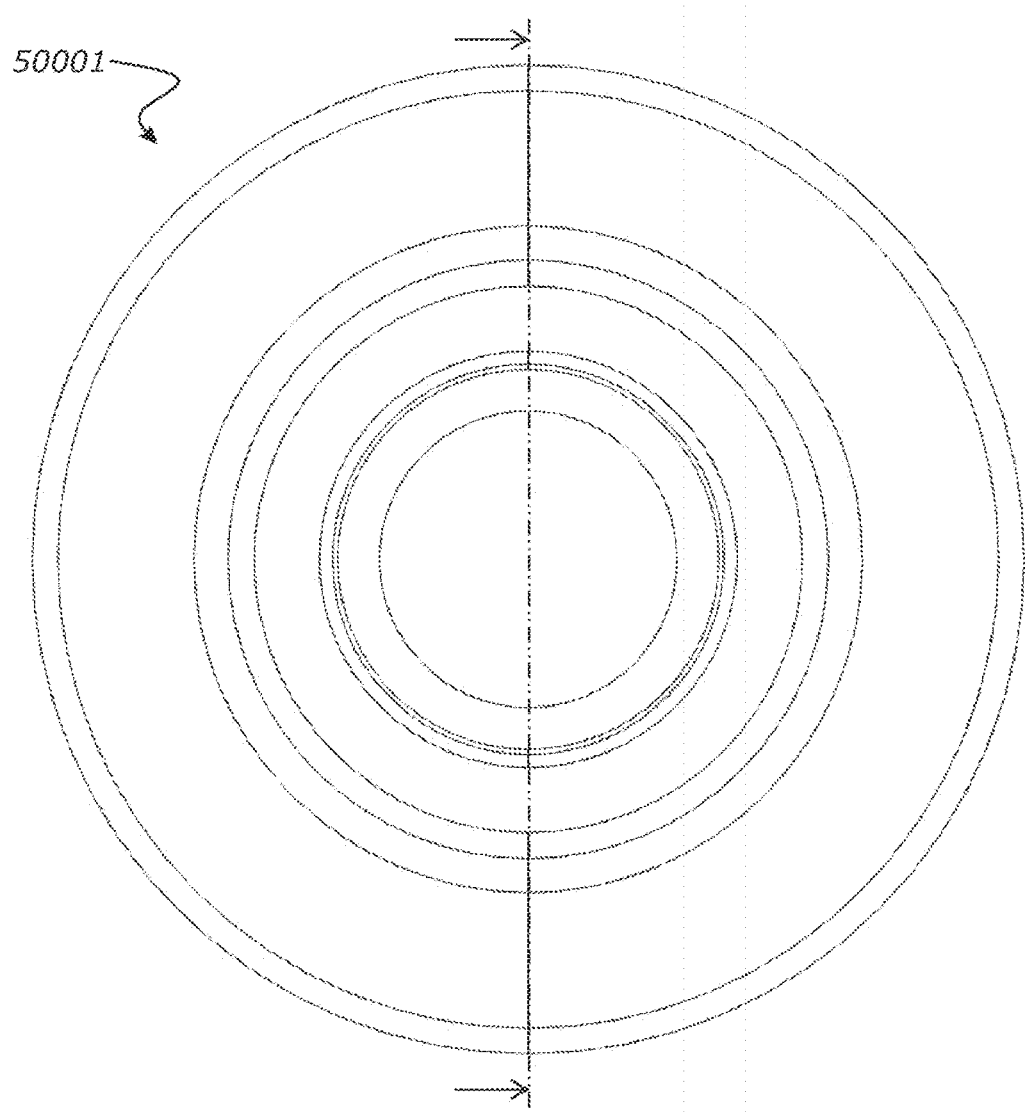
FIG. 51 is a top view of the bearing mount of FIG. 50.
Figure 52:
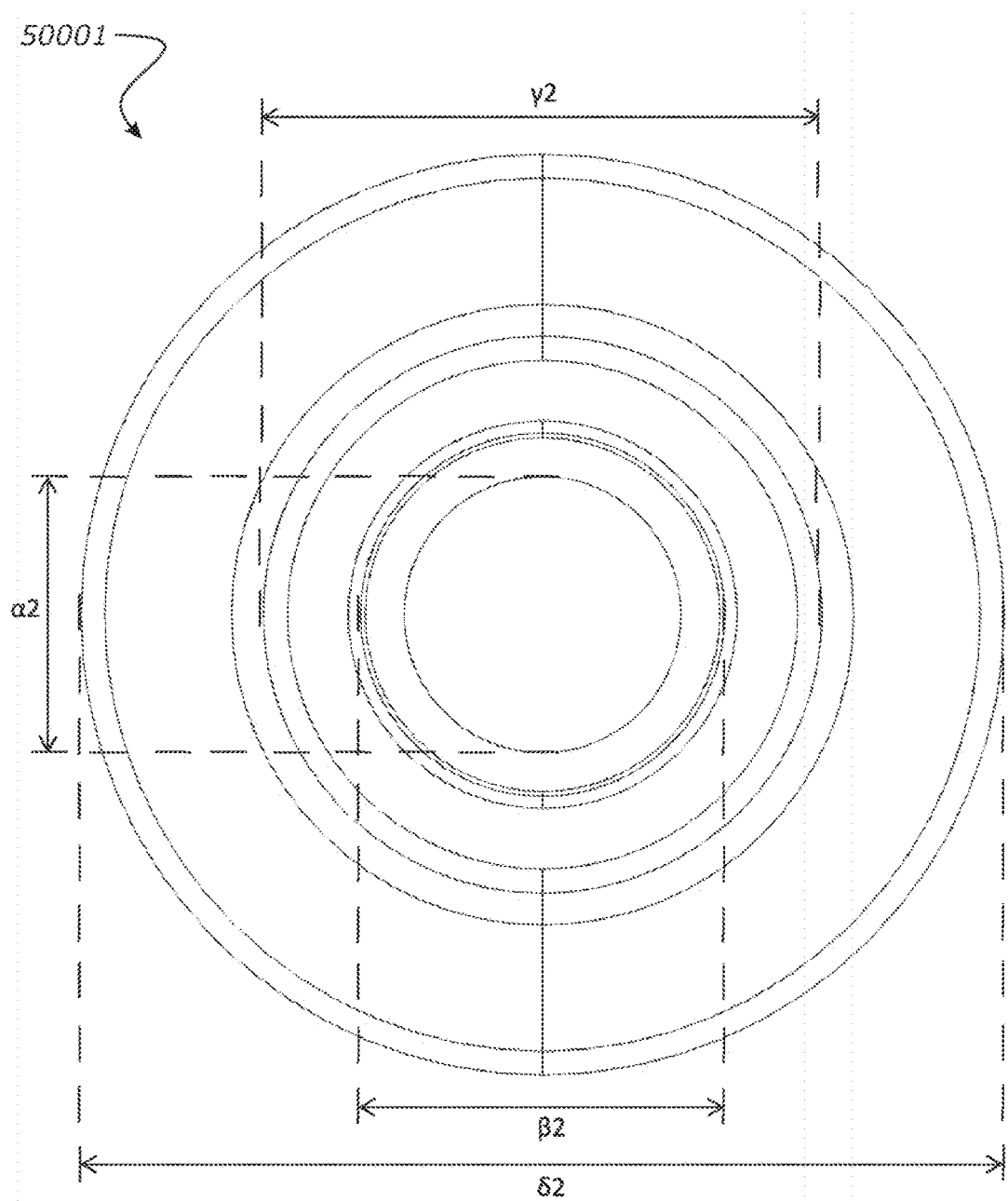
FIG. 52 is a top view of the bearing mount of FIG. 50 with dimensions.
Figure 53:
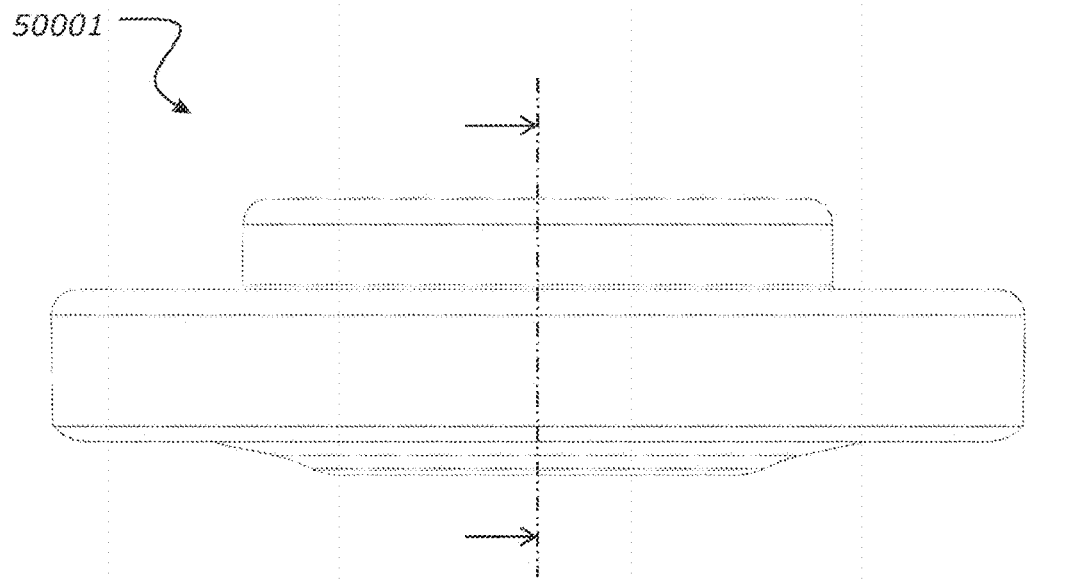
FIG. 53 is a side view the bearing mount of FIG. 50.
Figure 54:
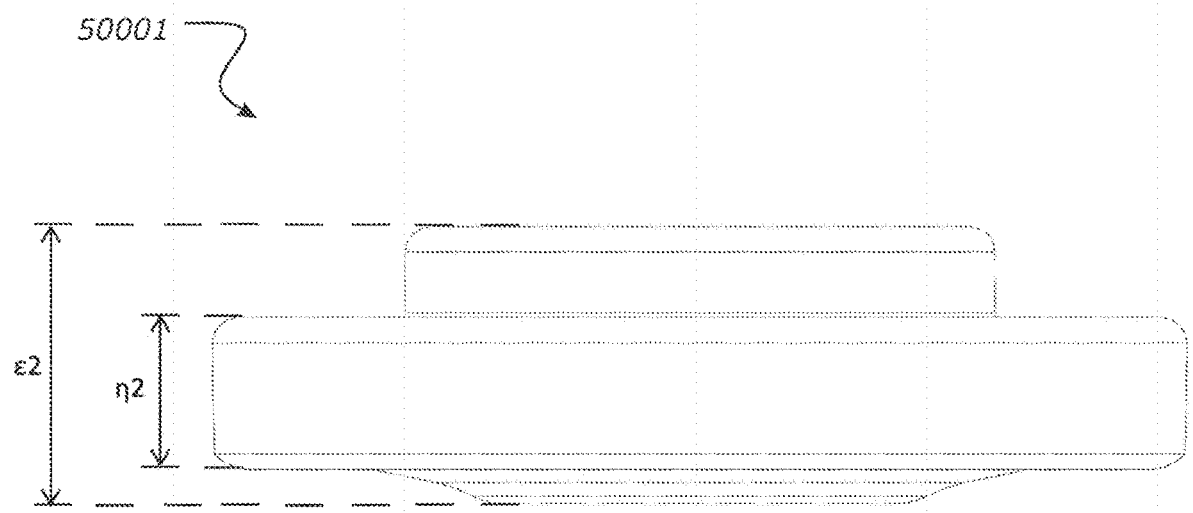
FIG. 54 is a side view the bearing mount of FIG. 50 with dimensions.
Figure 55:
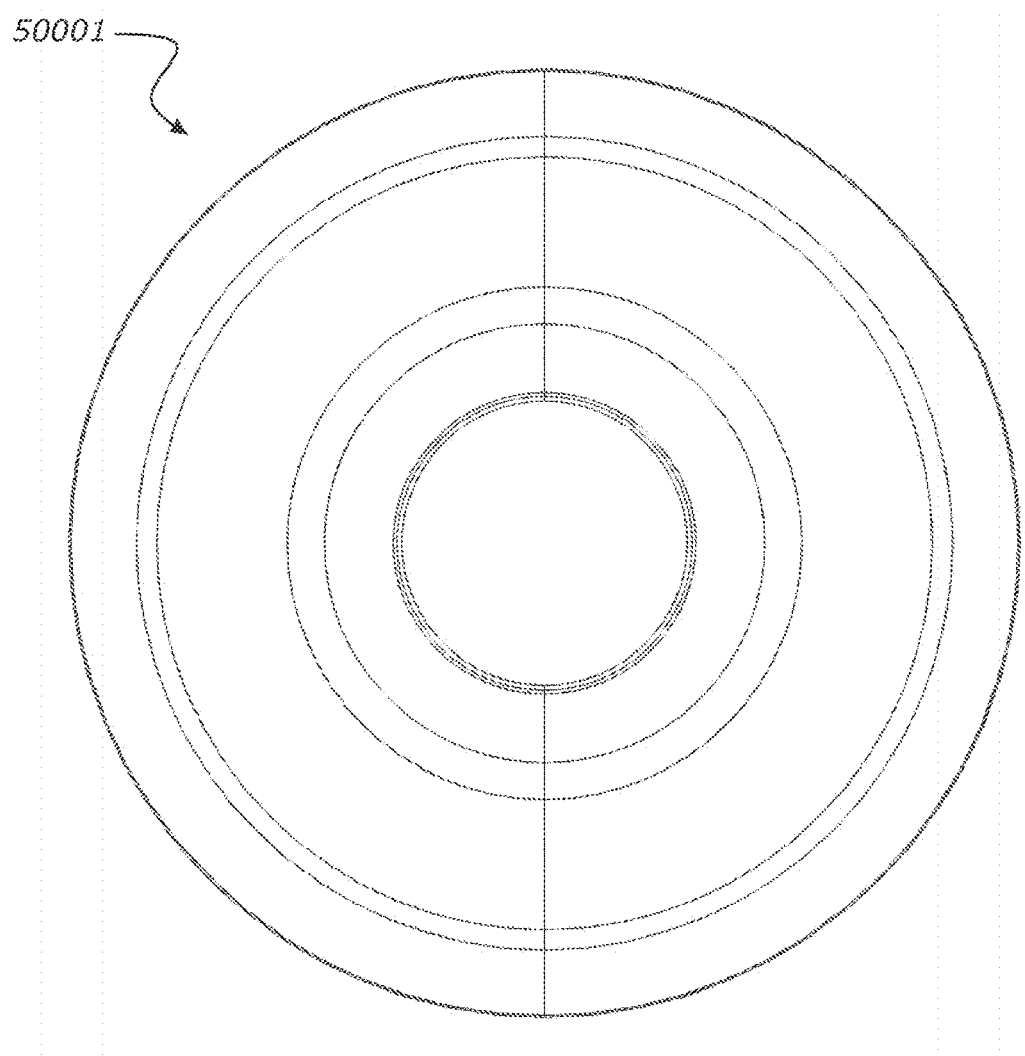
FIG. 55 shows a bearing mount bottom surface.

FIG. 51 shows a top view of the second embodiment of the bearing mount and identifies a section plane that can be taken. FIG. 52 shows a top view of the bearing mount identifying some dimensions.

The annular body 50003 has an external diameter $\delta 2 = 18.9$ mm, the central bore has a diameter (corresponding to the inner diameter of the bearing mount collar) $\beta 2 = 7.5$ mm, the collar has an outer diameter $\gamma 2 = 11.5$ mm and the bearing mount ledge defines a bearing mount ledge aperture with a diameter $\alpha 2 = 5.7$ mm.

Again, in this configuration, $\delta 2 > \gamma 2$ and $\beta 2 > \alpha 2$, while $\beta 2 < \gamma 2$. More specifically:

$$\delta 2 : \alpha 2 = 3.3:1, \delta 2 : \beta 2 = 2.5:1 \text{ and } \delta 2 : \gamma 2 = 1.6:1$$

Again, preferably $\delta > \gamma$ and $\beta > \alpha$ for the reasons discussed in the previous embodiment.

As shown in FIG. 57, the bearing mount 50001 is supported within the bearing mount recess 57003 of the bottom casing cap 25005. The bearing mount 50001 is arranged to deform under load. $\delta 2 : \gamma 2$ provides advantageous deformation characteristics. The bearing mount 50001 can flex sufficiently to provide vibration and force isolation to the bearing 48001, whilst being stiff or hard enough to retain the bearing 48001 in place minimising the extent of excess deformation detrimental to the rotational characteristics or the efficiency of the motor 402.

For example the annular body external diameter could be about 16 mm, about 16.5 mm, about 17 mm, about 17.5 mm, about 18 mm, about 18.5 mm, about 19 mm, about 19.5 mm, about 20 mm, about 20.5 mm, about 21 mm, about 21.5 mm, or about 22 mm.

The collar diameter could be about 8.5 mm, about 9 mm, about 9.5 mm, about 10 mm, about 10.5 mm, about 11 mm, about 11.5 mm, about 12 mm, about 12.5 mm, about 13 mm, about 13.5 mm, about 14 mm, or about 14.5 mm.

The central bore diameter could be about 4.5 mm, about 5 mm, about 5.5 mm, about 6 mm, about 6.5 mm, about 7 mm, about 7.5 mm, about 8 mm, about 8.5 mm, about 9 mm, about 9.5 mm, about 10 mm, or about 10.5 mm.

The ledge diameter could be 3 mm, about 3.5 mm, about 4 mm, about 4.5 mm, about 5 mm, about 5.5 mm, about 6 mm, about 6.5 mm, about 7 mm, about 7.5 mm, about 8 mm, about 8.5 mm, or about 9 mm.

The collar height could be 1.7 mm, about 1.8 mm, about 1.9 mm, about 2 mm, about 2.1 mm, about 2.2 mm, about 2.3 mm, 2.4 mm, about 2.5 mm, about 2.6 mm, or about 2.7 mm.

The ridge height could be 0.7 mm, about 0.8 mm, about 0.9 mm, about 1 mm, about 1.1 mm, about 1.2 mm, about 1.3 mm, 1.4 mm, about 1.5 mm, about 1.6 mm, or about 1.7 mm.

The tapered surface height could be about 1.5 mm, about 1.6 mm, about 1.7 mm, about 1.8 mm, about 1.9 mm, about 2 mm, about 2.1 mm, about 2.2 mm, about 2.3 mm, 2.4 mm, or about 2.5 mm.

The ledge thickness could be 0.7 mm, about 0.8 mm, about 0.9 mm, about 1 mm, about 1.1 mm, about 1.2 mm, about 1.3 mm, 1.4 mm, about 1.5 mm, about 1.6 mm, or about 1.7 mm.

The central bore thickness (or depth) to the top of the ledge could be about 2.3 mm, about 2.5 mm, about 3 mm, about 3.5 mm, about 4 mm, about 4.5 mm, about 5 mm, about 5.5 mm, about 6 mm, about 6.3 mm, or about 6.5 mm.

The total height of the bearing could be about 4 mm, about 4.5 mm, 5 mm, about 5.5 mm, about 6 mm, about 6.5 mm, about 7 mm.

The ratio of $A2:\mu 2$ could be about 3:1, about 3.5:1, about 4:1, about 4.5:1, about 5:1, about 5.5:1, about 6:1, about 6.5:1, about 7:1, about 7.5:1, about 8:1, about 8.5:1, about 9:1, about 9.5:1, about 10:1, about 10.5:1, about 11:1, about 11.5:1, about 12:1, about 12.5:1, about 13:1, about 13.5:1, about 14:1, about 14.5:1, about 15:1, about 15.5:1, or about 16:1. The ratio $\tau : \in$ could be about 1:0.95, about 1:1, about 1:1.05, about 1:1.1, about 1:1.15, about 1:1.2, about 1:1.25, about 1:1.3, about 1:1.35, about 1:1.4, about 1:1.45, about 1:1.5, about 1:1.55, about 1:1.6, about 1:1.65, about 1:1.7, or about 1:1.75.

The ratio $\tau : \mu 2$ could be about 2.5:1, about 3:1, about 3.5:1, about 4:1, about 4.5:1, about 5:1, about 5.5:1, or about 6:1.

The ratio $\tau : \lambda 2$ could be about 2.4:1, about 2.5:1, about 3:1, about 3.5:1, about 4:1, about 4.5:1, about 5:1, about 5.5:1, or about 6:1.

The partition 33001 is connected to the bottom casing cap 25005 via a number of screws. When the screws are tightened, there can be a variability in the amount of torque applied. Rigid bearing mounts would result in different forces being transferred to the bearings and shaft 33003 from the rest of the flow generator depending on the tightness of the partition 33001 and bottom casing cap 25005 connection. This can lead to a variety of disadvantageous features such as an imbalanced bearing, shaft, rotor and/or impeller which can lead to higher noises, lower efficiencies and a lower operating lifetime of the assembly.

By providing bearing mounts that can deform, the bearing mounts mitigate this effect of variability of tightness. Securing the partition to the bottom casing cap secures the bearing mounts within the motor assembly. As the partition and the bottom casing cap are tightened, forces resulting from the tightening are transferred to the bearing mounts and the bearings. The illustrated bearing mounts are configured to exhibit a preferential load transfer to the bearings as a result of the tightening. As the bottom casing cap and the partition are tightened, the force transferred through the bearing mounts to the bearings increases to a threshold value at a threshold tightness. After this force threshold is reached (corresponding to the threshold tightness between the partition and the bottom casing cap), the bearing mounts are configured to deform to minimise the transfer of any additional load to the bearings and therefore the shaft of the motor 402. This behaviour is a function of the shape of the bearing mounts as illustrated. The partition and the bottom casing cap may be tightened further, however the bearing mounts will flex to insulate the bearings and the shaft from the additional force exerted on the bearing mounts rather than transferring the forces through the bearing mounts to the bearings and/or shaft.

If the axial force on the bearings increases beyond the threshold, the bearing mounts will deform so that, the force will act on the bearing mount and excess will not be transferred to the bearing, or the excess transferred to the bearing is minimised.

FIG. 57 shows a section plane of a flow generator assembly including the second bearing mount embodiment 50001. Again the bearing mount 50001 is suspended within the bearing mount recess of the bottom casing cap 25005. The bearing mount recess includes a cooperating cavity that cooperates with the outer rim 50021 of the bearing mount 50001 to assist in securing it in place.

When the partition 33001 is connected to the bottom casing cap 25005, the bearing mount 50001 is able to flex to reduce or dampen the effect of the tightening parts on the bearing and shaft 33003 of the blower. In addition to this, the recess 57003 again reduces the likelihood that the bearing mount will flex to the point that its periphery will contact the rotor. Similar or the same behaviour occurs at the bearing mount 50001 in the bearing mount recess of the partition.

As the bearing mount flexes, the outer rim can pivot within the cooperating cavity. When the outer rim pivots, the surface of the outer rim will slide relative to the surface of the recess. With reference to FIG. 56, the outer rim will pivot about a point spaced inwards from the periphery of the bearing mount so that the periphery of the bearing mount moves vertically (in a direction parallel to the axis of the central bore). This prevents unusual flexing of the ends of the bearing mount for more consistent behaviour under compression.

Figure 58:
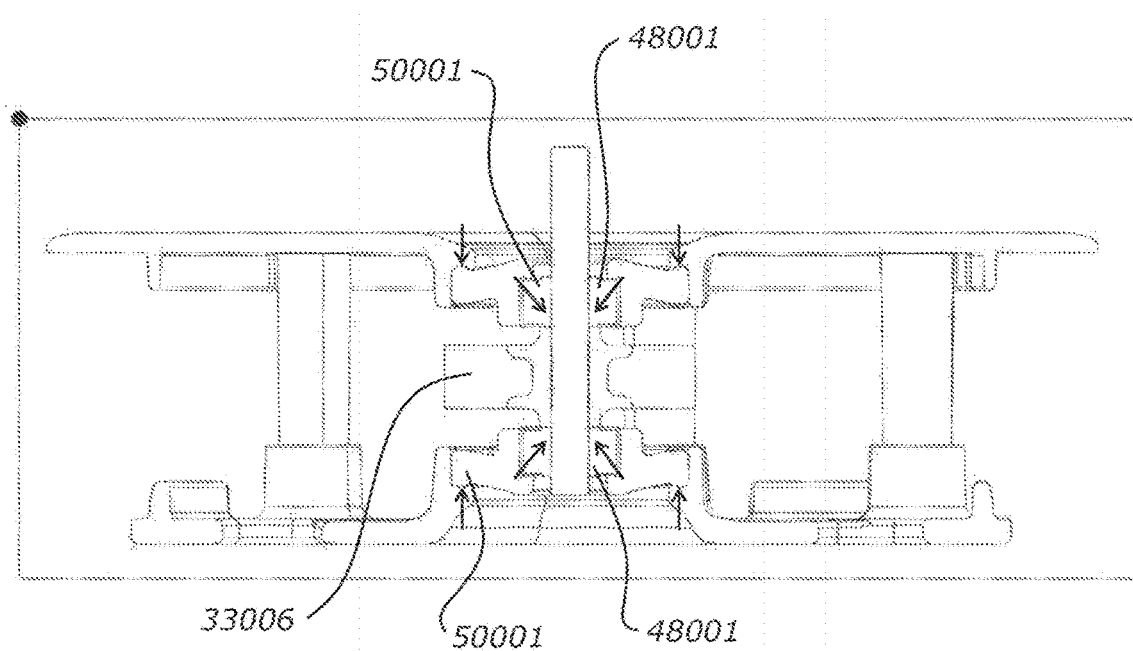
FIG. 58 is a cross-sectional view of the flow generator of FIG. 25 showing the preload applied to the bearings.

The profile and physical properties of the bearing mount provide a preload, or biasing force, to the bearings 48001 when the flow generator is assembled. The preload increases the lifetime of the bearings 48001. FIG. 58 shows the preloaded bearings 48001.

When the bottom casing cap 25005 is secured to the partition 33001, a preload is introduced into the bearing mount via the labelled bearing mount compression force, which in turn introduces a preload to the bearings. The preload introduced onto the bearings 48001 can be diagonal (relative to the rotational axis of the bearing) due to the deformation of the bearing mount. The preload eliminates the clearance that is designed into standard bearings. Almost all radial bearings are made with a clearance or space between their components to allow for free movement. This space, if not taken up by a preload can allow the rolling elements to slide rather than roll, or can allow for the inner and outer bearing races to misalign. The preload introduced via the bearing mounts provides bearing system rigidity, reduced vibration and improved bearing life.

Figure 59:
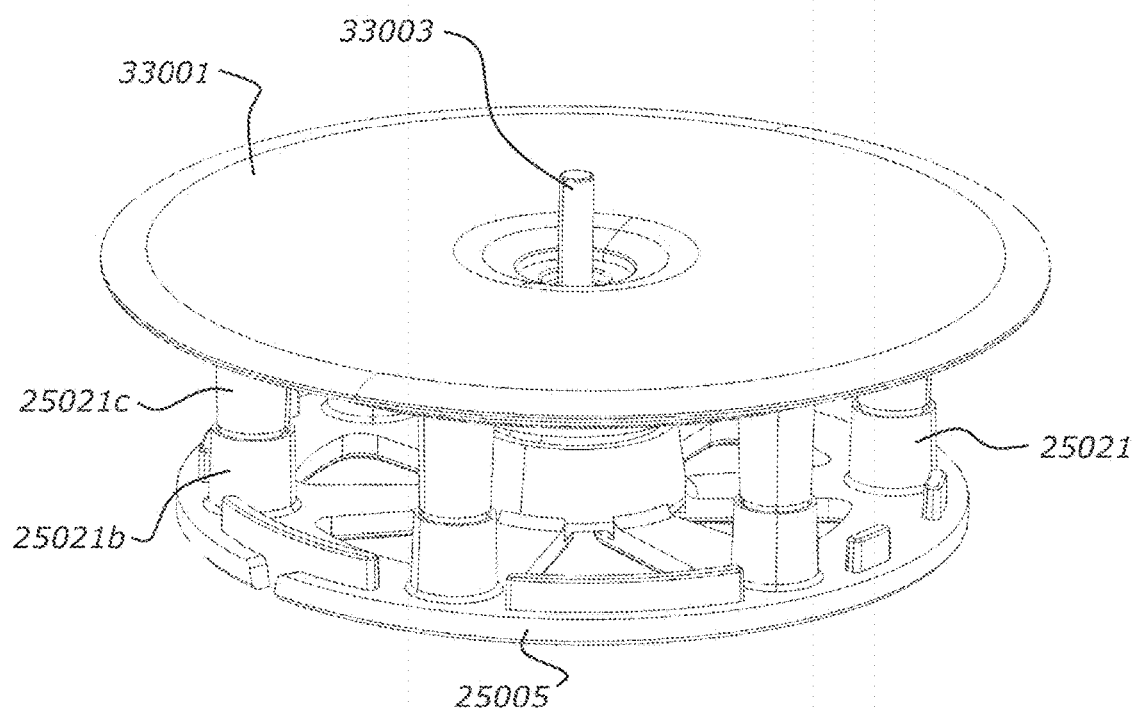
FIG. 59 is a perspective view showing the partition and bottom casing cap connected together.

FIG. 59 is a perspective view of the bottom casing cap 25005 of FIG. 58 assembled with the partition 33001. The bottom casing 25003, which fits between the bottom casing cap 25005 and the partition 33001, is hidden. Other internal components of the flow generator are also hidden in FIG. 59. The partition 33001 is screwed to the bottom casing cap 25005 to secure the parts in place. This in turn secures the bottom casing 25003 in place between the bottom casing cap 25005 and the partition 33001, although the bottom casing is not shown in FIG. 59.

Figure 60:
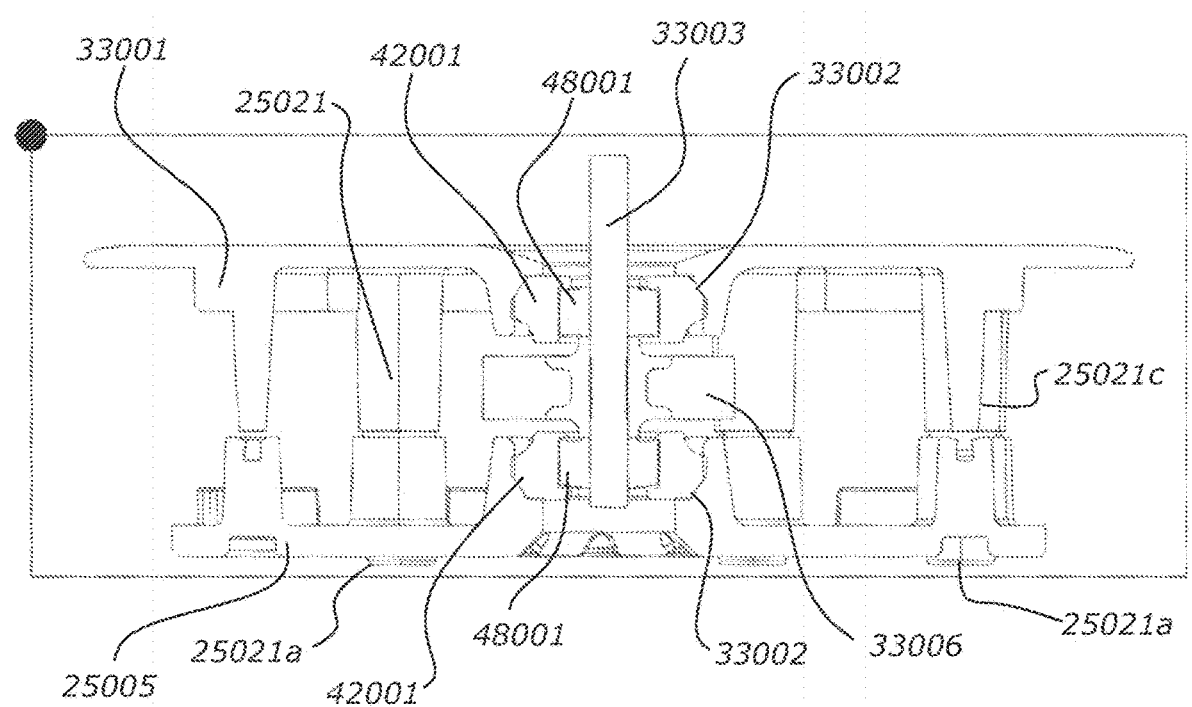
FIG. 60 is a section plane of FIG. 59.

FIG. 60 shows a section plane of the arrangement of FIG. 59, including details of the fastening mechanisms 25021 between the partition 33001 and the bottom casing cap 25005. FIG. 60 shows the screws 25011a that extend through clearance apertures provided in bosses 25021b in the bottom casing cap 25005. The screws 25021a are in threaded engagement with threaded apertures provided in bosses 25021c in the partition 33001.

Figure 61:
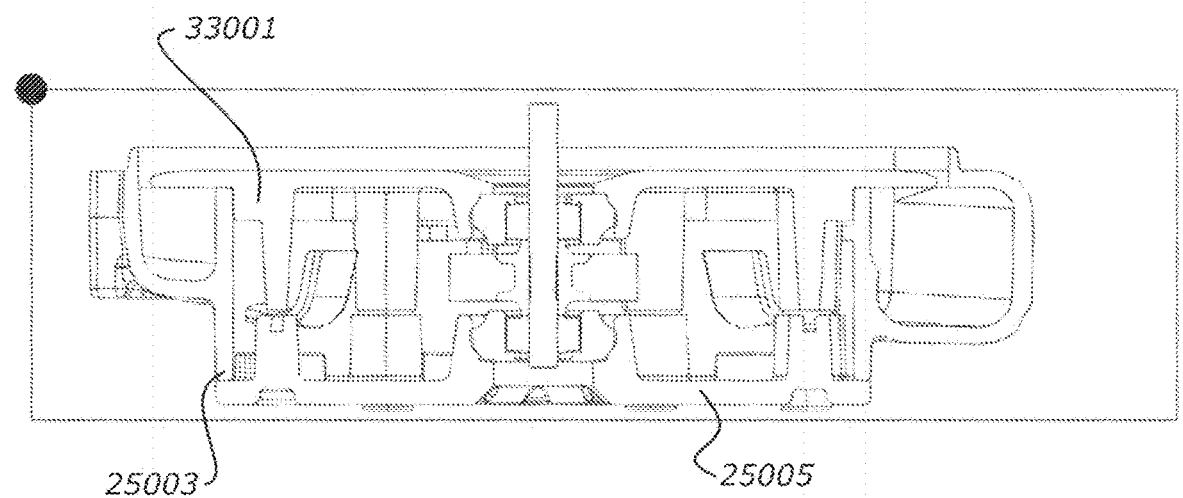
FIG. 61 is a cross-sectional view showing the bottom casing cap, partition, and bottom housing.

FIG. 61 shows a section plane of the arrangement of FIGS. 59 and 60 also showing the bottom casing 25003. The bottom casing 25003 is effectively sandwiched between the bottom casing cap 25005 and the partition 33001 at its rim, sealing and preventing, or at least substantially inhibiting, airflow from the inlet aperture 25007 and volute into the motor assembly. The combination of the bottom casing 25002, in particular the sealing inner wall 35001, and the partition 33001 are secured together such that an isolated space 62005 in the centre of the bottom casing is provided to house the motor 402. The motor is then sealed from the air flow through the volute.

FIG. 62 shows a section plane of the arrangement of FIGS. 59 to 61 also showing the top casing 25002. The bottom casing 25003 is secured to the top casing using the fastening mechanism (3 screw arrangements). Using screws means that if the material of the bottom casing 25003 and/or top casing 25002 degrades, that degradation is less likely to affect the assembly integrity.

With reference to FIG. 63, the bearing mounts support the bearings 48001 and shaft 33003 in each of the bearing mount recesses. In addition, when engaged, the upper bearing mount provides a seal around the portion of the shaft 33003 extending through the partition 33001.

The combination of various features of the present invention provide advantages, which can be achieved using a single impeller. Using a lightweight/low inertia impeller (e.g. by removing some or all of the shroud and/or reducing blade material) reduces imbalance of the impeller due to manufacturing tolerances. Previously, after manufacture and during assembly of a blower, it has been necessary to remove/add material to the impeller to improve balancing. The lightweight nature of the impeller means that any small imbalance can be tolerated without requiring rectification. Coupled to this, where the imbalance is not small enough, the resilient/flexible bearing mounts can compensate for any imbalance in the impeller. As the impeller is lightweight enough, any imbalance is of a small enough magnitude to be compensated for by the bearing mounts, without the need for altering the weight of the impeller during assembly.

The lightweight construction also allows for a larger diameter impeller, which in turn provides higher tip speed for a particular RPM. This allows for lower RPM operation of the flow generator while still achieving the required pressure (which is dependent on tip speed). Having a lower RPM reduces vibration to an acceptable level, or to a level that can be compensated for by the bearing structure and/or stator mount. The lightweight construction of the impeller as mentioned previously enables the larger impeller as it provides lower inertia that achieves the required pressures/ response. That is, lower torque is required to speed up and slow down the impeller to reach the required tip speeds/ pressures. This improves dynamic performance (response). In addition to this, small magnets in the motor (combined with the bearing structure) remove the need for balancing during assembly, improve dynamic performance.

The resilient/flexible bearing structure allows for self-alignment, compliance, damping and preload of the impeller and shaft assembly. This makes assembly easier, and in combination with the lightweight/low inertia impeller reduce or negates the need for balancing modifications during assembly, as mentioned previously. The bearing structure provides for relaxed tolerances during manufacture as it compensates for larger tolerances. The bearing structure also isolates and/or damps vibrations, also allowing high RPM speeds of the impeller where necessary.

The partition 33001 that separates the flow generator into first and second regions separates out the high velocity region to reduce noise. This allows for and maintains a constant high velocity of flow while diffusing the velocity to pressure.

With reference to FIG. 27, the bottom casing cap 25005 includes openings 25019 to allow air to pass through the motor 402. Air flowing through the motor helps to cool the motor and prevent it overheating. In the embodiment shown, there are six openings 25019. The openings 25019 are centrally located and are sector shaped. In alternative embodiments, the openings 25019 may be located in different parts of the cover or have different shapes, such as circular. There may be more or less openings 25019, for example, four, eight, or nine openings 25019. The bottom casing cap 25005 also includes six fastening mechanisms 25021 that secure the bottom casing cap 25005 to the partition 33001. The fastening mechanisms are screws 2501*a* that extend through clearance apertures 25021*b* provided in in the bottom casing cap 25005. The screws 2501*a* are in threaded engagement with apertures provided in bosses 25021*c* in the partition.

Figure 30:
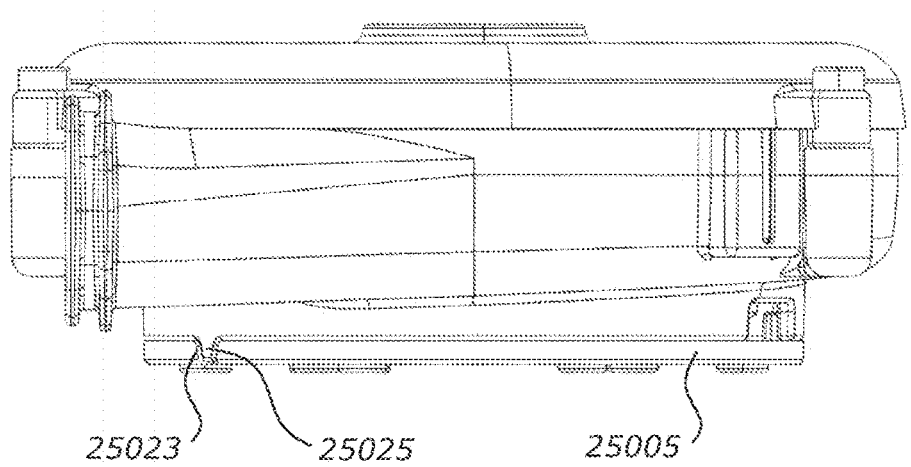
FIG. 30 is a side view of the flow generator of FIG. 25.
Figure 31:
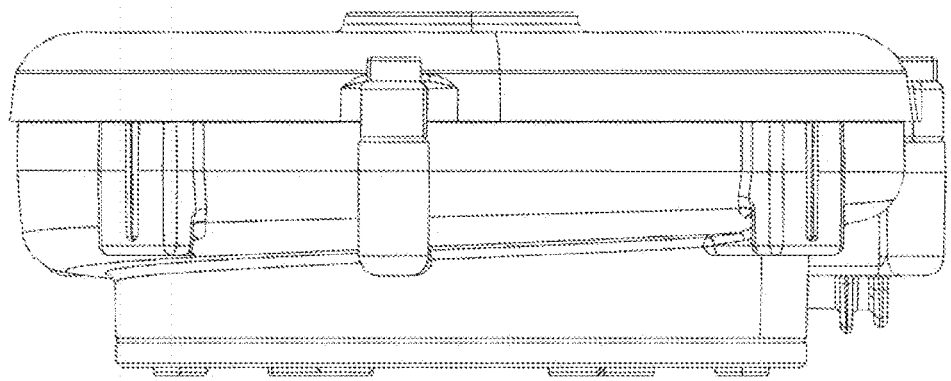
FIG. 31 is a side view of the flow generator of FIG. 25.

FIG. 30 shows the bottom casing cap 25005 has an alignment feature 25023 that aligns with a protruding section 25025 of the bottom casing 25003. In an alternative embodiment, the protruding section may be on the bottom casing cap 25005 and the alignment feature may be on the bottom casing 25003. The interaction between the alignment feature 25023 and the protruding section 25025 assist during assembly to ensure that the bottom casing cap 25005 and the bottom casing 25003 assemble together correctly.

Figure 32:
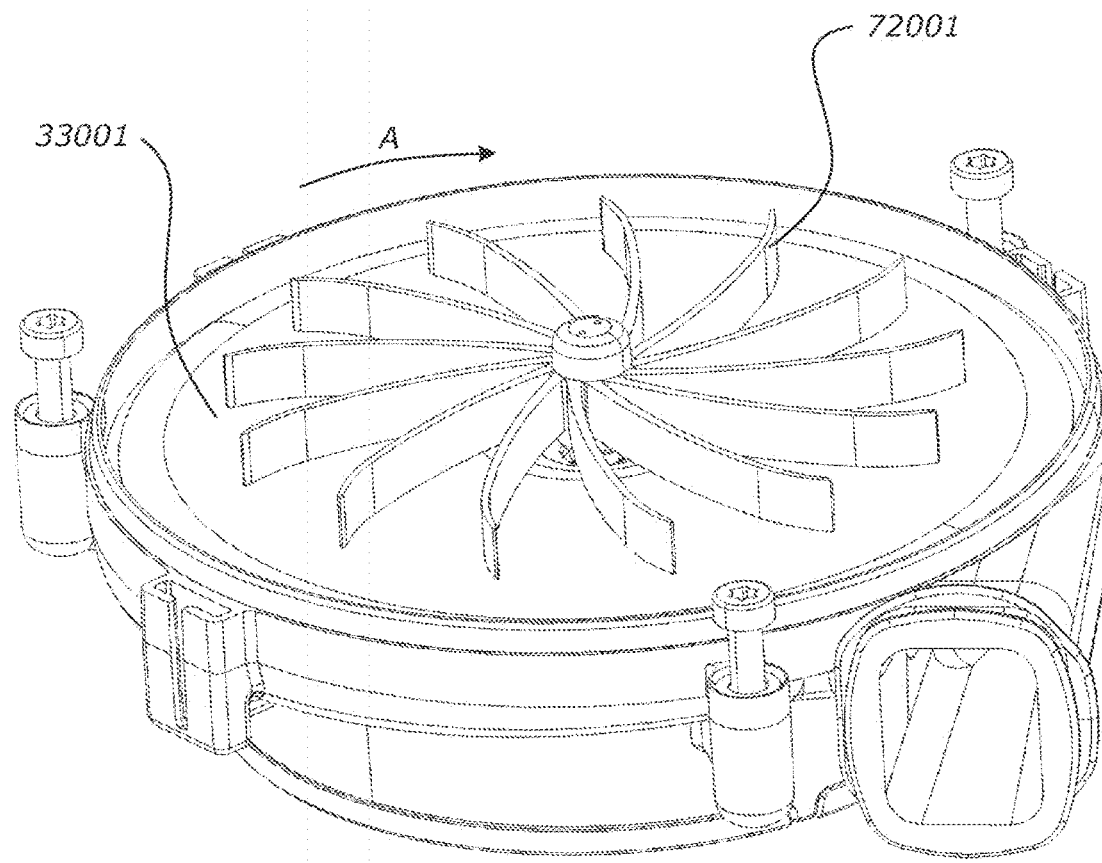
FIG. 32 shows the flow generator of FIG. 25 with the top housing hidden.
Figure 33:
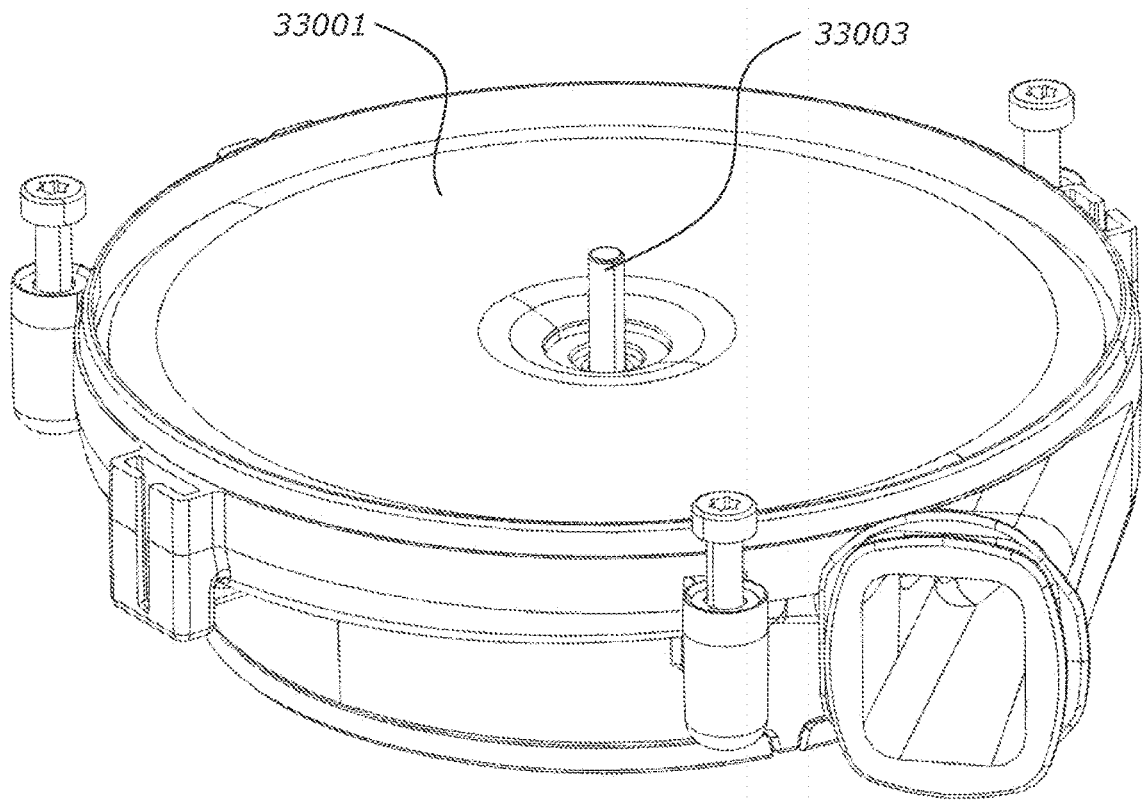
FIG. 33 shows the flow generator of FIG. 25 with the top housing and the impeller hidden.
Figure 34:
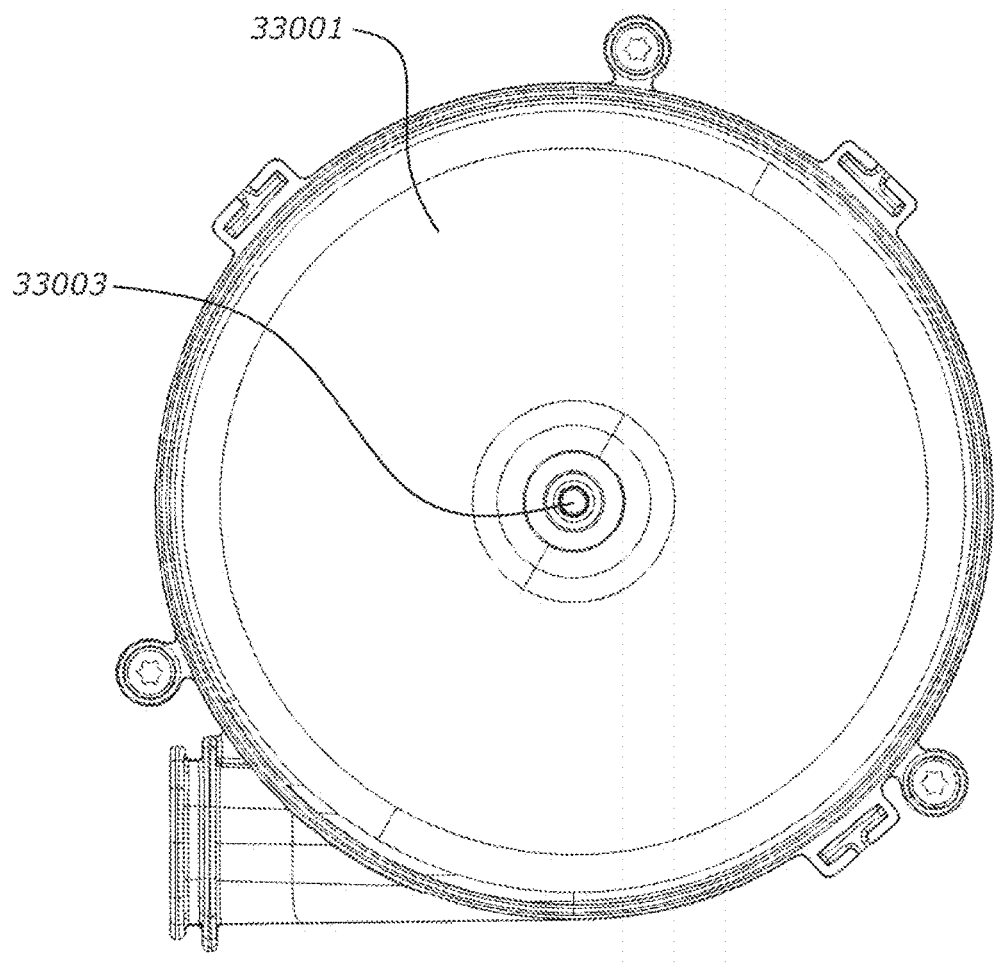
FIG. 34 is a top view of the flow generator of FIG. 25 with the top housing and the impeller hidden.

FIG. 32 shows the flow generator 11 with the top casing 25001 hidden. The impeller 72001 rotates within the upper region 62001 to direct air from the inlet 25007 to the flow generator casing exit 25009. In the figure above, the impeller 72001 rotates clockwise as shown by the arrow labelled A.

Figure 35:
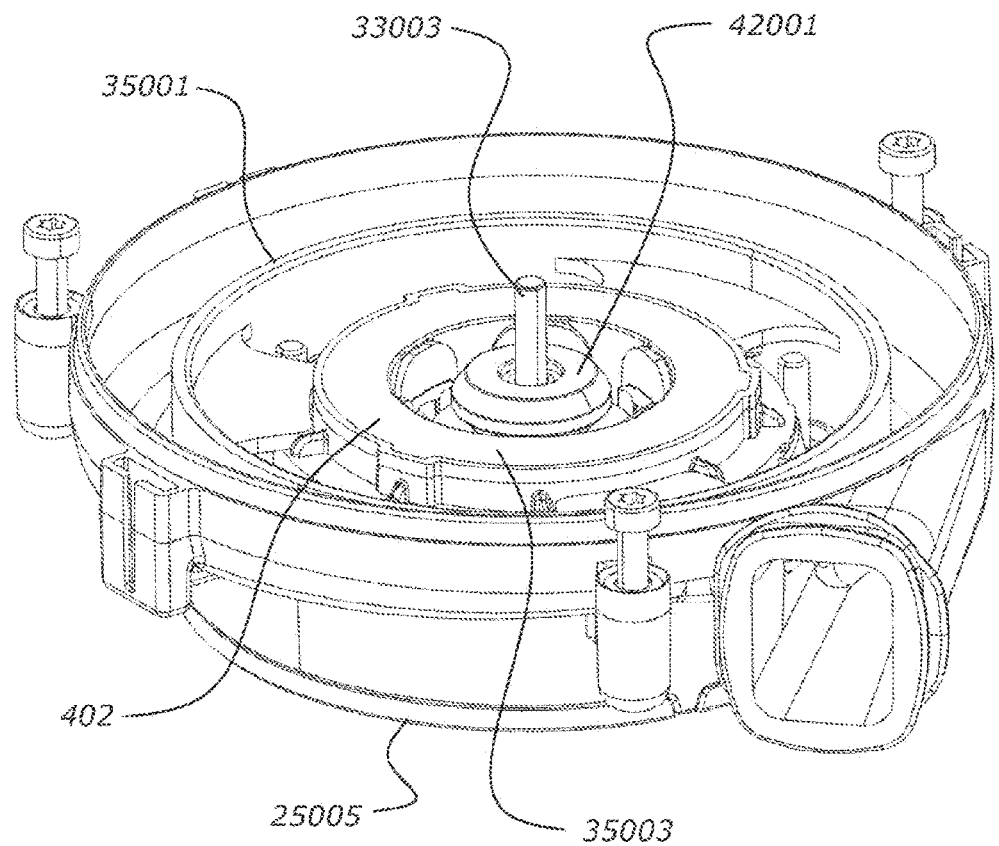
FIG. 35 is a perspective view of the flow generator of FIG. 25 with the top housing, impeller and the partition hidden.

FIG. 35 is a perspective view of the flow generator of FIG. 25 with the top housing, impeller and the partition hidden, showing one embodiment of a bearing mount 42001, the shaft 33003, and the sealing inner wall 35001. FIG. 36 is a view similar to FIG. 35 with the bottom casing 25003 also hidden. The bottom casing cap/partition fastening mechanism are screws that enter from the bottom of the bottom casing cap 25005. The bottom casing cap 25005 includes a plurality of arcuate projections 36001. The arcuate projections 36001 engage or abut the lower casing to provide alignment between the bottom housing cap 25005 and the bottom housing 25003.

Figure 64:
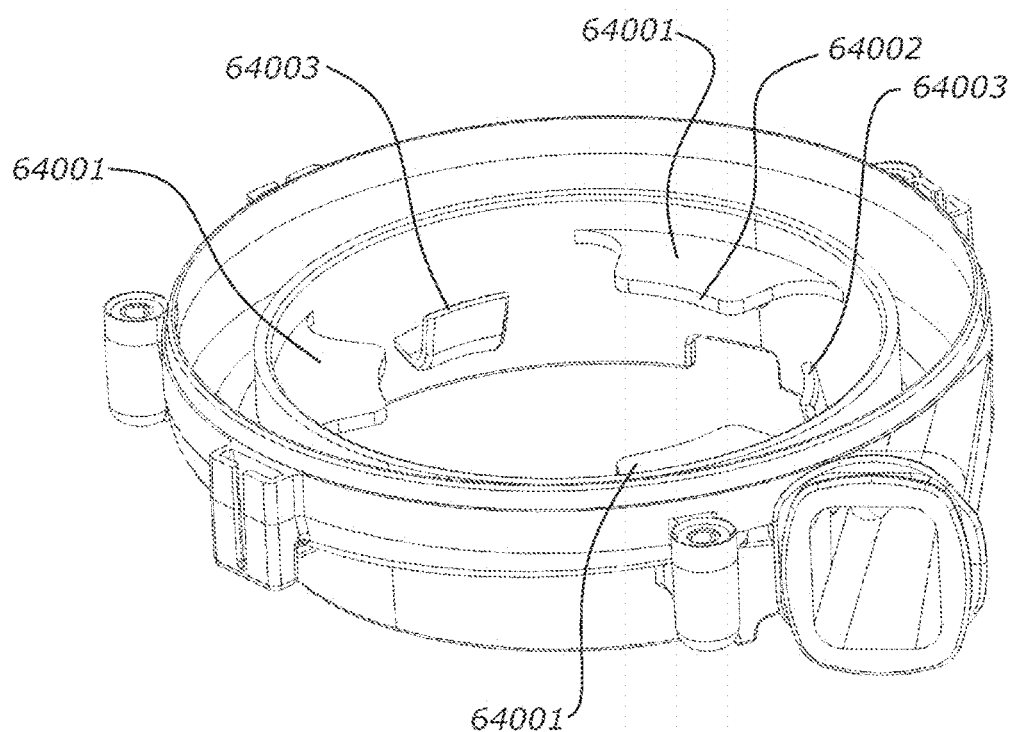
FIG. 64 is a perspective view of the bottom housing.
Figure 65:
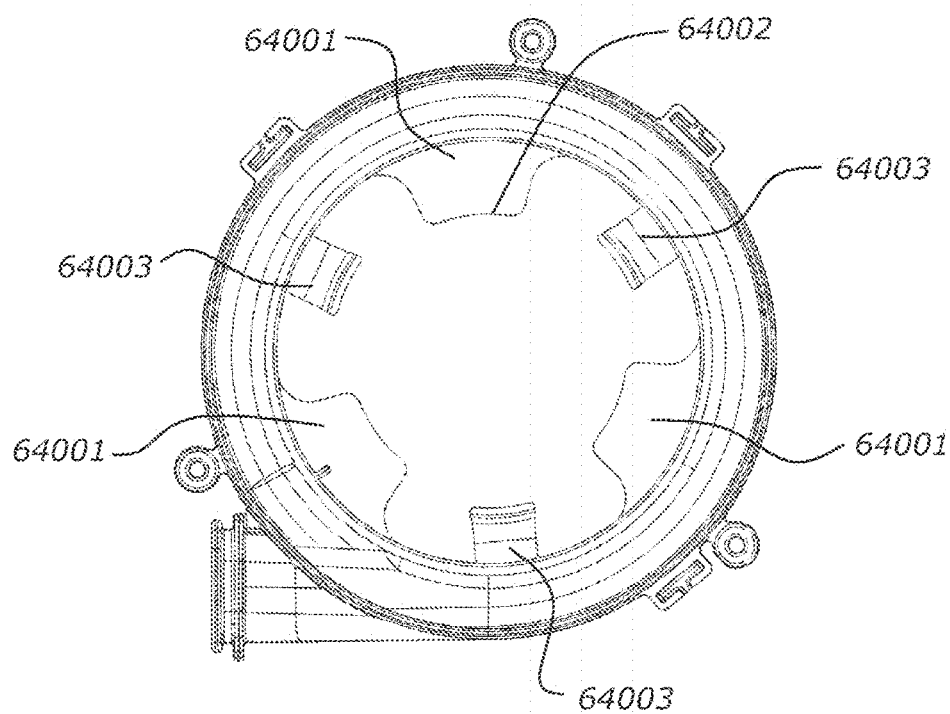
FIG. 65 is a top view of the bottom housing.
Figure 66:
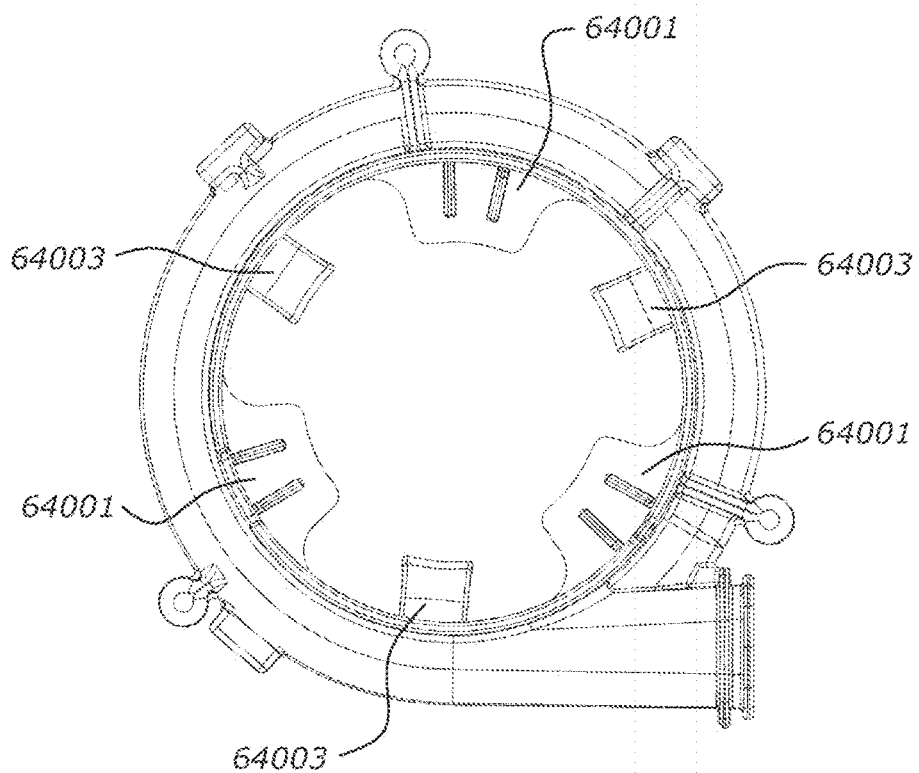
FIG. 66 is a bottom view of the bottom casing.
Figure 67:
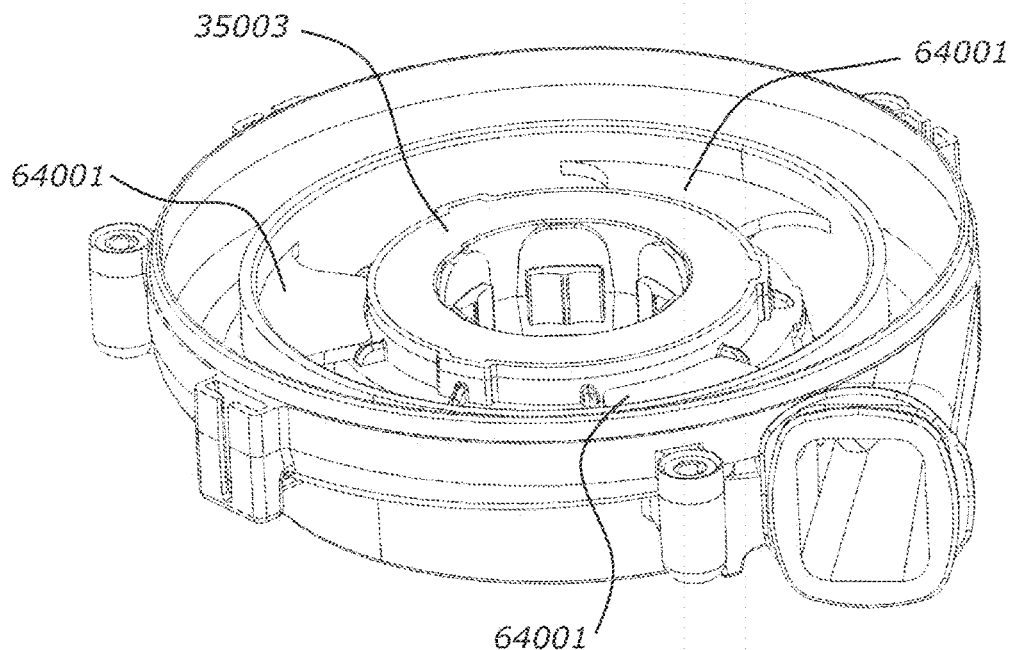
FIG. 67 shows a perspective view of the stator connected to the bottom casing.
Figure 68:
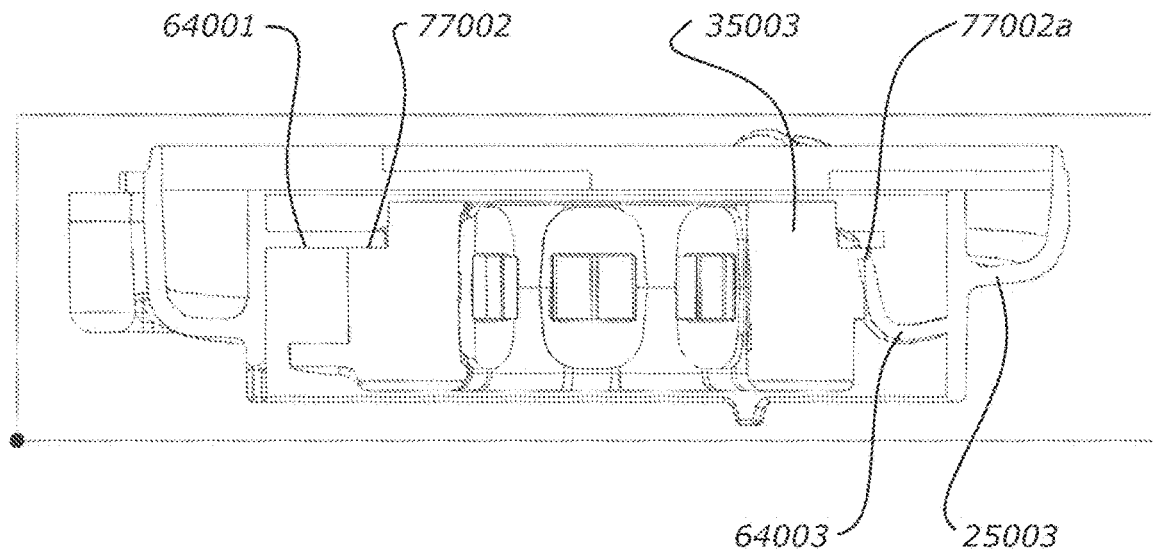
FIG. 68 is a cross-sectional view showing the stator connected to bottom casing.

FIG. 64 shows a stator support system. FIG. 64 shows the bottom casing 25003 including a bottom casing ledge 64001 and a flexible or resilient member 64003. In the preferred embodiment, there is a plurality of bottom casing ledges 64001 and flexible or resilient members 64003.

The stator support system also includes a vibration isolating member located between the stator and the bottom casing cap 25005 arranged to bias the stator 35003 in a direction towards the first stator ledge. The vibration isolating member is described in more detail below.

The bottom casing ledges 64001 and resilient members 64003 cooperate with the stator 35003 to support the stator in the bottom casing 25003. Each bottom casing ledge 64001 has a curved inner surface 64002 that substantially corresponds to the curve of the stator 35003. In the embodiment shown, there are three bottom casing ledges 64001, however there may be more or fewer bottom casing ledges 64001. The bottom casing ledges 64001 are evenly spaced around the bottom casing 25003. The bottom casing ledges 64001 are all at the same height. In the embodiment shown, there are three resilient members 64003, however there may be more or fewer resilient members 64003. The resilient members 64003 are evenly spaced around the bottom casing 25003. The resilient members 64003 are all at the same height.

The bottom casing ledges 64001 and resilient members 64003 are integrally formed with the bottom casing 25003.

With reference to FIGS. 67 to 70, the stator 35003 includes a first stator ledge and a second stator ledge. In the illustrated embodiment, the first stator ledge is a peripheral ledge 77002 that cooperates with the ledges 64001, and the second stator ledge is a recess 77002*a* or the underside of the ledge under the stator peripheral ledge 77002 that cooperates with the resilient member 64003 of the casing to support the stator 35003.

The ledges 64001 support the stator and secure the stator from motion in a direction parallel to the axis of the shaft, by acting as a physical impediment to said motion, since the end of the ledge 77002 and the stator peripheral ledge overlap. The peripheral ledge of the stator also includes a lateral retaining feature 77003 preventing or limiting the stator 35003 from being able to rotate with respect to the bottom casing 25003.

Figure 69:
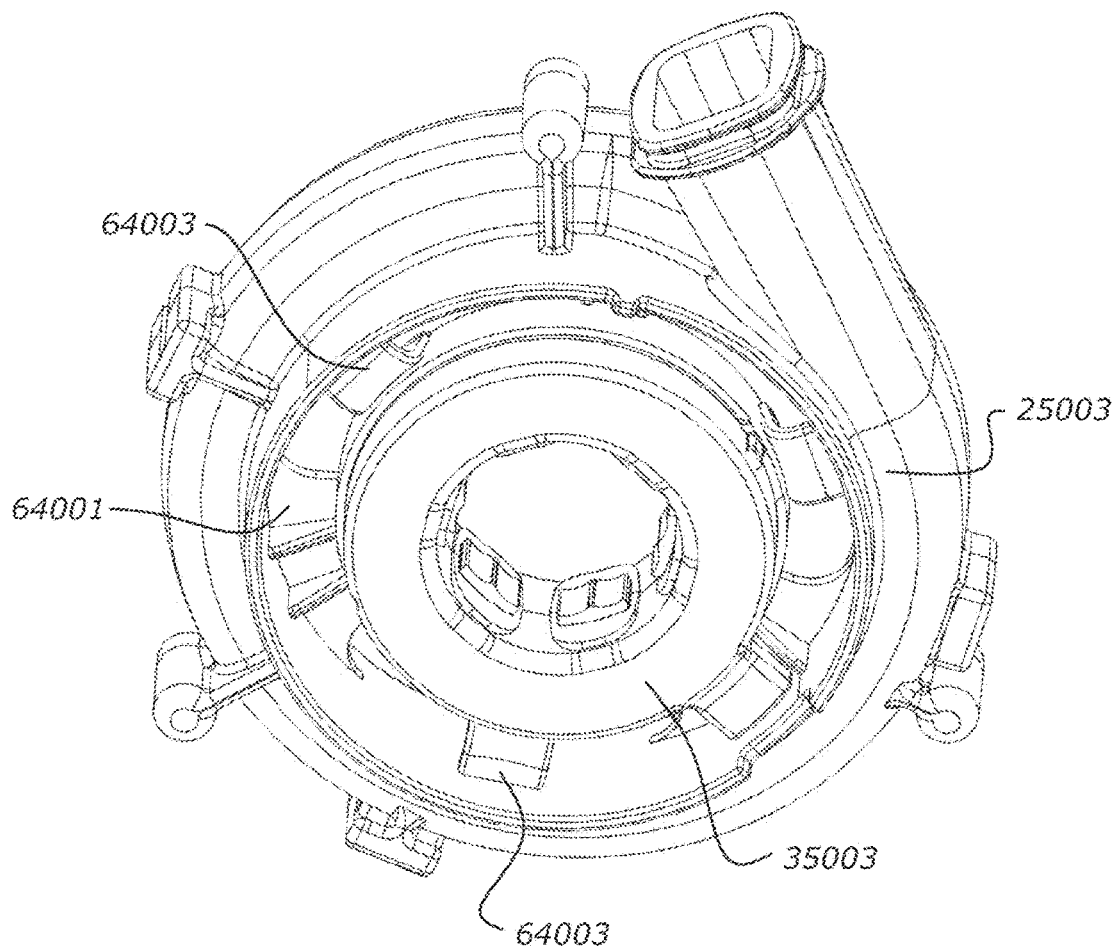
FIG. 69 is a perspective view of the stator connected to the bottom casing.
Figure 70:
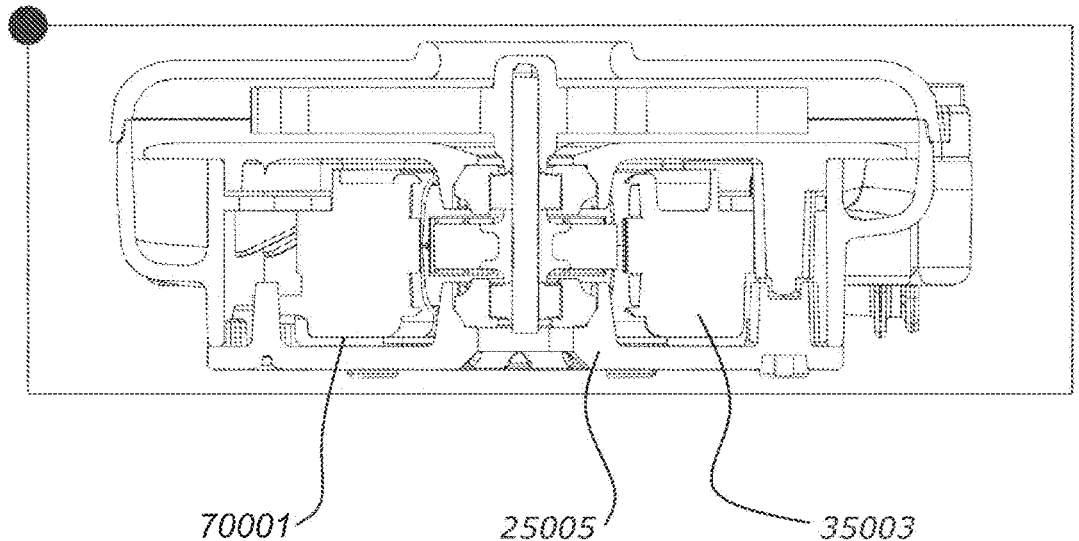
FIG. 70 is a cross-sectional view showing the bottom casing and stator.
Figure 71:
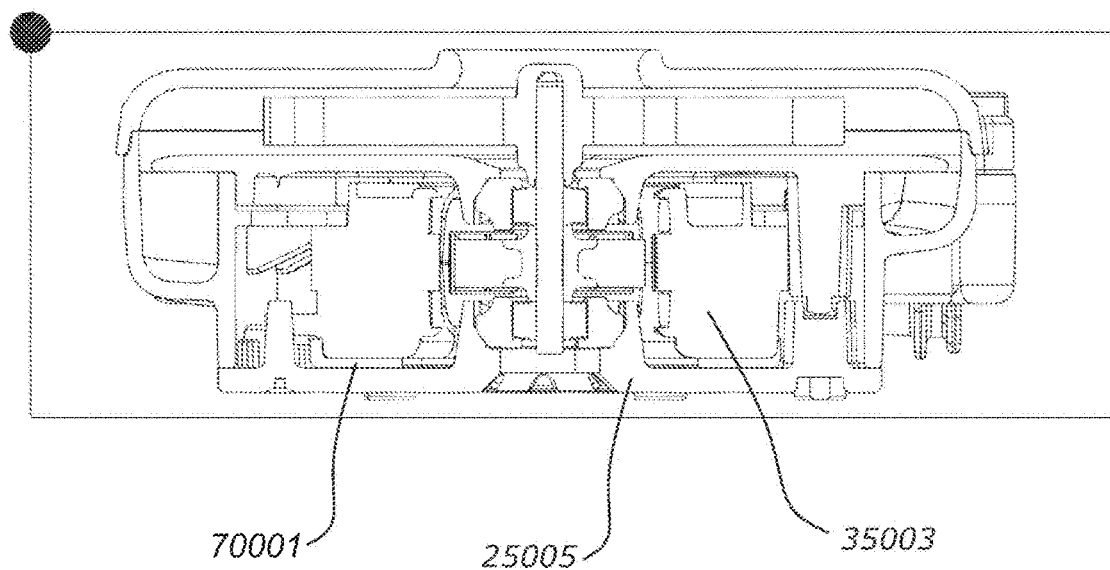
FIG. 71 is a cross-sectional view of the flow generator showing a stator preload cap.
Figure 72:
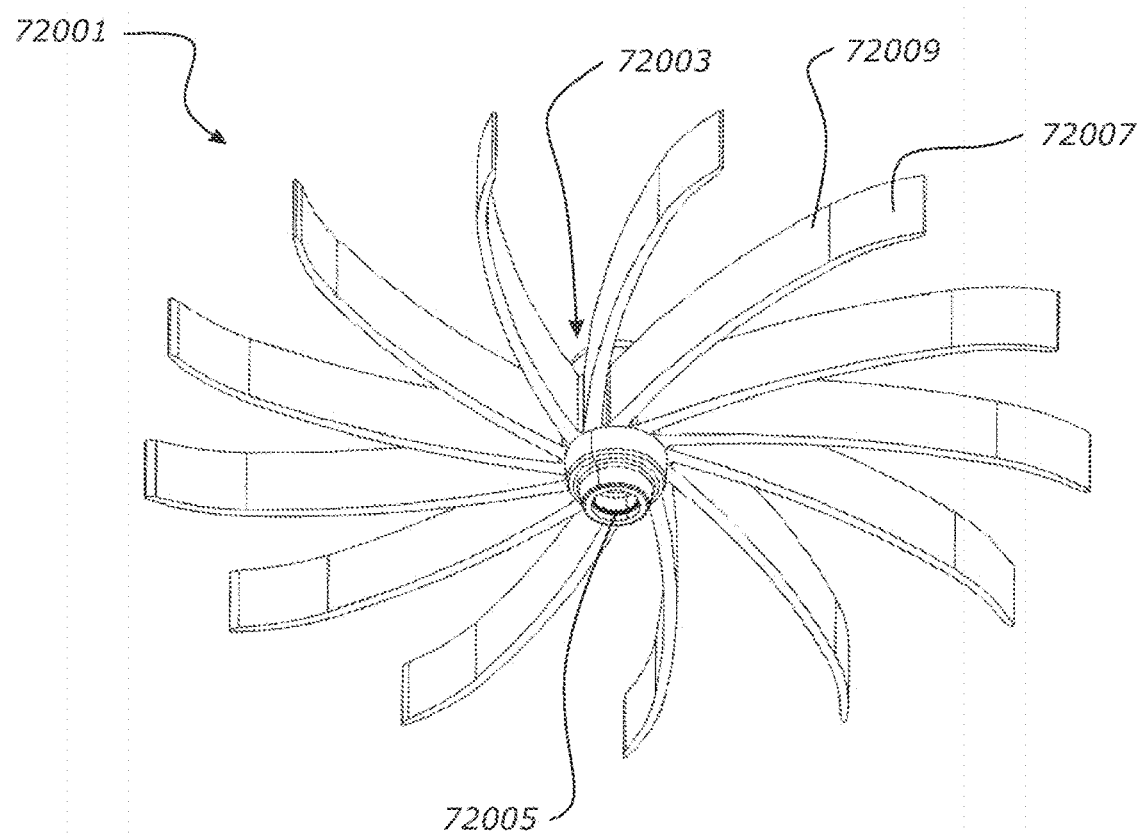
FIG. 72 is a perspective view from below of the impeller.
Figure 73:
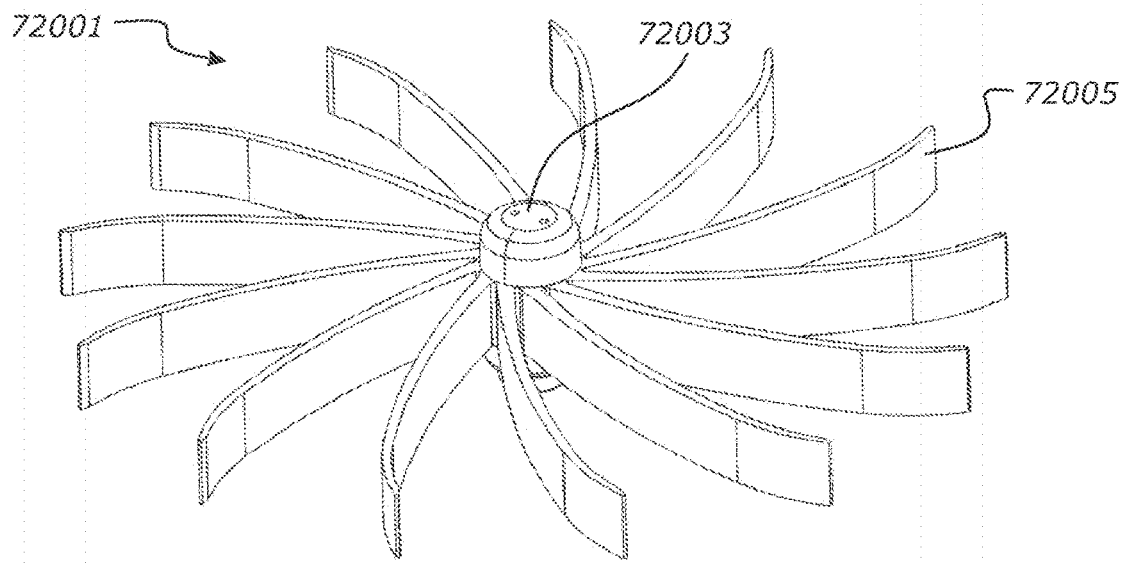
FIG. 73 is a perspective view from above of the impeller.
Figure 74:
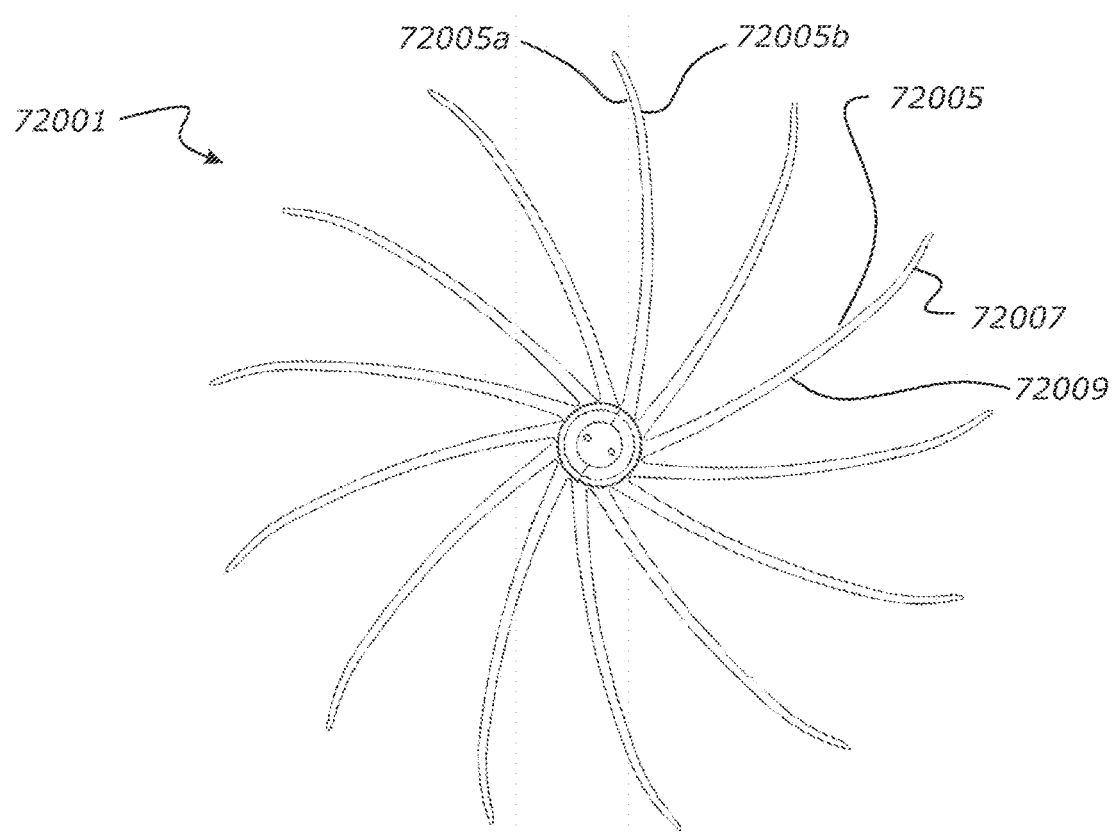
FIG. 74 is a top view of the impeller of FIG. 72.
Figure 75:
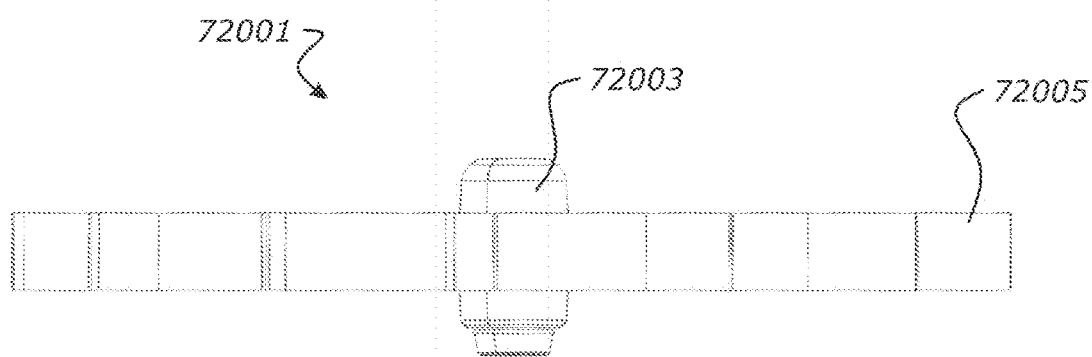
FIG. 75 is a side view of the impeller of FIG. 72.

FIG. 69 shows a bottom perspective view of the stator 35003 connected to the bottom casing 25003, with the bottom casing cap 25005 hidden, for clarity. FIG. 70 shows a section plane of the bottom casing 25003 and stator assembly showing how each ledge and each resilient member interacts with the stator 35003.

The stator 35003 is retained in place when forced vertically through the bottom of the bottom casing (when the apparatus is in the position shown in FIG. 69) because the ledges 64001 react against the stator peripheral ledge. Each resilient member 64003 is initially required to flex or deform somewhat, and forms a clip fit with a recess 77002*a* or the underside of the ledge under the stator peripheral ledge 77002. When clipped in, the resilient members 64003 prevent the stator 35003 from being removed by being pushed downwards (when the apparatus is in the position shown in FIG. 69). It may be preferable for the motor to be removable. Each resilient member 64003 can be configured to flex beyond a periphery of the stator to allow removal of the stator 35003 from the casing. Alternatively, the resilient members may be configured such that the stator is not removable. For example the shape or material of the resilient members may be chosen or designs to prevent removal of the stator 35003.

The flow generator preferably includes a biasing component or components to bias components together and remove any play or space between those components. When the flow generator is assembled, there is vertical clearance to allow the stator to be inserted and the casings to be assembled into a unified casing. The clearance creates play between the components and allows for the components to move or vibrate relative to each other. Additionally, the resilient members 64003, by nature of being resilient, may flex somewhat when the stator 35003 is in place and the motor is operating due to vibration. This flexing may result in the stator 35003 being able to vibrate between resilient members 64003 and ledges 64001 after insertion. To remove the play and minimise the possible vibration of the stator, the biasing component is provided. The biasing component biases or urges the components together to remove the play. In particular, the biasing component biases the components together in a direction that is parallel to the direction of the shaft.

The vibration isolator member FIG. 70 shows one example of a biasing component in the form of a stator preload cap. The stator preload cap 70001 is located between the stator bottom of the stator and the inner surface of the bottom casing cap 25008. The stator preload cap 70001 supports the stator and acts to damp any vibration of the stator 35003. The illustrated embodiment of the stator preload cap is compressible. The stator preload cap 70001 is or comprises an elastomeric material. In particular, the elastomeric material is silicone.

The stator preload cap 70001 can be an elastomeric material (e.g. silicone). The stator preload cap 70001 can span an entire perimeter of the adjacent surface of the stator, or can be broken into segments only spanning partial perimeters of the adjacent surface of the stator 35003. The illustrated stator preload cap 70001 is annular with a central opening. Alternately, the stator preload cap can be cylindrical or another shape. The stator preload cap 70001 can include additional stator preload cap openings configured to permit airflow through the stator preload cap. These additional openings can correspond with the openings in the bottom casing cap. This allows air to flow through the motor assembly more easily or effectively, assisting in dissipating heat from the motor assembly.

Figure 83:
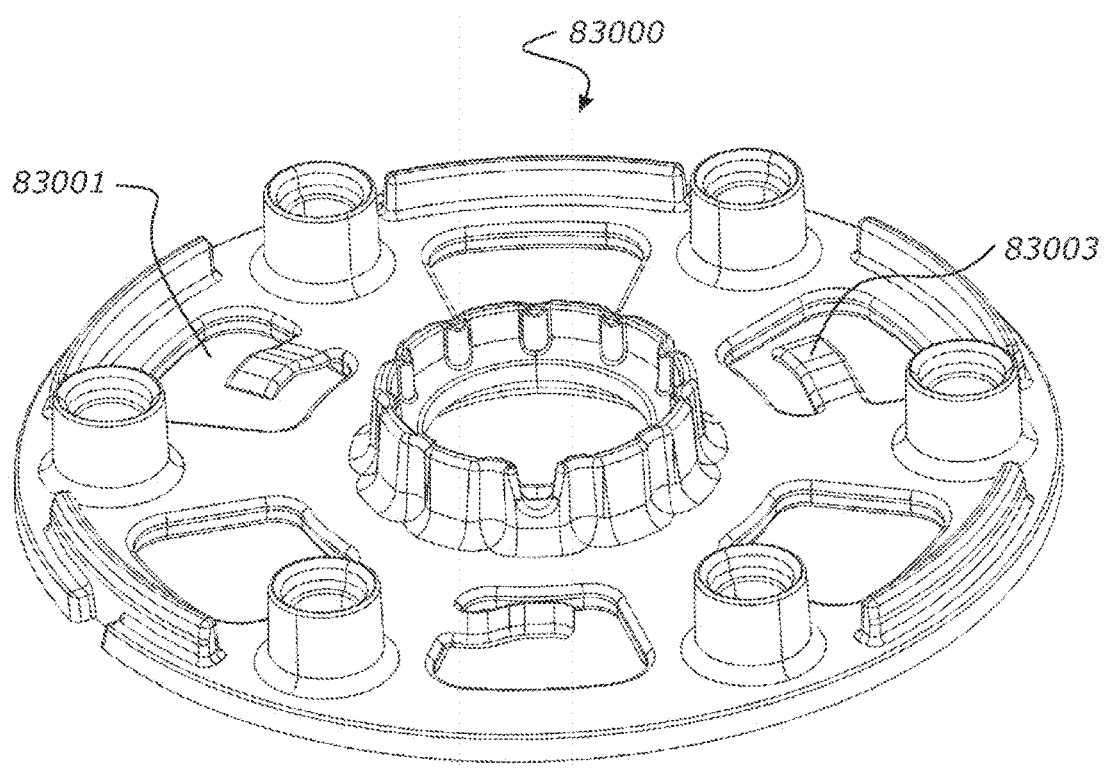
FIG. 83 shows a biasing component in the form of a modified bottom casing cap.

FIG. 83 shows a biasing component in the form of a modified bottom casing cap 83000. The bottom casing cap 83000 has the same features and functions as the bottom casing cap described above, except that it includes resilient fingers 83003. The resilient fingers are integrally formed with the bottom casing cap 83000. The resilient fingers 83003 are shaped and formed form a resilient material to provide a biasing force towards the stator 35003 to damp any vibration of the stator 35003.

The preferred form of the impeller is shown in FIGS. 72 to 76. The impeller 72001 has a plurality of blades 72005 extending outward from a central hub 72003. The impeller is a centrifugal impeller. The hub 72003 defines the axis about which the impeller rotates. Preferably the hub 72003 has an aperture or recess on the underside to allow engagement with a motor shaft 33003 which facilitates impeller rotation. However, other engagement mechanisms, such as over moulding of the shaft 33003 with a hub, could be used. Each impeller blade 72005 includes a concave surface 72005a and a convex surface 72005b. Each of the concave and convex surfaces are oriented parallel to the axial direction of the impeller, and therefore perpendicular to the rotational direction of the impeller. When the impeller is rotated, air enters the impeller blades in the region proximate the hub 72003, travels radially outward and exits the blades proximate the blade tips 72007. The impeller is preferably made in one piece ("one piece construction"), as opposed to moulded in multiple parts and joined. This is possible when there is no shroud—or at most one shroud. This reduces misalignment of components that might lead to imbalance or other disadvantages. In the preferred embodiment there is no shroud.

The impeller is constructed to be lightweight. Preferably, this is by making the impeller shroudless, or at least partially shroudless, thereby removing weight. To achieve a lightweight impeller, as shown in FIGS. 72 to 76, each of the blades 72005 of the preferred impeller 72001 are open between the blades (that is, the upper and lower "faces" or "planes" of the impeller are open to the internal surfaces of the casing of the flow generator 11) thereby defining a shroudless centrifugal impeller. By omitting a shroud on both the upper and/or lower faces of the impeller blades, the weight of the impeller 72001 can be substantially reduced. The weight of the impeller can also be reduced in other ways, in addition to or alternatively to omitting the shroud. For example, a lightweight material can be used. Also, thin blades with minimal material and large gaps between blades could be implemented to reduce weight. Alternatively, a shroud with some of the material removed could be used. A scalloped shaped may be provided whereby some of the material between blades 72005 is removed. Any suitable amount of material could be removed. A shroud channels air from the impellers. Where significant material is removed, the resulting structure may in fact no longer carry out this function of a shroud but rather just provide support for impeller blades 72005. In this case, the impeller 72001 may still be considered shroudless, despite having some structure between impeller blades 72005. In yet a further alternative embodiment, the structure between the impeller blades may be a webbing that is disposed centrally between impellers. Such as structure does not function as a shroud. The reduced material structure or webbing can be of any shape (not just scalloped) or extent. A lightweight impeller 72001 provides benefits such as manufacturing cost, low rotational inertia and is balanced or requires little effort to rotationally balance once manufactured. An impeller with low rotational inertia can be quickly accelerated and decelerated. A lightweight, shroudless impeller is therefore suited for quickly responding to fluctuating pressure requirements, such as the normal inhalation and exhalation cycle of a patient connected to the breathing assistance device in which the impeller operates.

For example, a conventional shrouded impeller commonly used on a breathing assistance device, weighing approximately 17 grams and having inertia of 6 kg·mm2, can respond to pressure fluctuations of 10 cmH2O in approximately 2 seconds. By contrast, the preferred impeller, weighing approximately 1.7 grams and inertia of 0.5 kg·mm2, responds pressure fluctuations of 10 cmH2O in approximately 100 ms. As the impeller has a lower mass and rotational inertia compared to conventional impellers, the impeller exhibits much less pressure fluctuation. The reduced pressure fluctuation is less disruptive to a patient's breathing process, and therefore advantageously increases patient comfort.

As mentioned, the lightweight of the impeller can be achieved by omitting a shroud. However, it is not necessary to omit the entire shroud—rather just sufficient shroud to bring the weight of the impeller to a suitable level—. Therefore, lightweight can be achieved by having as much open space (area or volume) between the blades as possible. The open space can be defined in terms of the blade volume to blade sweep volume ratio/percentage. That is, the blades sweep a volume X when rotating and the blades themselves have a combined volume Y (which is the volume of each blade combined). Alternatively, from a plan perspective, the open space can be defined in terms of the blade area to the blade sweep area. The ratios should be kept as low as possible. In one embodiment, for example the swept volume of the impeller is approximately 19,000 mm3, where the blades constitute a volume of approximately 1,200 mm3. The ratio of swept volume to blade volume is therefore approximately 16:1, thereby defining an impeller that is lightweight compared to the smaller, more densely designed and heavier impellers used earlier.

The lightweight impeller can have a weight for example of less than 2 grams and preferably between 0.8 and 1.8 grams, or more preferably, between 1.2 and 1.7 grams, or even more preferably 1.7 grams. These are just examples or a preferred embodiment and the impeller need not be this weight, but some other weight that renders it lightweight.

Alternatively, a lightweight impeller can be designed to remove as much of the shroud as necessary to bring the moment of inertia to radius ratio down to preferably less than 15 gram*mm, and more preferably between 8-12 gram*mm and in one possible embodiment approximately 11 gram*mm. For example, in one possible embodiment, such an impeller can have a radius of 35 mm, a circumference of 219 mm, and at 15,000 rpm a moment of inertia of 344.22, a tip speed of 54.98 m/s, a pressure of 1,800 Pa and a tip speed to inertia to radius ratio of 3.5 or more and for example 5.59. More generally, a lightweight impeller could have dimensions/parameters within the following ranges (note these ranges are indicative—not limiting):

Radius: 15 mm-60 mm
Weight: less than 2 grams

A pressure ratio to inertia to radius ratio of greater than 50:1 Pascals per gram*mm and preferably 80:1 Pa per gram*mm or more at 1,000 Pa.

Lightweight impellers enable larger radius impellers to be used. Yet larger radius impellers can be used than those mentioned above. Larger radius impellers provide greater tip speed and pressure. The construction of the impeller allows for greater radius impellers because the lightweight nature of the impeller is such that even with larger impellers, the inertia is still low enough to provide the required response and pressures.

The lightweight nature of the impeller can be achieved through removing mass through any suitable means, such as removing the shroud and/or material from the impeller and/or using lighter materials. One possible manner in which to reduce impeller mass is to reduce the number of blades.

FIGS. 72 to 76 show an impeller 72001 suitable for use with the blower. The impeller 72001 has a hub 72003 with a centrally located aperture 72005 for receiving the shaft. The impeller 72001 has a plurality of blades 72005 extending outwardly from the hub 72003. The impeller 72001 is designed to rotate clockwise (in FIG. 74). The preferred embodiment impeller 72001 has backward swept blades 72005. The preferred embodiment impeller 72001 has a prime number of blades 72005 (eg: 11, 13, 17) to reduce blade pass and other noises produced by the rotation of the impeller 72001. In the embodiment shown, the impeller 72001 has 13 blades 72005.

Figure 76:
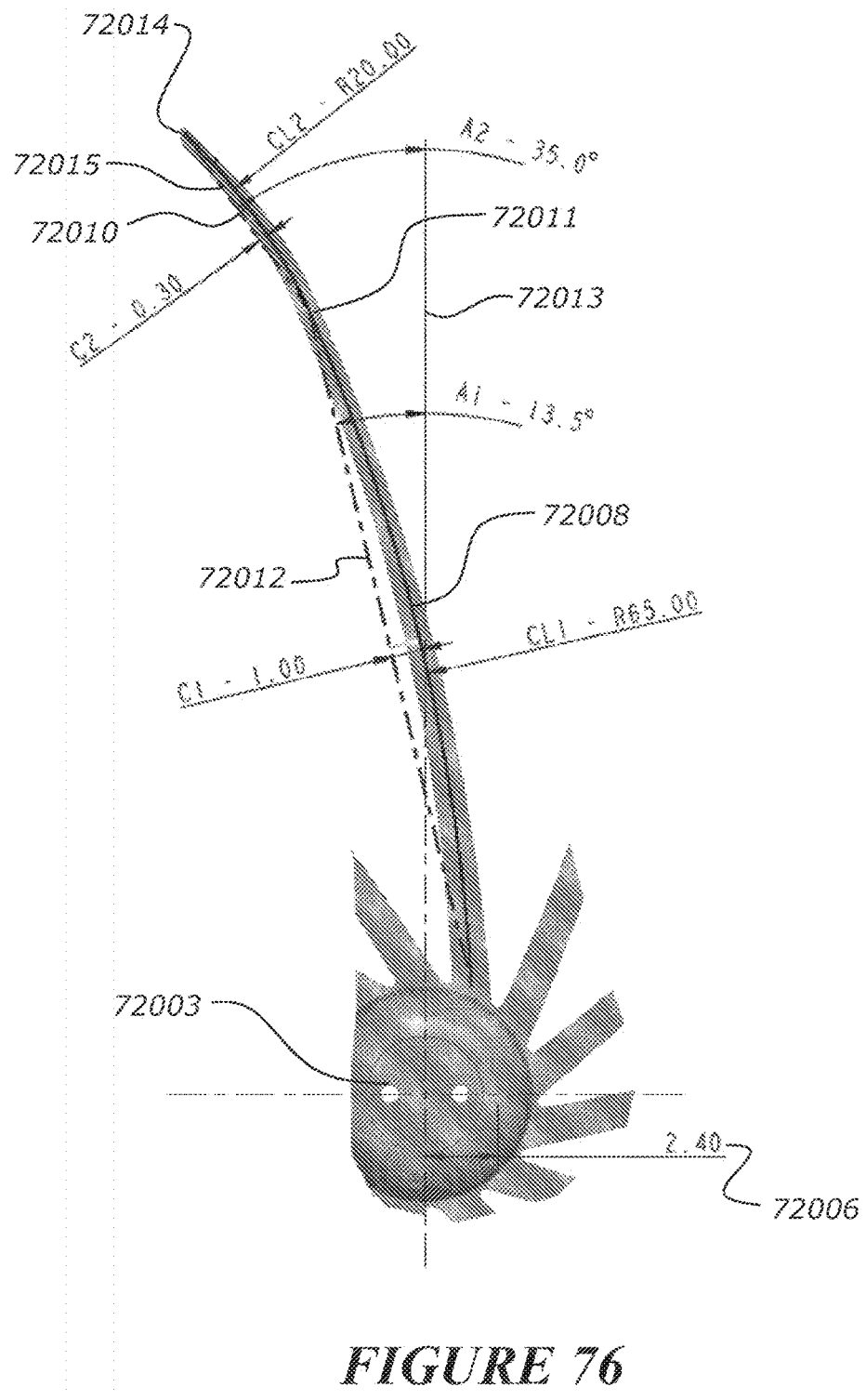
FIG. 76 shows an impeller blade including the curves of the impeller.
Figure 77:
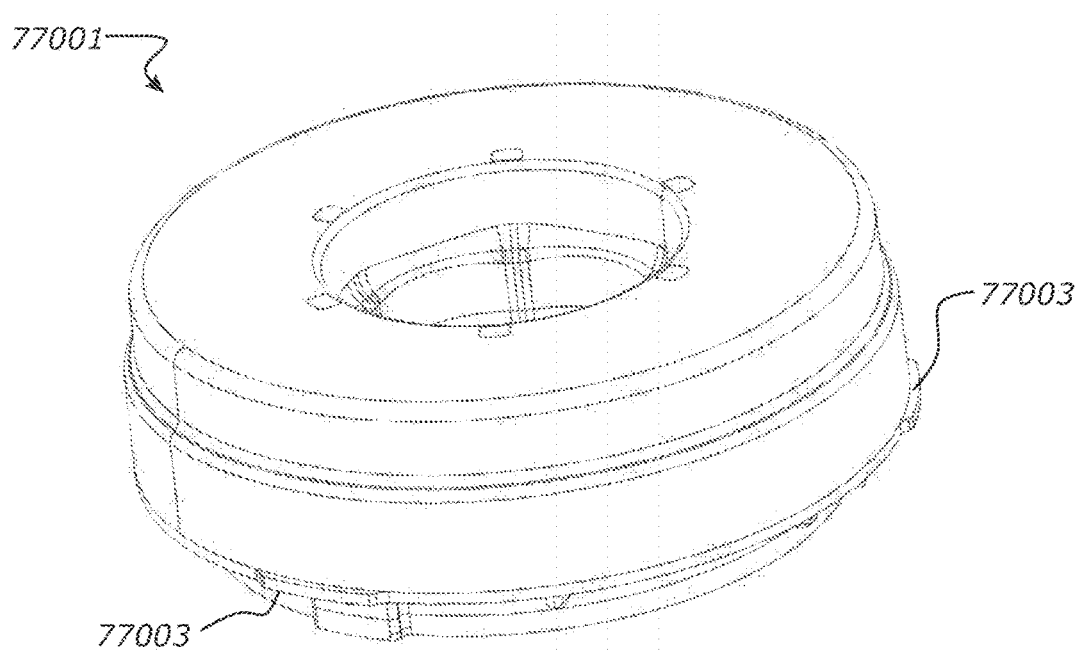
FIG. 77 is a perspective view of a shield for the stator.
Figure 78:
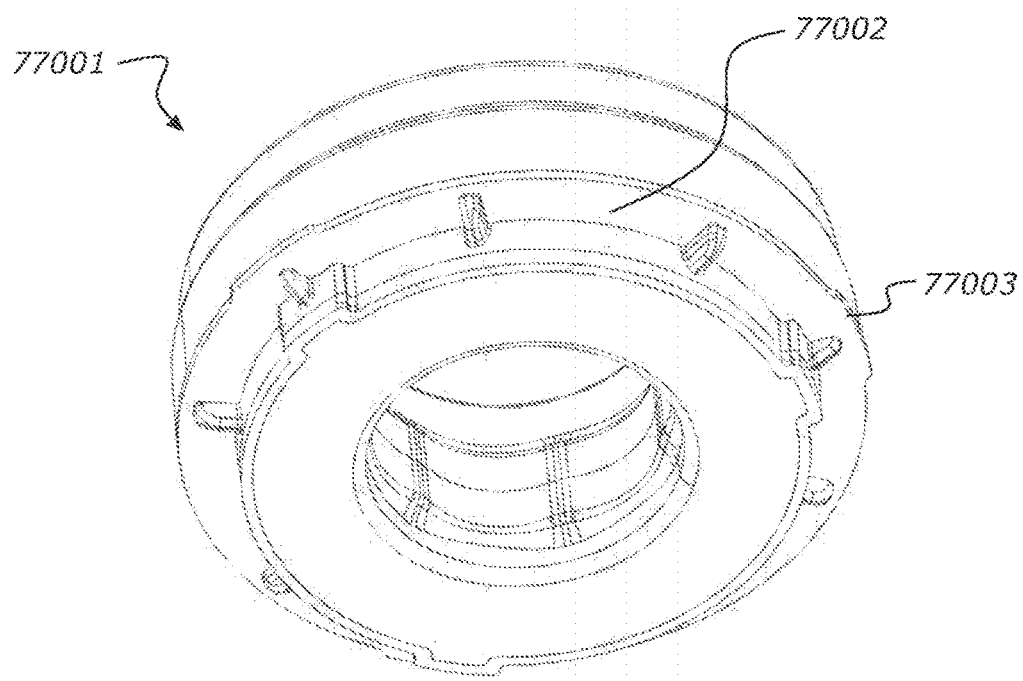
FIG. 78 is a perspective view from below of the shield of FIG. 77.
Figure 79:
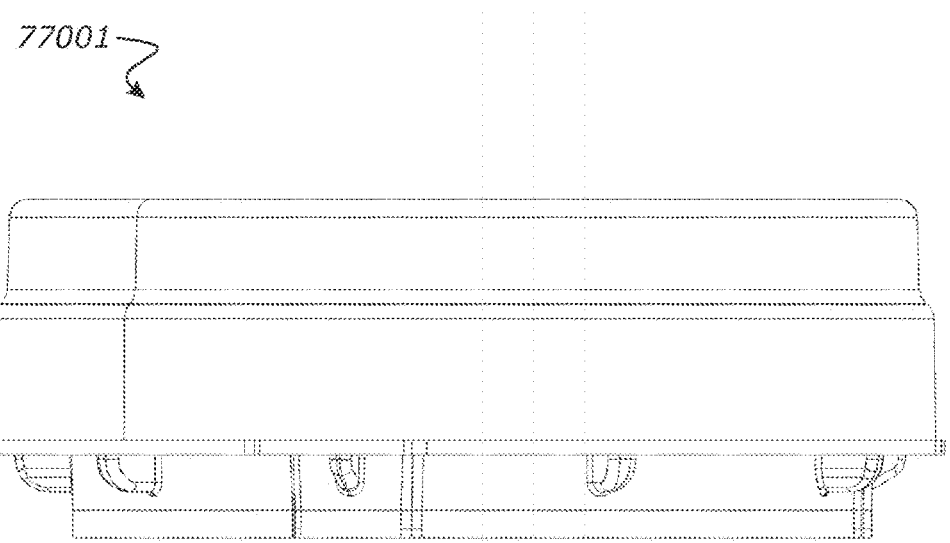
FIG. 79 is a side view of the shield of FIG. 77.
Figure 80:
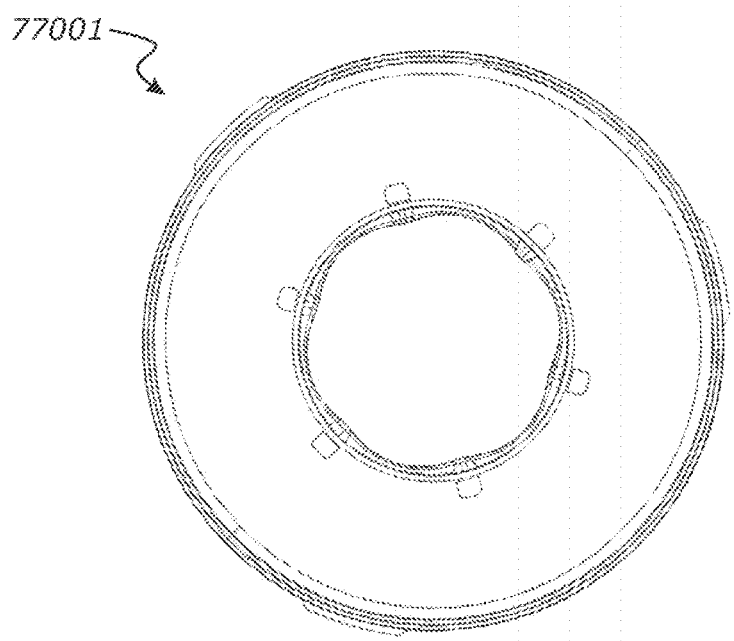
FIG. 80 is a top view of the shield of FIG. 77.
Figure 81:
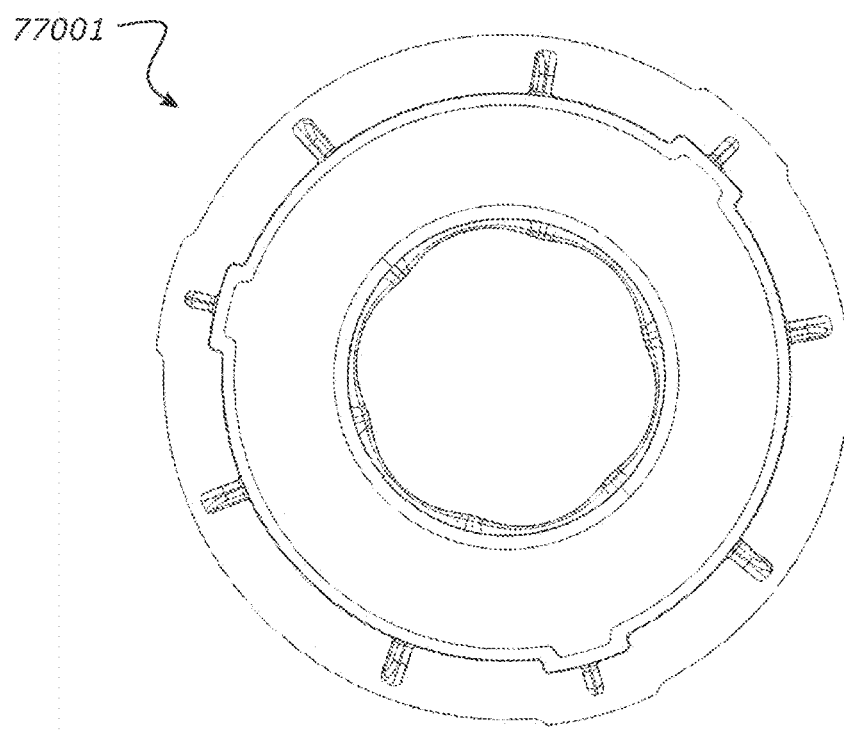
FIG. 81 is a bottom view of the shield of FIG. 77.

FIG. 76 shows a top view of the impeller 72001, identifying the curves and dimensions that define the structure of the impeller blades 72005.

With reference to FIG. 76, the shape of each impeller blade 72005 is defined by an offset 72006 from the centre of the hub 72003 and two curves 72008 and 72010. The two curves provide an impeller blade 72005 that is backwards swept. The first curve 72008 defines a primary portion of the blade 72009 and the second curve 72010 defines a secondary portion 72007 of the blade which forms a blade tip.

The first curve 72008 extends outwardly from the hub 72003 along a curve with a radius of about 65 mm. The first curve 72008 extends, with its outward edge extending from the offset 72006, to a point 72011 where a chord 72012 formed by the curve is angled at 13.5° from the shown vertical axis 72013.

The second curve 72010 extends outwardly from the end of the first curve 72008 with a radius of about 20 mm. The second curve 72010 extends from the end of the first curve 72008 to a point 72014 where a chord 72015 formed by the curve 72010 is angled at 35° from the shown vertical axis 72013.

Although the present disclosure has been described in terms of certain embodiments, other embodiments apparent to those of ordinary skill in the art also are within the scope of this disclosure. Thus, various changes and modifications may be made without departing from the spirit and scope of the disclosure. For instance, various components may be repositioned as desired. Features from any of the described embodiments may be combined with each other and/or an apparatus may comprise one, more, or all of the features of the above described embodiments. Moreover, not all of the features, aspects and advantages are necessarily required to practice the present disclosure. Accordingly, the scope of the present disclosure is intended to be defined only by the claims that follow.

The various configurations described are exemplary configurations only. For example, while the motor and/or sensor sub-assembly recess is described as being in the underside of the main housing, it could alternatively be in a rear, side, front, or top of the housing. With such a variant, the air and/or oxygen inlets may also be positioned differently as required.

The features are described with reference to a flow therapy apparatus that is capable of delivering heated and humidified gases to a patient or user. The apparatus may be suitable for treating chronic obstructive pulmonary disease (COPD). The apparatus may be configured to deliver gases to a patient interface at a high flow rate (high flow therapy).

Alternatively, one, some, or all of the features may be provided in an apparatus for a different purpose. The apparatus may be a high flow therapy apparatus, or may be a low flow therapy apparatus. The features may also be provided in an apparatus for providing continuous positive airway pressure (CPAP), which may deliver gases (humidified or otherwise) at positive pressure.

One or some of the features may alternatively be provided in an apparatus that does not require a humidifier and therefore does not require the liquid chamber 300 or chamber bay 108 features. For example, it will be appreciated that the configuration that isolates the motor and gasflow path from the electrical and electronic components has broad applications in other types of gas delivery apparatuses.

The 'flow therapy apparatus' language is intended to cover all such variants.

Reference to any prior art in this specification is not, and should not be taken as, an acknowledgement or any form of suggestion that that prior art forms part of the common general knowledge in the field of endeavour in any country in the world.

Where reference is used herein to directional terms such as "up", "down", "forward", "rearward", "horizontal", "vertical" etc, those terms refer to when the apparatus is in a typical in-use position, and are used to show and/or describe relative directions or orientations.

The invention claimed is:

1. A blower for an apparatus for delivering a flow of gas, the blower comprising:
a stator including a first stator ledge and a second stator ledge; and
a casing, comprising:
a plurality of casing ledges and at least one flexible or resilient member, wherein the plurality of casing ledges support the first stator ledge, and the at least one flexible or resilient member supports the second stator ledge; or at least one casing ledge and a plurality of flexible or resilient members, wherein the at least one casing ledge supports the first stator ledge, and the plurality of flexible or resilient members support the second stator ledge.

2. The blower of claim 1, further comprising:
a casing cap operatively connected to the casing; and
a vibration isolating member located between the stator and the casing cap arranged to bias the stator in a direction towards the first stator ledge.

3. The blower of claim 2, wherein the vibration isolating member is compressible.

4. The blower of claim 2, wherein the vibration isolating member comprises an elastomeric material.

5. The blower of claim 4, wherein the elastomeric material is silicone.

6. The blower of claim 1, wherein the at least one flexible or resilient member is configured to flex beyond a periphery of the stator to allow removal of the stator from the casing.

7. The blower of claim 1, wherein the casing includes a top casing and a bottom casing, which engage around their respective peripheries, with a partition between the top casing and the bottom casing.

8. The blower of claim 7, wherein the bottom casing includes a casing cap.

9. The blower of claim 7, wherein the at least one casing ledge comprises a plurality of casing ledges located on the bottom casing and wherein the at least one flexible or resilient member comprises a plurality of flexible or resilient members located on the bottom casing.

10. The blower of claim 9, wherein the plurality of casing ledges and the plurality of flexible or resilient members are integrally formed with the bottom casing.

11. The blower of claim 1, wherein each casing ledge of the plurality of casing ledges has a curved inner surface that substantially corresponds to a curve of the stator.

12. The blower of claim 1, wherein the first stator ledge is a peripheral ledge that cooperates with the plurality of casing ledges, and the second stator ledge is a recess or an underside of the peripheral ledge under the first stator ledge that cooperates with the at least one flexible or resilient member of the casing to support the stator; or
the first stator ledge is a peripheral ledge that cooperates with the at least one casing ledge, and the second stator ledge is a recess or an underside of the peripheral ledge under the first stator ledge that cooperates with the plurality of flexible or resilient members of the casing to support the stator.

13. The blower of claim 1, wherein the at least one casing ledge comprises a plurality of casing ledges and the at least one flexible or resilient member comprises a plurality of flexible or resilient members, wherein the plurality of casing ledges support the first stator ledge, and the plurality of flexible or resilient members support the second stator ledge.

14. A blower for an apparatus for delivering a flow of gas, the blower comprising:
a top casing;
a bottom casing configured to engage the top casing, the bottom casing including at least one casing ledge and at least one flexible or resilient member; and
a stator including a first stator ledge and a second stator ledge,
wherein the at least one casing ledge supports the first stator ledge, and the at least one flexible or resilient member supports the second stator ledge.

15. A blower for an apparatus for delivering a flow of gas, the blower comprising:
a casing including at least one casing ledge and at least one flexible or resilient member; and
a stator including a first stator ledge and a second stator ledge,
wherein the at least one casing ledge supports the first stator ledge, and the at least one flexible or resilient member supports the second stator ledge, wherein the at least one flexible or resilient member is configured to flex beyond a periphery of the stator to allow removal of the stator from the casing.

* * * * *